US011998386B2

(12) United States Patent
Lindekugel et al.

(10) Patent No.: US 11,998,386 B2
(45) Date of Patent: Jun. 4, 2024

(54) SUPPORT AND COVER STRUCTURES FOR AN ULTRASOUND PROBE HEAD

(71) Applicant: C. R. Bard, Inc., Franklin Lakes, NJ (US)

(72) Inventors: Eric W. Lindekugel, Salt Lake City, UT (US); Jeremy B. Cox, Salt Lake City, UT (US); Daniel B. Blanchard, Bountiful, UT (US); Christian W. Crook, West Jordan, UT (US); Eddie K. Burnside, Bountiful, UT (US); Jeanette E. Southard, Castleconnell (IE); Kevin W. Stinger, Kaysville, UT (US); Amir Orome, Sandy, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 816 days.

(21) Appl. No.: 16/854,789

(22) Filed: Apr. 21, 2020

(65) Prior Publication Data

US 2020/0245971 A1 Aug. 6, 2020

Related U.S. Application Data

(63) Continuation of application No. 13/206,396, filed on Aug. 9, 2011, now Pat. No. 10,639,008, which is a
(Continued)

(51) Int. Cl.
*A61B 8/00* (2006.01)
*A61B 17/34* (2006.01)
(52) U.S. Cl.
CPC .......... *A61B 8/4281* (2013.01); *A61B 8/4411* (2013.01); *A61B 8/4455* (2013.01);
(Continued)

(58) Field of Classification Search
CPC ............... A61B 10/00; A61B 17/3403; A61B 2017/3413; A61B 2560/0406;
(Continued)

(56) References Cited

U.S. PATENT DOCUMENTS 3,133,244 A 5/1964 Wojtulewicz
3,297,020 A 1/1967 Mathiesen
(Continued)

FOREIGN PATENT DOCUMENTS

AU 642647 B2 10/1993
AU 1860597 B2 6/1999
(Continued)

OTHER PUBLICATIONS

Popp, M. B. et al., Accuracy of implanted port placement with the use of the electromagnetic CathTrack® catheter locator system, The Journal of Vascular Access 2005; 6: 9-12.
(Continued)

*Primary Examiner* — Rochelle D Turchen
(74) *Attorney, Agent, or Firm* — Rutan & Tucker LLP

(57) ABSTRACT

An ultrasound probe assembly includes an ultrasound probe, an ultrasound cap, a solid hydrogel component, and a cover. The ultrasound probe can include a probe head and an orientation indicator. The probe head includes an acoustic surface. The ultrasound cap can include an opening defined by an opening perimeter, and a base configured to support a removable needle guide. The base can be aligned with the orientation indicator. The solid hydrogel component can include a probe-contacting side contacting the acoustic surface, a skin-contacting side extending through the opening, and an outer perimeter larger than the opening perimeter. The cover can be configured to cover the hydrogel component and at least a portion of the ultrasound cap.

13 Claims, 26 Drawing Sheets

Related U.S. Application Data continuation-in-part of application No. 12/900,750, filed on Oct. 8, 2010, now Pat. No. 11,103,213.

(60) Provisional application No. 61/372,044, filed on Aug. 9, 2010, provisional application No. 61/249,850, filed on Oct. 8, 2009.

(52) U.S. Cl.
CPC ......... *A61B 8/4422* (2013.01); *A61B 17/3403* (2013.01); *A61B 2017/3413* (2013.01)

(58) Field of Classification Search
CPC ... A61B 8/4281; A61B 8/4411; A61B 8/4422; A61B 8/4455; A61B 8/4472
See application file for complete search history.

(56) References Cited

U.S. PATENT DOCUMENTS

| | | |
|---|---|---|
| 3,625,200 A | 12/1971 | Muller |
| 3,674,014 A | 7/1972 | Tillander |
| 3,817,241 A | 6/1974 | Grausz |
| 3,847,157 A | 11/1974 | Caillouette et al. |
| 3,868,565 A | 2/1975 | Kuipers |
| 3,902,501 A | 9/1975 | Citron et al. |
| 3,995,623 A | 12/1976 | Blake et al. |
| 4,003,369 A | 1/1977 | Heilman et al. |
| 4,063,561 A | 12/1977 | McKenna |
| 4,072,146 A | 2/1978 | Howes |
| 4,114,601 A | 9/1978 | Abels |
| 4,149,535 A | 4/1979 | Volder |
| 4,173,228 A | 11/1979 | Van Steenwyk et al. |
| 4,175,566 A | 11/1979 | Millar |
| 4,181,120 A | 1/1980 | Kunii et al. |
| 4,224,949 A | 9/1980 | Scott et al. |
| 4,244,362 A | 1/1981 | Anderson |
| 4,246,792 A | 1/1981 | Matzuk |
| 4,289,139 A | 9/1981 | Enjoji et al. |
| 4,317,078 A | 2/1982 | Weed et al. |
| 4,327,722 A | 5/1982 | Groshong et al. |
| 4,362,166 A | 12/1982 | Furler et al. |
| 4,365,639 A | 12/1982 | Goldreyer |
| 4,380,237 A | 4/1983 | Newbower |
| 4,402,324 A | 9/1983 | Lindgren et al. |
| 4,407,294 A | 10/1983 | Vilkomerson |
| 4,429,693 A | 2/1984 | Blake et al. |
| 4,431,005 A | 2/1984 | McCormick |
| 4,431,214 A | 2/1984 | Buffington |
| 4,445,501 A | 5/1984 | Bresler |
| 4,459,854 A | 7/1984 | Richardson et al. |
| 4,469,106 A | 9/1984 | Harui |
| 4,483,343 A | 11/1984 | Beyer et al. |
| 4,491,137 A | 1/1985 | Jingu |
| 4,565,201 A | 1/1986 | Lass |
| 4,572,198 A | 2/1986 | Codrington |
| 4,577,634 A | 3/1986 | Gessman |
| 4,582,067 A | 4/1986 | Silverstein et al. |
| 4,588,394 A | 5/1986 | Schulte et al. |
| 4,593,687 A | 6/1986 | Gray |
| 4,593,699 A | 6/1986 | Poncy et al. |
| 4,595,012 A | 6/1986 | Webler et al. |
| 4,601,706 A | 7/1986 | Aillon |
| 4,608,989 A | 9/1986 | Drue |
| 4,608,992 A | 9/1986 | Hakim et al. |
| 4,619,247 A | 10/1986 | Inoue et al. |
| 4,622,644 A | 11/1986 | Hansen |
| 4,644,960 A | 2/1987 | Johans |
| 4,652,820 A | 3/1987 | Maresca |
| 4,665,925 A | 5/1987 | Millar |
| 4,667,230 A | 5/1987 | Arakawa et al. |
| 4,674,518 A | 6/1987 | Salo |
| 4,676,249 A | 6/1987 | Arenas et al. |
| 4,681,106 A | 7/1987 | Kensey et al. |
| 4,681,117 A | 7/1987 | Brodman et al. |
| 4,688,578 A | 8/1987 | Takano et al. |
| 4,692,148 A | 9/1987 | Kantrowitz et al. |
| 4,697,595 A | 10/1987 | Breyer et al. |
| 4,700,997 A | 10/1987 | Strand |
| 4,706,681 A | 11/1987 | Breyer et al. |
| 4,710,708 A | 12/1987 | Rorden et al. |
| 4,733,669 A | 3/1988 | Segal |
| 4,737,794 A | 4/1988 | Jones |
| 4,741,356 A | 5/1988 | Letzo et al. |
| 4,742,356 A | 5/1988 | Kuipers |
| 4,753,247 A | 6/1988 | Kirsner |
| 4,770,185 A | 9/1988 | Silverstein et al. |
| 4,771,788 A | 9/1988 | Millar |
| 4,781,685 A | 11/1988 | Lehmann et al. |
| 4,784,646 A | 11/1988 | Feingold |
| 4,787,070 A | 11/1988 | Suzuki et al. |
| 4,787,396 A | 11/1988 | Pidorenko |
| 4,793,361 A | 12/1988 | DuFault |
| 4,794,930 A | 1/1989 | Machida et al. |
| 4,796,632 A | 1/1989 | Boyd et al. |
| 4,798,588 A | 1/1989 | Aillon |
| 4,798,598 A | 1/1989 | Bonello et al. |
| 4,809,681 A | 3/1989 | Kantrowitz et al. |
| 4,809,713 A | 3/1989 | Grayzel |
| 4,813,729 A | 3/1989 | Speckhart |
| 4,821,731 A | 4/1989 | Martinelli et al. |
| 4,836,214 A | 6/1989 | Sramek |
| 4,840,622 A | 6/1989 | Hardy |
| 4,849,692 A | 7/1989 | Blood |
| 4,850,358 A | 7/1989 | Millar |
| 4,852,580 A | 8/1989 | Wood |
| 4,856,317 A | 8/1989 | Pidorenko et al. |
| 4,856,529 A | 8/1989 | Segal |
| 4,860,757 A | 8/1989 | Lynch et al. |
| 4,867,169 A | 9/1989 | Machida et al. |
| 4,869,263 A | 9/1989 | Segal et al. |
| 4,869,718 A | 9/1989 | Brader |
| 4,887,606 A | 12/1989 | Yock et al. |
| 4,887,615 A | 12/1989 | Taylor |
| 4,889,128 A | 12/1989 | Millar |
| 4,899,756 A | 2/1990 | Sonek |
| 4,901,725 A | 2/1990 | Nappholz et al. |
| 4,905,698 A | 3/1990 | Strohl, Jr. et al. |
| 4,911,173 A | 3/1990 | Terwilliger |
| 4,911,174 A | 3/1990 | Pederson et al. |
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,995,396 A | 2/1991 | Inaba et al. |
| 4,998,916 A | 3/1991 | Hammerslag et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |
| 5,040,548 A | 8/1991 | Yock |
| 5,042,486 A | 8/1991 | Pfeiler et al. |
| 5,045,071 A | 9/1991 | McCormick et al. |
| 5,046,497 A | 9/1991 | Millar |
| 5,050,607 A | 9/1991 | Bradley et al. |
| 5,057,095 A | 10/1991 | Fabian |
| 5,058,595 A | 10/1991 | Kern |
| 5,067,489 A | 11/1991 | Lind |
| 5,076,278 A | 12/1991 | Vilkomerson et al. |
| 5,076,279 A | 12/1991 | Arenson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A | 1/1992 | Katims |
| 5,078,714 A | 1/1992 | Katims |
| 5,084,022 A | 1/1992 | Claude |
| 5,092,341 A | 3/1992 | Kelen |
| 5,099,845 A | 3/1992 | Besz et al. |

(56) References Cited

U.S. PATENT DOCUMENTS

| | | |
|---|---|---|
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A | 6/1992 | Katims |
| D327,740 S | 7/1992 | Arioka et al. |
| 5,134,370 A | 7/1992 | Jefferts et al. |
| 5,144,955 A | 9/1992 | O'Hara |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,184,601 A | 2/1993 | Putman |
| 5,190,045 A | 3/1993 | Frazin |
| 5,202,985 A | 4/1993 | Goyal |
| 5,211,165 A | 5/1993 | Dumoulin et al. |
| 5,211,636 A | 5/1993 | Mische |
| 5,212,988 A | 5/1993 | White et al. |
| 5,214,615 A | 5/1993 | Bauer |
| 5,217,026 A | 6/1993 | Stoy et al. |
| 5,220,924 A | 6/1993 | Frazin |
| 5,235,987 A | 8/1993 | Wolfe |
| 5,239,464 A | 8/1993 | Blair et al. |
| 5,240,004 A | 8/1993 | Walinsky et al. |
| 5,243,995 A | 9/1993 | Maier |
| 5,246,007 A | 9/1993 | Frisbie et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,259,386 A | 11/1993 | Sharkawy |
| 5,261,409 A | 11/1993 | Dardel |
| 5,265,610 A | 11/1993 | Darrow et al. |
| 5,265,614 A | 11/1993 | Hayakawa et al. |
| 5,267,569 A | 12/1993 | Lienhard |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,295,485 A | 3/1994 | Shinomura et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,860 A | 7/1994 | Seward et al. |
| 5,325,873 A | 7/1994 | Hirschi et al. |
| 5,330,496 A | 7/1994 | Alferness |
| 5,331,966 A | 7/1994 | Bennett et al. |
| 5,333,614 A | 8/1994 | Feiring |
| 5,337,678 A | 8/1994 | Grout |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,369,624 A | 11/1994 | Fukukita et al. |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,390,675 A | 2/1995 | Sheehan et al. |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,405,366 A | 4/1995 | Fox et al. |
| 5,411,485 A | 5/1995 | Tennican et al. |
| 5,413,107 A | 5/1995 | Oakley et al. |
| 5,422,478 A | 6/1995 | Wlodarczyk et al. |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |
| 5,437,276 A | 8/1995 | Takada |
| 5,437,277 A | 8/1995 | Dumoulin et al. |
| 5,438,873 A | 8/1995 | Wlodarczyk et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,450,846 A | 9/1995 | Goldreyer |
| 5,453,575 A | 9/1995 | O'Donnell et al. |
| 5,456,256 A | 10/1995 | Schneider et al. |
| 5,456,718 A | 10/1995 | Szymaitis |
| 5,464,016 A | 11/1995 | Nicholas et al. |
| 5,469,851 A | 11/1995 | Lipschutz |
| 5,474,065 A | 12/1995 | Meathrel et al. |
| 5,476,090 A | 12/1995 | Kishi |
| 5,480,422 A | 1/1996 | Ben-Haim |
| 5,487,729 A | 1/1996 | Avellanet et al. |
| 5,490,522 A | 2/1996 | Dardel |
| 5,492,538 A | 2/1996 | Johlin, Jr. |
| 5,494,038 A | 2/1996 | Wang et al. |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,853 A | 5/1996 | Smith et al. |
| 5,522,878 A | 6/1996 | Montecalvo et al. |
| 5,526,812 A | 6/1996 | Dumoulin et al. |
| 5,531,664 A | 7/1996 | Adachi et al. |
| 5,540,033 A | 7/1996 | Fox et al. |
| 5,540,230 A | 7/1996 | Vilkomerson |
| 5,540,681 A | 7/1996 | Strul et al. |
| 5,542,938 A | 8/1996 | Avellanet et al. |
| 5,546,949 A | 8/1996 | Frazin et al. |
| 5,546,951 A | 8/1996 | Ben-Haim |
| 5,558,091 A | 9/1996 | Acker et al. |
| 5,568,809 A | 10/1996 | Ben-haim |
| 5,569,183 A | 10/1996 | Kieturakis |
| D375,450 S | 11/1996 | Bidwell et al. |
| 5,570,671 A | 11/1996 | Hickey |
| 5,575,291 A | 11/1996 | Hayakawa et al. |
| 5,583,286 A | 12/1996 | Matsuyama |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,610,967 A | 3/1997 | Moorman et al. |
| 5,615,678 A | 4/1997 | Kirkham et al. |
| 5,617,864 A | 4/1997 | Stouffer et al. |
| 5,617,866 A | 4/1997 | Marian, Jr. |
| 5,622,169 A | 4/1997 | Golden et al. |
| 5,622,170 A | 4/1997 | Schulz |
| 5,622,184 A | 4/1997 | Ashby et al. |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,630,419 A | 5/1997 | Ranalletta |
| 5,640,960 A | 6/1997 | Jones et al. |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| D383,968 S | 9/1997 | Bidwell et al. |
| 5,662,115 A | 9/1997 | Torp et al. |

(56) References Cited

U.S. PATENT DOCUMENTS

| | | |
|---|---|---|
| 5,665,477 A | 9/1997 | Meathrel et al. |
| 5,666,473 A | 9/1997 | Wallace |
| 5,666,958 A | 9/1997 | Rothenberg et al. |
| 5,668,888 A | 9/1997 | Doi et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,713,362 A | 2/1998 | Vilkomerson |
| 5,713,363 A | 2/1998 | Seward et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |
| D391,838 S | 3/1998 | Bidwell et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,738,099 A | 4/1998 | Chang |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,779,638 A | 7/1998 | Vesely et al. |
| 5,782,767 A | 7/1998 | Pretlow, III |
| 5,782,769 A | 7/1998 | Hwang et al. |
| 5,785,657 A | 7/1998 | Breyer et al. |
| 5,787,049 A | 7/1998 | Bates |
| 5,792,055 A | 8/1998 | McKinnon |
| 5,795,297 A | 8/1998 | Daigle |
| 5,795,298 A | 8/1998 | Vesely et al. |
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| 5,816,245 A | 10/1998 | Manseur et al. |
| 5,817,022 A | 10/1998 | Vesely |
| 5,817,024 A | 10/1998 | Ogle et al. |
| 5,820,549 A | 10/1998 | Marian, Jr. |
| 5,824,031 A | 10/1998 | Cookston et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |
| 5,835,561 A | 11/1998 | Moorman et al. |
| 5,836,882 A | 11/1998 | Frazin |
| 5,836,990 A | 11/1998 | Li |
| 5,840,024 A | 11/1998 | Taniguchi et al. |
| 5,840,025 A | 11/1998 | Ben-Haim |
| 5,840,030 A | 11/1998 | Ferek-Petric et al. |
| 5,840,031 A | 11/1998 | Crowley |
| 5,842,986 A | 12/1998 | Avrin et al. |
| 5,843,076 A | 12/1998 | Webster, Jr. et al. |
| 5,843,153 A | 12/1998 | Johnston et al. |
| 5,844,140 A | 12/1998 | Seale |
| 5,846,198 A | 12/1998 | Killmann |
| 5,855,553 A | 1/1999 | Tajima et al. |
| 5,855,558 A | 1/1999 | Nakao et al. |
| 5,859,893 A | 1/1999 | Moorman et al. |
| 5,865,748 A | 2/1999 | Co et al. |
| 5,868,673 A | 2/1999 | Vesely |
| 5,873,822 A | 2/1999 | Ferre et al. |
| 5,876,328 A | 3/1999 | Fox et al. |
| 5,879,297 A | 3/1999 | Haynor et al. |
| 5,893,363 A | 4/1999 | Little et al. |
| 5,897,495 A | 4/1999 | Aida et al. |
| 5,899,860 A | 5/1999 | Pfeiffer et al. |
| 5,902,238 A | 5/1999 | Golden et al. |
| 5,907,487 A | 5/1999 | Rosenberg et al. |
| 5,908,385 A | 6/1999 | Chechelski et al. |
| 5,910,113 A | 6/1999 | Pruter |
| 5,910,120 A | 6/1999 | Kim et al. |
| 5,913,820 A | 6/1999 | Bladen et al. |
| 5,913,830 A | 6/1999 | Miles |
| 5,919,141 A | 7/1999 | Money et al. |
| 5,919,170 A | 7/1999 | Woessner |
| 5,928,145 A | 7/1999 | Ocali et al. |
| 5,929,607 A | 7/1999 | Rosenberg et al. |
| 5,931,786 A | 8/1999 | Whitmore, III et al. |
| 5,931,788 A | 8/1999 | Keen et al. |
| 5,931,818 A | 8/1999 | Werp et al. |
| 5,941,858 A | 8/1999 | Johnson |
| 5,941,889 A | 8/1999 | Cermak |
| 5,941,904 A | 8/1999 | Johnston et al. |
| 5,944,022 A | 8/1999 | Nardella et al. |
| 5,944,023 A | 8/1999 | Johnson et al. |
| 5,953,683 A | 9/1999 | Hansen et al. |
| 5,957,857 A | 9/1999 | Hartley |
| 5,961,923 A | 10/1999 | Nova et al. |
| 5,967,978 A | 10/1999 | Littmann et al. |
| 5,967,980 A | 10/1999 | Ferre et al. |
| 5,967,991 A | 10/1999 | Gardineer et al. |
| 5,969,722 A | 10/1999 | Palm |
| 5,978,705 A | 11/1999 | KenKnight et al. |
| 5,982,915 A | 11/1999 | Doi et al. |
| 5,983,126 A | 11/1999 | Wittkampf |
| 5,984,908 A | 11/1999 | Davis et al. |
| 5,991,693 A | 11/1999 | Zalewski |
| 5,997,473 A | 12/1999 | Taniguchi et al. |
| 5,997,481 A | 12/1999 | Adams et al. |
| 6,006,123 A | 12/1999 | Nguyen et al. |
| 6,011,988 A | 1/2000 | Lynch et al. |
| 6,014,473 A | 1/2000 | Hossack et al. |
| 6,014,580 A | 1/2000 | Blume et al. |
| 6,015,414 A | 1/2000 | Werp et al. |
| 6,017,496 A | 1/2000 | Nova et al. |
| 6,019,724 A | 2/2000 | Gronningsaeter et al. |
| 6,019,725 A | 2/2000 | Vesely et al. |
| 6,023,638 A | 2/2000 | Swanson |
| 6,026,312 A | 2/2000 | Shemwell et al. |
| 6,031,765 A | 2/2000 | Lee et al. |
| 6,032,070 A | 2/2000 | Flock et al. |
| 6,039,694 A | 3/2000 | Larson et al. |
| 6,050,718 A | 4/2000 | Schena et al. |
| 6,052,610 A | 4/2000 | Koch |
| 6,052,618 A | 4/2000 | Dahlke et al. |
| D424,693 S | 5/2000 | Pruter |
| 6,059,718 A | 5/2000 | Taniguchi et al. |
| 6,064,903 A | 5/2000 | Riechers et al. |
| 6,064,905 A | 5/2000 | Webster, Jr. et al. |
| 6,066,094 A | 5/2000 | Ben-Haim |
| 6,068,599 A | 5/2000 | Saito et al. |

(56) References Cited

U.S. PATENT DOCUMENTS

| | | | |
|---|---|---|---|
| 6,073,043 A | 6/2000 | Schneider |
| 6,074,367 A | 6/2000 | Hubbell |
| 6,075,442 A | 6/2000 | Welch |
| 6,076,007 A | 6/2000 | England et al. |
| 6,082,366 A | 7/2000 | Andra et al. |
| 6,083,170 A | 7/2000 | Ben-Haim |
| 6,099,524 A | 8/2000 | Lipson et al. |
| 6,100,026 A | 8/2000 | Nova et al. |
| 6,102,044 A | 8/2000 | Naidyhorski |
| 6,106,472 A | 8/2000 | Chiang et al. |
| 6,107,699 A | 8/2000 | Swanson |
| 6,112,111 A | 8/2000 | Glantz |
| 6,113,504 A | 9/2000 | Kuesters |
| 6,113,547 A | 9/2000 | Catallo et al. |
| 6,115,624 A | 9/2000 | Lewis et al. |
| 6,117,085 A | 9/2000 | Picatti et al. |
| 6,120,445 A | 9/2000 | Grunwald |
| 6,126,608 A | 10/2000 | Kemme et al. |
| 6,128,174 A | 10/2000 | Ritter et al. |
| 6,129,668 A | 10/2000 | Haynor et al. |
| 6,132,378 A | 10/2000 | Marino |
| 6,132,379 A | 10/2000 | Patacsil et al. |
| 6,135,961 A | 10/2000 | Pflugrath et al. |
| 6,136,274 A | 10/2000 | Nova et al. |
| 6,138,681 A | 10/2000 | Chen et al. |
| 6,139,496 A | 10/2000 | Chen et al. |
| 6,139,502 A | 10/2000 | Fredriksen |
| 6,142,946 A | 11/2000 | Hwang et al. |
| 6,144,300 A | 11/2000 | Dames |
| 6,148,823 A | 11/2000 | Hastings |
| 6,152,933 A | 11/2000 | Werp et al. |
| 6,157,853 A | 12/2000 | Blume et al. |
| 6,165,144 A | 12/2000 | Talish et al. |
| 6,166,496 A | 12/2000 | Lys et al. |
| 6,166,806 A | 12/2000 | Tjin |
| 6,167,765 B1 | 1/2001 | Weitzel |
| 6,172,499 B1 | 1/2001 | Ashe |
| 6,173,199 B1 | 1/2001 | Gabriel |
| 6,173,715 B1 | 1/2001 | Sinanan et al. |
| 6,175,756 B1 | 1/2001 | Ferre et al. |
| 6,176,829 B1 | 1/2001 | Vilkomerson |
| 6,193,743 B1 | 2/2001 | Brayton et al. |
| 6,200,305 B1 | 3/2001 | Berthiaume et al. |
| 6,203,498 B1 | 3/2001 | Bunce et al. |
| 6,203,499 B1 | 3/2001 | Imling et al. |
| 6,206,843 B1 | 3/2001 | Iger et al. |
| 6,208,884 B1 | 3/2001 | Kumar et al. |
| 6,211,626 B1 | 4/2001 | Lys et al. |
| 6,211,666 B1 | 4/2001 | Acker |
| 6,212,426 B1 | 4/2001 | Swanson |
| 6,216,027 B1 | 4/2001 | Willis et al. |
| 6,216,028 B1 | 4/2001 | Haynor et al. |
| 6,216,029 B1 | 4/2001 | Paltieli |
| 6,223,087 B1 | 4/2001 | Williams |
| 6,226,547 B1 | 5/2001 | Lockhart et al. |
| 6,230,046 B1 | 5/2001 | Crane et al. |
| 6,233,476 B1 | 5/2001 | Strommer et al. |
| 6,233,479 B1 | 5/2001 | Haddad et al. |
| 6,238,344 B1 | 5/2001 | Gamelsky et al. |
| 6,241,673 B1 | 6/2001 | Williams |
| 6,246,231 B1 | 6/2001 | Ashe |
| 6,246,898 B1 | 6/2001 | Vesely et al. |
| 6,248,072 B1 | 6/2001 | Murkin |
| 6,248,074 B1 | 6/2001 | Ohno et al. |
| 6,248,075 B1 | 6/2001 | McGee et al. |
| 6,251,073 B1 | 6/2001 | Imran et al. |
| 6,253,770 B1 | 7/2001 | Acker et al. |
| 6,259,941 B1 | 7/2001 | Chia et al. |
| 6,261,231 B1 | 7/2001 | Damphousse et al. |
| 6,263,230 B1 | 7/2001 | Haynor et al. |
| 6,266,550 B1 | 7/2001 | Selmon et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,271,833 B1 | 8/2001 | Rosenberg et al. |
| 6,272,371 B1 | 8/2001 | Shlomo |
| 6,272,374 B1 | 8/2001 | Flock et al. |
| 6,275,258 B1 | 8/2001 | Chim |
| 6,275,724 B1 | 8/2001 | Dickinson et al. |
| 6,277,077 B1 | 8/2001 | Brisken et al. |
| 6,284,459 B1 | 9/2001 | Nova et al. |
| 6,285,898 B1 | 9/2001 | Ben-Haim |
| 6,288,704 B1 | 9/2001 | Flack et al. |
| 6,292,678 B1 | 9/2001 | Hall et al. |
| 6,292,680 B1 | 9/2001 | Somogyi et al. |
| 6,292,901 B1 | 9/2001 | Lys et al. |
| 6,293,955 B1 | 9/2001 | Houser et al. |
| 6,296,604 B1 | 10/2001 | Garibaldi et al. |
| 6,296,614 B1 | 10/2001 | Pruter |
| 6,298,261 B1 | 10/2001 | Rex |
| 6,304,768 B1 | 10/2001 | Blume et al. |
| 6,306,097 B1 | 10/2001 | Park et al. |
| 6,311,082 B1 | 10/2001 | Creighton, IV et al. |
| 6,315,709 B1 | 11/2001 | Garibaldi et al. |
| 6,315,727 B1 | 11/2001 | Coleman et al. |
| 6,319,668 B1 | 11/2001 | Nova et al. |
| 6,323,769 B1 | 11/2001 | Dames |
| 6,323,770 B1 | 11/2001 | Dames |
| 6,324,416 B1 | 11/2001 | Seibert |
| 6,325,540 B1 | 12/2001 | Lounsberry et al. |
| 6,325,762 B1 | 12/2001 | Tjin |
| 6,329,139 B1 | 12/2001 | Nova et al. |
| 6,329,916 B1 | 12/2001 | Dames |
| 6,330,467 B1 | 12/2001 | Creighton, IV et al. |
| 6,332,089 B1 | 12/2001 | Acker et al. |
| 6,332,874 B1 | 12/2001 | Eliasen et al. |
| 6,340,588 B1 | 1/2002 | Nova et al. |
| 6,340,868 B1 | 1/2002 | Lys et al. |
| 6,341,231 B1 | 1/2002 | Ferre et al. |
| 6,346,081 B1 | 2/2002 | Vilkomerson |
| 6,348,911 B1 | 2/2002 | Rosenberg et al. |
| 6,350,160 B1 | 2/2002 | Feuersanger et al. |
| 6,352,363 B1 | 3/2002 | Munger et al. |
| 6,355,026 B1 | 3/2002 | Mick |
| 6,361,499 B1 | 3/2002 | Bates et al. |
| 6,364,823 B1 | 4/2002 | Garibaldi et al. |
| 6,364,839 B1 | 4/2002 | Little et al. |
| 6,366,804 B1 | 4/2002 | Mejia |
| 6,368,285 B1 | 4/2002 | Osadchy et al. |
| 6,370,411 B1 | 4/2002 | Osadchy et al. |
| 6,373,240 B1 | 4/2002 | Govari |
| 6,373,388 B1 | 4/2002 | Dames |
| 6,374,134 B1 | 4/2002 | Bladen et al. |
| 6,374,670 B1 | 4/2002 | Spelman et al. |
| 6,375,606 B1 | 4/2002 | Garibaldi et al. |
| 6,375,639 B1 | 4/2002 | Duplessie et al. |
| 6,377,857 B1 | 4/2002 | Brayton et al. |
| 6,379,302 B1 | 4/2002 | Kessman et al. |
| 6,379,303 B1 | 4/2002 | Seitz et al. |
| 6,379,307 B1 | 4/2002 | Filly et al. |
| 6,381,485 B1 | 4/2002 | Hunter et al. |
| 6,383,139 B1 | 5/2002 | Hwang et al. |
| 6,385,472 B1 | 5/2002 | Hall et al. |
| 6,385,476 B1 | 5/2002 | Osadchy et al. |
| 6,398,736 B1 | 6/2002 | Seward |
| 6,401,723 B1 | 6/2002 | Garibaldi et al. |
| 6,406,442 B1 | 6/2002 | McFann et al. |
| 6,412,978 B1 | 7/2002 | Watanabe et al. |
| 6,412,980 B1 | 7/2002 | Lounsberry et al. |
| 6,416,475 B1 | 7/2002 | Hwang et al. |
| 6,417,839 B1 | 7/2002 | Odell |
| 6,418,332 B1 | 7/2002 | Mastrototaro et al. |
| 6,418,335 B2 | 7/2002 | Avrin et al. |
| 6,423,002 B1 | 7/2002 | Hossack |
| 6,423,050 B1 | 7/2002 | Twardowski |
| 6,427,079 B1 | 7/2002 | Schneider et al. |
| 6,428,551 B1 | 8/2002 | Hall et al. |
| 6,430,315 B1 | 8/2002 | Makram-Ebeid |
| 6,432,069 B1 | 8/2002 | Godo et al. |
| 6,436,050 B2 | 8/2002 | Garrison et al. |
| 6,438,411 B1 | 8/2002 | Guttman et al. |
| 6,442,416 B1 | 8/2002 | Schultz |
| 6,443,902 B1 | 9/2002 | Sasady |
| 6,443,907 B1 | 9/2002 | Mansy et al. |

(56) References Cited

U.S. PATENT DOCUMENTS

| | | |
|---|---|---|
| 6,445,943 B1 | 9/2002 | Ferre et al. |
| 6,459,919 B1 | 10/2002 | Lys et al. |
| 6,463,121 B1 | 10/2002 | Milnes |
| 6,473,167 B1 | 10/2002 | Odell |
| 6,474,341 B1 | 11/2002 | Hunter et al. |
| 6,475,146 B1 | 11/2002 | Frelburger et al. |
| 6,475,152 B1 | 11/2002 | Kelly, Jr. et al. |
| 6,475,223 B1 | 11/2002 | Werp et al. |
| 6,477,402 B1 | 11/2002 | Lynch et al. |
| 6,484,118 B1 | 11/2002 | Govari |
| 6,485,426 B2 | 11/2002 | Sandhu |
| 6,487,916 B1 | 12/2002 | Gomm et al. |
| 6,491,671 B1 | 12/2002 | Larson, III et al. |
| 6,493,573 B1 | 12/2002 | Martinelli et al. |
| 6,496,715 B1 | 12/2002 | Lee et al. |
| 6,498,944 B1 | 12/2002 | Ben-Haim et al. |
| 6,500,141 B1 | 12/2002 | Irion et al. |
| 6,505,062 B1 | 1/2003 | Ritter et al. |
| 6,507,751 B2 | 1/2003 | Blume et al. |
| 6,508,802 B1 | 1/2003 | Rosengart et al. |
| 6,512,958 B1 | 1/2003 | Swoyer et al. |
| 6,514,249 B1 | 2/2003 | Maguire et al. |
| 6,515,657 B1 | 2/2003 | Zanelli |
| 6,516,212 B1 | 2/2003 | Bladen et al. |
| 6,516,231 B1 | 2/2003 | Flammang |
| 6,516,807 B1 | 2/2003 | Panescu et al. |
| 6,517,491 B1 | 2/2003 | Thiele et al. |
| 6,517,520 B2 | 2/2003 | Chang et al. |
| 6,522,906 B1 | 2/2003 | Salisbury, Jr. et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,530,887 B1 | 3/2003 | Gilbert et al. |
| 6,534,982 B1 | 3/2003 | Jakab |
| 6,535,625 B1 | 3/2003 | Chang et al. |
| 6,537,192 B1 | 3/2003 | Elliott et al. |
| 6,537,196 B1 | 3/2003 | Creighton, IV et al. |
| 6,538,634 B1 | 3/2003 | Chui et al. |
| 6,540,685 B1 | 4/2003 | Rhoads et al. |
| 6,540,699 B1 | 4/2003 | Smith |
| 6,542,766 B2 | 4/2003 | Hall et al. |
| 6,544,251 B1 | 4/2003 | Crawford |
| 6,546,270 B1 | 4/2003 | Goldin et al. |
| 6,546,279 B1 | 4/2003 | Bova et al. |
| 6,546,787 B1 | 4/2003 | Schiller et al. |
| 6,549,794 B1 | 4/2003 | Nadeau, Jr. et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,571,004 B1 | 5/2003 | Florent et al. |
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,593,754 B1 | 7/2003 | Steber et al. |
| 6,593,884 B1 | 7/2003 | Gilboa et al. |
| 6,596,791 B2 | 7/2003 | Santar et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |
| 6,615,071 B1 | 9/2003 | Casscells, III et al. |
| 6,615,155 B2 | 9/2003 | Gilboa |
| 6,618,612 B1 | 9/2003 | Acker et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,645,148 B2 | 11/2003 | Nguyen-Dinh et al. |
| 6,648,875 B2 | 11/2003 | Simpson et al. |
| 6,649,914 B1 | 11/2003 | Moorman et al. |
| 6,652,506 B2 | 11/2003 | Bowe et al. |
| 6,662,034 B2 | 12/2003 | Segner et al. |
| 6,669,633 B2 | 12/2003 | Brodsky et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo et al. |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |
| 6,701,918 B2 | 3/2004 | Fariss et al. |
| 6,702,749 B2 | 3/2004 | Paladini et al. |
| 6,702,804 B1 | 3/2004 | Ritter et al. |
| 6,704,590 B2 | 3/2004 | Haldeman |
| 6,709,390 B1 | 3/2004 | Marie Pop |
| 6,711,429 B1 | 3/2004 | Gilboa et al. |
| 6,711,431 B2 | 3/2004 | Sarin et al. |
| 6,719,698 B2 | 4/2004 | Manor et al. |
| 6,719,699 B2 | 4/2004 | Smith |
| 6,719,724 B1 | 4/2004 | Walker et al. |
| 6,719,756 B1 | 4/2004 | Muntermann |
| 6,720,745 B2 | 4/2004 | Lys et al. |
| 6,733,511 B2 | 5/2004 | Hall et al. |
| 6,736,782 B2 | 5/2004 | Pfeiffer et al. |
| 6,738,656 B1 | 5/2004 | Ferre et al. |
| 6,740,103 B2 | 5/2004 | Hall et al. |
| 6,743,177 B2 | 6/2004 | Ito |
| 6,746,402 B2 | 6/2004 | Ustuner |
| 6,754,596 B2 | 6/2004 | Ashe |
| 6,755,789 B2 | 6/2004 | Stringer et al. |
| 6,755,816 B2 | 6/2004 | Ritter et al. |
| 6,757,557 B1 | 6/2004 | Bladen et al. |
| 6,763,261 B2 | 7/2004 | Casscells, III et al. |
| 6,764,449 B2 | 7/2004 | Lee et al. |
| 6,768,496 B2 | 7/2004 | Bieger et al. |
| 6,772,001 B2 | 8/2004 | Maschke |
| 6,774,624 B2 | 8/2004 | Anderson et al. |
| 6,780,154 B2 | 8/2004 | Hunt et al. |
| 6,783,493 B2 | 8/2004 | Chiang et al. |
| 6,783,536 B2 | 8/2004 | Vilsmeier et al. |
| 6,784,660 B2 | 8/2004 | Ashe |
| 6,785,571 B2 | 8/2004 | Glossop |
| 6,786,219 B2 | 9/2004 | Garibaldi et al. |
| 6,788,967 B2 | 9/2004 | Ben-Haim et al. |
| 6,794,667 B2 | 9/2004 | Noshi |
| 6,799,066 B2 | 9/2004 | Steines et al. |
| 6,814,704 B2 | 11/2004 | Weilandt |
| 6,815,651 B2 | 11/2004 | Odell |
| 6,816,266 B2 | 11/2004 | Varshneya et al. |
| 6,817,364 B2 | 11/2004 | Garibaldi et al. |
| 6,832,199 B1 | 12/2004 | Kucek et al. |
| 6,834,201 B2 | 12/2004 | Gillies et al. |
| 6,844,713 B2 | 1/2005 | Steber et al. |
| 6,845,142 B2 | 1/2005 | Ohishi |
| 6,856,823 B2 | 2/2005 | Ashe |
| 6,860,422 B2 | 3/2005 | Hull et al. |
| 6,862,467 B2 | 3/2005 | Moore et al. |
| 6,869,390 B2 | 3/2005 | Elliott et al. |
| 6,869,401 B2 | 3/2005 | Gilbert et al. |
| 6,875,179 B2 | 4/2005 | Ferguson et al. |
| 6,879,160 B2 | 4/2005 | Jakab |
| 6,884,219 B1 | 4/2005 | Pruter |
| 6,889,091 B2 | 5/2005 | Hine et al. |
| 6,895,268 B1 | 5/2005 | Rahn et al. |
| 6,902,528 B1 | 6/2005 | Garibaldi et al. |
| 6,908,433 B1 | 6/2005 | Pruter |
| 6,911,026 B1 | 6/2005 | Hall et al. |
| 6,923,782 B2 | 8/2005 | O'Mahony et al. |
| 6,926,673 B2 | 8/2005 | Roberts et al. |

(56) References Cited

U.S. PATENT DOCUMENTS

| | | |
|---|---|---|
| 6,934,575 B2 | 8/2005 | Ferre et al. |
| 6,936,010 B2 | 8/2005 | Fang et al. |
| 6,940,379 B2 | 9/2005 | Creighton |
| 6,941,166 B2 | 9/2005 | MacAdam et al. |
| 6,947,788 B2 | 9/2005 | Gilboa et al. |
| 6,950,689 B1 | 9/2005 | Willis et al. |
| 6,953,754 B2 | 10/2005 | Machida et al. |
| 6,958,677 B1 | 10/2005 | Carter |
| 6,959,214 B2 | 10/2005 | Pape et al. |
| 6,962,566 B2 | 11/2005 | Quistgaard et al. |
| 6,968,846 B2 | 11/2005 | Viswanathan |
| 6,969,352 B2 | 11/2005 | Chiang et al. |
| 6,975,197 B2 | 12/2005 | Creighton, IV |
| 6,976,962 B2 | 12/2005 | Bullis |
| 6,976,987 B2 | 12/2005 | Flores |
| 6,980,843 B2 | 12/2005 | Eng et al. |
| 6,980,852 B2 | 12/2005 | Jersey-Willuhn et al. |
| 6,980,921 B2 | 12/2005 | Anderson et al. |
| 6,986,739 B2 | 1/2006 | Warren et al. |
| 6,999,821 B2 | 2/2006 | Jenney et al. |
| 7,001,355 B2 | 2/2006 | Nunomura et al. |
| 7,008,418 B2 | 3/2006 | Hall et al. |
| 7,010,338 B2 | 3/2006 | Ritter et al. |
| 7,015,393 B2 | 3/2006 | Weiner et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| D518,574 S | 4/2006 | Chaggares |
| 7,022,075 B2 | 4/2006 | Grunwald et al. |
| 7,022,082 B2 | 4/2006 | Sonek |
| 7,026,927 B2 | 4/2006 | Wright et al. |
| 7,027,634 B2 | 4/2006 | Odell |
| 7,028,387 B1 | 4/2006 | Huynh et al. |
| 7,029,446 B2 | 4/2006 | Wendelken et al. |
| 7,033,603 B2 | 4/2006 | Nelson et al. |
| D520,139 S | 5/2006 | Chaggares |
| D520,140 S | 5/2006 | Chaggares |
| 7,038,398 B1 | 5/2006 | Lys et al. |
| 7,038,657 B2 | 5/2006 | Rosenberg et al. |
| 7,043,293 B1 | 5/2006 | Baura |
| 7,054,228 B1 | 5/2006 | Hickling |
| 7,066,914 B2 | 6/2006 | Andersen |
| 7,066,924 B1 | 6/2006 | Garibaldi et al. |
| D525,363 S | 7/2006 | Chaggares |
| 7,070,565 B2 | 7/2006 | Vaezy et al. |
| 7,072,704 B2 | 7/2006 | Bucholz |
| 7,082,325 B2 | 7/2006 | Hashimshony et al. |
| 7,090,639 B2 | 8/2006 | Govari |
| 7,096,148 B2 | 8/2006 | Anderson et al. |
| 7,096,870 B2 | 8/2006 | Lamprich et al. |
| 7,098,907 B2 | 8/2006 | Houston et al. |
| 7,103,205 B2 | 9/2006 | Wang et al. |
| 7,104,980 B1 | 9/2006 | Laherty et al. |
| 7,106,043 B1 | 9/2006 | Da Silva et al. |
| 7,106,431 B2 | 9/2006 | Odell |
| 7,106,479 B2 | 9/2006 | Roy et al. |
| 7,107,105 B2 | 9/2006 | Bjorklund et al. |
| 7,132,804 B2 | 11/2006 | Lys et al. |
| 7,137,976 B2 | 11/2006 | Ritter et al. |
| 7,141,812 B2 | 11/2006 | Appleby et al. |
| 7,142,905 B2 | 11/2006 | Slayton et al. |
| 7,148,970 B2 | 12/2006 | de Boer |
| 7,153,291 B2 | 12/2006 | Bierman |
| 7,161,453 B2 | 1/2007 | Creighton, IV |
| 7,162,291 B1 | 1/2007 | Nachaliel |
| 7,167,738 B2 | 1/2007 | Schweikard et al. |
| 7,169,107 B2 | 1/2007 | Jersey-Willuhn et al. |
| 7,174,201 B2 | 2/2007 | Govari et al. |
| 7,175,646 B2 | 2/2007 | Brenneman et al. |
| 7,180,252 B2 | 2/2007 | Lys et al. |
| 7,184,820 B2 | 2/2007 | Jersey-Willuhn et al. |
| 7,189,198 B2 | 3/2007 | Harburn et al. |
| 7,190,819 B2 | 3/2007 | Viswanathan |
| 7,194,295 B2 | 3/2007 | Vilsmeier |
| 7,204,798 B2 | 4/2007 | Zdeblick et al. |
| 7,206,064 B2 | 4/2007 | Rogers et al. |
| 7,207,941 B2 | 4/2007 | Sharf |
| 7,211,082 B2 | 5/2007 | Hall et al. |
| 7,214,191 B2 | 5/2007 | Stringer et al. |
| 7,215,326 B2 | 5/2007 | Rosenberg |
| 7,221,104 B2 | 5/2007 | Lys et al. |
| 7,223,256 B2 | 5/2007 | Bierman |
| 7,229,400 B2 | 6/2007 | Elliott et al. |
| 7,231,243 B2 | 6/2007 | Tearney et al. |
| 7,236,157 B2 | 6/2007 | Schena et al. |
| 7,236,816 B2 | 6/2007 | Kumar et al. |
| 7,237,313 B2 | 7/2007 | Skujins et al. |
| 7,241,267 B2 | 7/2007 | Furia |
| 7,244,234 B2 | 7/2007 | Ridley et al. |
| 7,248,032 B1 | 7/2007 | Hular et al. |
| 7,248,914 B2 | 7/2007 | Hastings et al. |
| 7,264,584 B2 | 9/2007 | Ritter et al. |
| 7,270,662 B2 | 9/2007 | Visram et al. |
| 7,275,682 B2 | 10/2007 | Excoffier et al. |
| 7,276,044 B2 | 10/2007 | Ferry et al. |
| 7,286,034 B2 | 10/2007 | Creighton |
| 7,291,146 B2 | 11/2007 | Steinke et al. |
| 7,297,140 B2 | 11/2007 | Orlu et al. |
| 7,308,296 B2 | 12/2007 | Lys et al. |
| 7,310,150 B2 | 12/2007 | Guillermo et al. |
| 7,321,228 B2 | 1/2008 | Govari |
| 7,322,990 B1 | 1/2008 | Mark et al. |
| 7,342,058 B2 | 3/2008 | Peppmoller et al. |
| D566,284 S | 4/2008 | Kitayama et al. |
| 7,355,716 B2 | 4/2008 | de Boer et al. |
| 7,360,427 B2 | 4/2008 | Drinkwater et al. |
| 7,366,376 B2 | 4/2008 | Shishkov et al. |
| 7,366,562 B2 | 4/2008 | Dukesherer et al. |
| 7,366,563 B2 | 4/2008 | Kleen et al. |
| 7,373,271 B1 | 5/2008 | Schneider |
| 7,382,949 B2 | 6/2008 | Bouma et al. |
| 7,418,169 B2 | 8/2008 | Tearney et al. |
| 7,447,408 B2 | 11/2008 | Bouma et al. |
| 7,452,331 B1 | 11/2008 | Pruter |
| 7,452,358 B2 | 11/2008 | Stern et al. |
| D585,556 S | 1/2009 | Kosaku |
| 7,479,141 B2 | 1/2009 | Kleen et al. |
| 7,534,223 B2 | 5/2009 | Boutilette et al. |
| 7,538,859 B2 | 5/2009 | Tearney et al. |
| 7,547,282 B2 | 6/2009 | Lo et al. |
| 7,551,293 B2 | 6/2009 | Yelin et al. |
| D599,909 S | 9/2009 | Rinott et al. |
| 7,588,541 B2 | 9/2009 | Floyd et al. |
| D603,050 S | 10/2009 | Chen |
| 7,599,730 B2 | 10/2009 | Hunter et al. |
| 7,604,596 B2 | 10/2009 | Hwang et al. |
| D603,520 S | 11/2009 | Ninomiya et al. |
| 7,635,336 B1 | 12/2009 | Pruter |
| 7,637,163 B2 | 12/2009 | Fetzer et al. |
| 7,640,053 B2 | 12/2009 | Verin |
| 7,651,469 B2 | 1/2010 | Osborne et al. |
| 7,652,080 B2 | 1/2010 | Peppmoller et al. |
| D609,814 S | 2/2010 | Banryu |
| 7,665,893 B2 | 2/2010 | Buchalter |
| 7,668,583 B2 | 2/2010 | Fegert et al. |
| 7,670,294 B2 | 3/2010 | Kisen et al. |
| 7,686,766 B2 | 3/2010 | Quistgaard et al. |
| 7,691,066 B2 | 4/2010 | Kosaku |
| 7,699,782 B2 | 4/2010 | Angelsen et al. |
| 7,727,192 B2 | 6/2010 | Tokumoto et al. |
| 7,740,586 B2 | 6/2010 | Hwang et al. |
| 7,751,865 B2 | 7/2010 | Jascob et al. |
| 7,766,839 B2 | 8/2010 | Rogers et al. |
| 7,774,051 B2 | 8/2010 | Voth |
| 7,794,407 B2 | 9/2010 | Rothenberg |
| 7,798,970 B2 | 9/2010 | Lo et al. |
| 7,819,807 B2 | 10/2010 | Barnes et al. |
| 7,819,810 B2 | 10/2010 | Stringer et al. |
| 7,837,627 B1 | 11/2010 | Pruter |
| D629,526 S | 12/2010 | Ladwig et al. |
| D629,527 S | 12/2010 | Crunkilton |
| 7,846,103 B2 | 12/2010 | Cannon, Jr. et al. |
| 7,850,613 B2 | 12/2010 | Stribling |
| D630,756 S | 1/2011 | Kitayama |

(56) References Cited

U.S. PATENT DOCUMENTS

| | | | |
|---|---|---|---|
| D630,757 S | 1/2011 | Kitayama | |
| 7,909,815 B2 | 3/2011 | Whitmore, III et al. | |
| 7,931,596 B2 | 4/2011 | Rachlin et al. | |
| 7,976,469 B2 | 7/2011 | Bonde et al. | |
| 7,998,073 B2 | 8/2011 | Roth et al. | |
| 8,052,606 B2 | 11/2011 | Barnes et al. | |
| 8,073,529 B2 | 12/2011 | Cermak et al. | |
| 8,118,743 B2 | 2/2012 | Park et al. | |
| 8,137,281 B2 | 3/2012 | Huang et al. | |
| 8,147,408 B2 | 4/2012 | Bunce et al. | |
| 8,216,146 B2 | 7/2012 | Hwang et al. | |
| 8,257,264 B2 | 9/2012 | Park et al. | |
| 8,353,840 B1 | 1/2013 | Pruter | |
| 8,388,541 B2 | 3/2013 | Messerly et al. | |
| 8,388,546 B2 | 3/2013 | Rothenberg | |
| 8,430,889 B2 | 4/2013 | Zeng et al. | |
| 8,437,833 B2 | 5/2013 | Silverstein | |
| 8,449,531 B2 | 5/2013 | Whitmore, III et al. | |
| D684,265 S | 6/2013 | Cadera | |
| 8,478,382 B2 | 7/2013 | Burnside et al. | |
| 8,496,592 B2 | 7/2013 | Ridley et al. | |
| 8,496,593 B2 | 7/2013 | Park et al. | |
| 8,512,256 B2 | 8/2013 | Rothenberg | |
| 8,801,693 B2 | 8/2014 | He et al. | |
| D724,745 S | 3/2015 | Orome et al. | |
| D727,495 S | 4/2015 | Bown et al. | |
| 10,022,147 B2 | 7/2018 | Lee | |
| 10,639,008 B2 | 5/2020 | Lindekugel et al. | |
| 2001/0053915 A1 | 12/2001 | Grossman | |
| 2002/0019447 A1 | 2/2002 | Renn et al. | |
| 2002/0022777 A1 | 2/2002 | Crieghton et al. | |
| 2002/0032391 A1 | 3/2002 | McFann et al. | |
| 2002/0038088 A1 | 3/2002 | Imran et al. | |
| 2002/0055680 A1 | 5/2002 | Miele et al. | |
| 2002/0068871 A1* | 6/2002 | Mendlein | A61B 8/4209 600/459 |
| 2002/0082559 A1 | 6/2002 | Chang et al. | |
| 2002/0097926 A1 | 7/2002 | Mochizuki | |
| 2002/0113555 A1 | 8/2002 | Lys et al. | |
| 2002/0114518 A1 | 8/2002 | Wilt | |
| 2002/0120193 A1 | 8/2002 | Chiang et al. | |
| 2002/0123679 A1 | 9/2002 | Dominguez | |
| 2002/0128554 A1 | 9/2002 | Seward | |
| 2002/0133079 A1 | 9/2002 | Sandhu | |
| 2002/0151789 A1 | 10/2002 | Mansy et al. | |
| 2002/0156363 A1 | 10/2002 | Hunter et al. | |
| 2002/0156376 A1 | 10/2002 | Wang et al. | |
| 2002/0165448 A1 | 11/2002 | Ben-Haim et al. | |
| 2002/0165534 A1 | 11/2002 | Hayzelden et al. | |
| 2002/0198568 A1 | 12/2002 | Hafer et al. | |
| 2003/0002727 A1 | 1/2003 | MacMahon | |
| 2003/0009132 A1 | 1/2003 | Schwartz et al. | |
| 2003/0011359 A1 | 1/2003 | Ashe | |
| 2003/0013966 A1 | 1/2003 | Barnes et al. | |
| 2003/0018276 A1 | 1/2003 | Mansy et al. | |
| 2003/0028113 A1 | 2/2003 | Gilbert et al. | |
| 2003/0036696 A1 | 2/2003 | Willis et al. | |
| 2003/0040671 A1 | 2/2003 | Somogyi et al. | |
| 2003/0072805 A1 | 4/2003 | Miyazawa et al. | |
| 2003/0073894 A1 | 4/2003 | Chiang et al. | |
| 2003/0076281 A1 | 4/2003 | Morgan et al. | |
| 2003/0083698 A1 | 5/2003 | Whitehurst et al. | |
| 2003/0088195 A1 | 5/2003 | Vardi et al. | |
| 2003/0100849 A1 | 5/2003 | Jang | |
| 2003/0114742 A1 | 6/2003 | Lewkowicz et al. | |
| 2003/0114777 A1 | 6/2003 | Griffin et al. | |
| 2003/0120150 A1 | 6/2003 | Govari | |
| 2003/0120154 A1 | 6/2003 | Sauer et al. | |
| 2003/0139661 A1 | 7/2003 | Kimchy et al. | |
| 2003/0139664 A1 | 7/2003 | Hunt et al. | |
| 2003/0149328 A1 | 8/2003 | Elliott et al. | |
| 2003/0149359 A1* | 8/2003 | Smith | A61B 8/4281 600/437 |
| 2003/0152290 A1 | 8/2003 | Odell | |
| 2003/0158482 A1 | 8/2003 | Poland et al. | |
| 2003/0160721 A1 | 8/2003 | Gilboa et al. | |
| 2003/0163037 A1 | 8/2003 | Bladen et al. | |
| 2003/0171681 A1 | 9/2003 | Weilandt | |
| 2003/0171691 A1 | 9/2003 | Casscells et al. | |
| 2003/0173953 A1 | 9/2003 | Ashe | |
| 2003/0176787 A1 | 9/2003 | Gilbert et al. | |
| 2003/0184544 A1 | 10/2003 | Prudent | |
| 2003/0191392 A1 | 10/2003 | Haldeman | |
| 2003/0191460 A1 | 10/2003 | Hobbs et al. | |
| 2003/0195418 A1 | 10/2003 | Barnes et al. | |
| 2003/0195420 A1 | 10/2003 | Mendlein et al. | |
| 2003/0199746 A1 | 10/2003 | Fuimaono et al. | |
| 2003/0208142 A1 | 11/2003 | Boudewijn et al. | |
| 2003/0216639 A1 | 11/2003 | Gilboa et al. | |
| 2003/0220557 A1 | 11/2003 | Cleary et al. | |
| 2003/0220578 A1 | 11/2003 | Ho et al. | |
| 2003/0229298 A1 | 12/2003 | Iwami et al. | |
| 2003/0233042 A1 | 12/2003 | Ashe | |
| 2004/0015070 A1 | 1/2004 | Liang et al. | |
| 2004/0015079 A1 | 1/2004 | Berger et al. | |
| 2004/0024301 A1 | 2/2004 | Hockett et al. | |
| 2004/0030319 A1 | 2/2004 | Korkor et al. | |
| 2004/0043688 A1 | 3/2004 | Soerens et al. | |
| 2004/0054278 A1 | 3/2004 | Kimchy et al. | |
| 2004/0059226 A1 | 3/2004 | Peszynski et al. | |
| 2004/0082916 A1 | 4/2004 | Jenkins | |
| 2004/0087877 A1 | 5/2004 | Besz et al. | |
| 2004/0088136 A1 | 5/2004 | Ashe | |
| 2004/0097803 A1 | 5/2004 | Panescu | |
| 2004/0097804 A1 | 5/2004 | Sobe | |
| 2004/0097805 A1 | 5/2004 | Verard et al. | |
| 2004/0097806 A1 | 5/2004 | Hunter et al. | |
| 2004/0116809 A1 | 6/2004 | Chow et al. | |
| 2004/0127805 A1 | 7/2004 | MacAdam et al. | |
| 2004/0131998 A1 | 7/2004 | Marom et al. | |
| 2004/0133111 A1 | 7/2004 | Szczech et al. | |
| 2004/0133130 A1 | 7/2004 | Ferry et al. | |
| 2004/0135069 A1 | 7/2004 | Odell | |
| 2004/0138564 A1 | 7/2004 | Hwang et al. | |
| 2004/0138570 A1 | 7/2004 | Nita et al. | |
| 2004/0147837 A1 | 7/2004 | Macaulay et al. | |
| 2004/0150963 A1 | 8/2004 | Holmberg et al. | |
| 2004/0152972 A1 | 8/2004 | Hunter | |
| 2004/0155609 A1 | 8/2004 | Lys et al. | |
| 2004/0158140 A1 | 8/2004 | Fuimaono et al. | |
| 2004/0171924 A1 | 9/2004 | Mire et al. | |
| 2004/0176688 A1 | 9/2004 | Haldeman | |
| 2004/0186461 A1 | 9/2004 | DiMatteo | |
| 2004/0199069 A1 | 10/2004 | Connelly et al. | |
| 2004/0210289 A1 | 10/2004 | Wang et al. | |
| 2004/0230271 A1 | 11/2004 | Wang et al. | |
| 2004/0231065 A1 | 11/2004 | Daniel et al. | |
| 2004/0234453 A1 | 11/2004 | Smith | |
| 2004/0253365 A1 | 12/2004 | Warren et al. | |
| 2004/0254470 A1 | 12/2004 | Drinkwater et al. | |
| 2004/0260174 A1 | 12/2004 | Keene | |
| 2004/0267086 A1 | 12/2004 | Anstadt et al. | |
| 2005/0004450 A1 | 1/2005 | Ben-Haim et al. | |
| 2005/0021019 A1 | 1/2005 | Hashimshony et al. | |
| 2005/0033150 A1 | 2/2005 | Takahashi et al. | |
| 2005/0033177 A1 | 2/2005 | Rogers et al. | |
| 2005/0035014 A1 | 2/2005 | Cane | |
| 2005/0038355 A1 | 2/2005 | Gellman et al. | |
| 2005/0049486 A1 | 3/2005 | Urquhart et al. | |
| 2005/0049510 A1 | 3/2005 | Haldeman et al. | |
| 2005/0063194 A1 | 3/2005 | Lys et al. | |
| 2005/0070788 A1 | 3/2005 | Wilson et al. | |
| 2005/0075561 A1 | 4/2005 | Golden | |
| 2005/0085716 A1 | 4/2005 | Hamm et al. | |
| 2005/0085718 A1 | 4/2005 | Shahidi | |
| 2005/0085720 A1 | 4/2005 | Jascob et al. | |
| 2005/0101868 A1 | 5/2005 | Ridley et al. | |
| 2005/0101869 A1 | 5/2005 | Burba et al. | |
| 2005/0105081 A1 | 5/2005 | Odell | |
| 2005/0105101 A1 | 5/2005 | Duling et al. | |
| 2005/0112135 A1 | 5/2005 | Cormier et al. | |
| 2005/0113669 A1 | 5/2005 | Helfer et al. | |
| 2005/0113676 A1 | 5/2005 | Weiner et al. | |
| 2005/0113700 A1 | 5/2005 | Yanagihara et al. | |

(56) References Cited

U.S. PATENT DOCUMENTS

| | | |
|---|---|---|
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0131291 A1 | 6/2005 | Floyd et al. |
| 2005/0149002 A1 | 7/2005 | Wang et al. |
| 2005/0151489 A1 | 7/2005 | Lys et al. |
| 2005/0154308 A1 | 7/2005 | Quistgaard et al. |
| 2005/0159644 A1 | 7/2005 | Takano |
| 2005/0159790 A1 | 7/2005 | Shalev |
| 2005/0165301 A1 | 7/2005 | Smith et al. |
| 2005/0165313 A1 | 7/2005 | Byron et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182295 A1 | 8/2005 | Soper et al. |
| 2005/0203368 A1 | 9/2005 | Verin |
| 2005/0203396 A1 | 9/2005 | Angelsen et al. |
| 2005/0205081 A1 | 9/2005 | Barker et al. |
| 2005/0215901 A1 | 9/2005 | Anderson et al. |
| 2005/0215945 A1 | 9/2005 | Harris et al. |
| 2005/0222532 A1 | 10/2005 | Bertolero et al. |
| 2005/0228281 A1 | 10/2005 | Nefos |
| 2005/0240102 A1 | 10/2005 | Rachlin et al. |
| 2005/0256398 A1 | 11/2005 | Hastings et al. |
| 2005/0256541 A1 | 11/2005 | Stypulkowski |
| 2006/0015003 A1 | 1/2006 | Moaddes et al. |
| 2006/0025677 A1 | 2/2006 | Verard et al. |
| 2006/0025684 A1 | 2/2006 | Quistgaard et al. |
| 2006/0058633 A1 | 3/2006 | Hoshino et al. |
| 2006/0068074 A1 | 3/2006 | Stefandl |
| 2006/0084867 A1 | 4/2006 | Tremblay et al. |
| 2006/0116571 A1 | 6/2006 | Maschke et al. |
| 2006/0116578 A1 | 6/2006 | Grunwald et al. |
| 2006/0149134 A1 | 7/2006 | Soper et al. |
| 2006/0173329 A1 | 8/2006 | Irioka et al. |
| 2006/0173407 A1 | 8/2006 | Shaughnessy et al. |
| 2006/0176242 A1 | 8/2006 | Jaramaz et al. |
| 2006/0184074 A1 | 8/2006 | Vaezy et al. |
| 2006/0188487 A1 | 8/2006 | Thomas et al. |
| 2006/0206037 A1 | 9/2006 | Braxton |
| 2006/0211944 A1 | 9/2006 | Mauge et al. |
| 2006/0224188 A1 | 10/2006 | Libbus et al. |
| 2006/0247746 A1 | 11/2006 | Danek et al. |
| 2006/0264756 A1 | 11/2006 | Lo et al. |
| 2006/0276867 A1 | 12/2006 | Viswanathan |
| 2007/0010753 A1 | 1/2007 | MacAdam |
| 2007/0016007 A1 | 1/2007 | Govari et al. |
| 2007/0016013 A1 | 1/2007 | Camus |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0049822 A1 | 3/2007 | Bunce et al. |
| 2007/0049846 A1 | 3/2007 | Bown et al. |
| 2007/0055141 A1 | 3/2007 | Kruger et al. |
| 2007/0055142 A1 | 3/2007 | Webler |
| 2007/0060992 A1 | 3/2007 | Pappone |
| 2007/0062544 A1 | 3/2007 | Rauk Bergstrom et al. |
| 2007/0073155 A1 | 3/2007 | Park et al. |
| 2007/0087038 A1 | 4/2007 | Richardson et al. |
| 2007/0093710 A1 | 4/2007 | Maschke |
| 2007/0100285 A1 | 5/2007 | Griffin et al. |
| 2007/0112282 A1 | 5/2007 | Skujins et al. |
| 2007/0123769 A1 | 5/2007 | Fuller et al. |
| 2007/0123805 A1 | 5/2007 | Shireman et al. |
| 2007/0129770 A1 | 6/2007 | Younis |
| 2007/0135803 A1 | 6/2007 | Belson |
| 2007/0135886 A1 | 6/2007 | Maschke |
| 2007/0156205 A1 | 7/2007 | Larson et al. |
| 2007/0161904 A1 | 7/2007 | Urbano |
| 2007/0161915 A1 | 7/2007 | Desai |
| 2007/0167738 A1 | 7/2007 | Timinger et al. |
| 2007/0167801 A1 | 7/2007 | Webler et al. |
| 2007/0167808 A1 | 7/2007 | Nozaki |
| 2007/0167817 A1 | 7/2007 | Huang et al. |
| 2007/0167997 A1 | 7/2007 | Forsberg et al. |
| 2007/0197905 A1 | 8/2007 | Timinger et al. |
| 2007/0208255 A1 | 9/2007 | Ridley et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0232910 A1 | 10/2007 | Hwang et al. |
| 2007/0238984 A1 | 10/2007 | Maschke et al. |
| 2007/0239018 A1 | 10/2007 | Fetzer et al. |
| 2007/0244413 A1 | 10/2007 | Biggins |
| 2007/0247454 A1 | 10/2007 | Rahn et al. |
| 2007/0249911 A1 | 10/2007 | Simon |
| 2007/0265526 A1 | 11/2007 | Govari et al. |
| 2007/0276241 A1 | 11/2007 | Park et al. |
| 2007/0276253 A1* | 11/2007 | Park ............... A61B 17/3403 600/461 |
| 2007/0280974 A1 | 12/2007 | Son et al. |
| 2007/0282196 A1 | 12/2007 | Birk et al. |
| 2007/0282197 A1 | 12/2007 | Bill et al. |
| 2007/0299352 A1 | 12/2007 | Harlev et al. |
| 2008/0008745 A1 | 1/2008 | Stinchcomb et al. |
| 2008/0009720 A1 | 1/2008 | Schefelker et al. |
| 2008/0009743 A1 | 1/2008 | Hayasaka |
| 2008/0015442 A1 | 1/2008 | Watson et al. |
| 2008/0027320 A1 | 1/2008 | Bolorforosh et al. |
| 2008/0045908 A1 | 2/2008 | Gould et al. |
| 2008/0051626 A1 | 2/2008 | Sato et al. |
| 2008/0081958 A1 | 4/2008 | Denison et al. |
| 2008/0082136 A1 | 4/2008 | Gaudiani |
| 2008/0097232 A1 | 4/2008 | Rothenberg |
| 2008/0108949 A1 | 5/2008 | Beasley et al. |
| 2008/0110261 A1 | 5/2008 | Randall et al. |
| 2008/0110263 A1 | 5/2008 | Klessel et al. |
| 2008/0110266 A1 | 5/2008 | Randall et al. |
| 2008/0112265 A1 | 5/2008 | Urbano et al. |
| 2008/0114095 A1 | 5/2008 | Peppmoller et al. |
| 2008/0114239 A1 | 5/2008 | Randall et al. |
| 2008/0114241 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114370 A1 | 5/2008 | Schoenefeld |
| 2008/0119737 A1 | 5/2008 | Urbano et al. |
| 2008/0125772 A1 | 5/2008 | Stone et al. |
| 2008/0139944 A1 | 6/2008 | Weymer et al. |
| 2008/0146939 A1 | 6/2008 | McMorrow et al. |
| 2008/0146940 A1 | 6/2008 | Jenkins et al. |
| 2008/0152204 A1 | 6/2008 | Huo et al. |
| 2008/0154100 A1 | 6/2008 | Thalmeier et al. |
| 2008/0166453 A1 | 7/2008 | Steele et al. |
| 2008/0171934 A1 | 7/2008 | Greenan et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0188752 A1 | 8/2008 | Randall et al. |
| 2008/0200754 A1 | 8/2008 | Buchalter |
| 2008/0208060 A1 | 8/2008 | Murkin |
| 2008/0228082 A1 | 9/2008 | Scheirer et al. |
| 2008/0255404 A1 | 10/2008 | Nogawa et al. |
| 2008/0255475 A1 | 10/2008 | Kondrosky et al. |
| 2008/0275765 A1 | 11/2008 | Kuchar |
| 2008/0281206 A1 | 11/2008 | Bartlett et al. |
| 2008/0319311 A1 | 12/2008 | Hamadeh |
| 2009/0005675 A1 | 1/2009 | Grunwald et al. |
| 2009/0018497 A1 | 1/2009 | Birchard et al. |
| 2009/0018574 A1 | 1/2009 | Martin |
| 2009/0024018 A1 | 1/2009 | Boyden et al. |
| 2009/0036774 A1 | 2/2009 | Weng et al. |
| 2009/0036790 A1 | 2/2009 | Landesberg et al. |
| 2009/0043205 A1 | 2/2009 | Pelissier et al. |
| 2009/0076327 A1 | 3/2009 | Ohki |
| 2009/0082661 A1 | 3/2009 | Saladin et al. |
| 2009/0084382 A1 | 4/2009 | Jalde et al. |

(56) References Cited

U.S. PATENT DOCUMENTS

| | | |
|---|---|---|
| 2009/0101577 A1 | 4/2009 | Fulkerson et al. |
| 2009/0118612 A1 | 5/2009 | Grunwald et al. |
| 2009/0118706 A1 | 5/2009 | Schweikert et al. |
| 2009/0124901 A1 | 5/2009 | Fink et al. |
| 2009/0136099 A1 | 5/2009 | Boyden et al. |
| 2009/0143736 A1 | 6/2009 | Mittermeyer et al. |
| 2009/0149748 A1 | 6/2009 | Lenhardt et al. |
| 2009/0156926 A1 | 6/2009 | Messerly et al. |
| 2009/0163810 A1 | 6/2009 | Kanade et al. |
| 2009/0171217 A1 | 7/2009 | Kim et al. |
| 2009/0171219 A1 | 7/2009 | Uchibori |
| 2009/0177083 A1 | 7/2009 | Matsumura |
| 2009/0177090 A1 | 7/2009 | Grunwald et al. |
| 2009/0177092 A1 | 7/2009 | Riechers et al. |
| 2009/0203989 A1 | 8/2009 | Burnside et al. |
| 2009/0204113 A1 | 8/2009 | MacAdam et al. |
| 2009/0209950 A1 | 8/2009 | Starksen |
| 2009/0227952 A1 | 9/2009 | Blakstvedt et al. |
| 2009/0234328 A1 | 9/2009 | Cox et al. |
| 2009/0258171 A1 | 10/2009 | Uang |
| 2009/0259124 A1 | 10/2009 | Rothenberg |
| 2009/0262982 A1 | 10/2009 | Markowitz et al. |
| 2009/0270722 A1 | 10/2009 | Floyd et al. |
| 2009/0275828 A1 | 11/2009 | Shachar et al. |
| 2009/0275833 A1 | 11/2009 | Ikeda et al. |
| 2009/0297441 A1 | 12/2009 | Canham et al. |
| 2010/0004543 A1 | 1/2010 | Ahlund et al. |
| 2010/0004547 A1 | 1/2010 | Scholz et al. |
| 2010/0016726 A1 | 1/2010 | Meier |
| 2010/0036227 A1 | 2/2010 | Cox et al. |
| 2010/0049062 A1 | 2/2010 | Ziv |
| 2010/0055153 A1 | 3/2010 | Majmudar |
| 2010/0055184 A1 | 3/2010 | Zeitels et al. |
| 2010/0057157 A1 | 3/2010 | Govari et al. |
| 2010/0060472 A1 | 3/2010 | Kimura et al. |
| 2010/0083719 A1 | 4/2010 | Peppmoller et al. |
| 2010/0094116 A1 | 4/2010 | Silverstein |
| 2010/0106011 A1 | 4/2010 | Byrd et al. |
| 2010/0114573 A1 | 5/2010 | Huang et al. |
| 2010/0126149 A1 | 5/2010 | Kondou |
| 2010/0143119 A1 | 6/2010 | Kooijman et al. |
| 2010/0179429 A1 | 7/2010 | Ho et al. |
| 2010/0185097 A1 | 7/2010 | Hall |
| 2010/0198048 A1 | 8/2010 | Togawa |
| 2010/0204569 A1 | 8/2010 | Burnside et al. |
| 2010/0217116 A1 | 8/2010 | Eck et al. |
| 2010/0222663 A1 | 9/2010 | Wilder et al. |
| 2010/0222664 A1 | 9/2010 | Lemon et al. |
| 2010/0234733 A1 | 9/2010 | Wahlheim |
| 2010/0249598 A1 | 9/2010 | Smith et al. |
| 2010/0258033 A1 | 10/2010 | Yang et al. |
| 2010/0273895 A1 | 10/2010 | Stinchcomb et al. |
| 2010/0298702 A1 | 11/2010 | Rogers et al. |
| 2010/0312121 A1 | 12/2010 | Guan |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0015527 A1 | 1/2011 | Heasty et al. |
| 2011/0015533 A1 | 1/2011 | Cox et al. |
| 2011/0040186 A1 | 2/2011 | Matsumura |
| 2011/0040187 A1* | 2/2011 | Matsumura .......... A61B 5/6843 600/443 |
| 2011/0040212 A1 | 2/2011 | Dietz et al. |
| 2011/0052694 A1 | 3/2011 | Stinchcomb et al. |
| 2011/0060215 A1 | 3/2011 | Tupin, Jr. et al. |
| 2011/0087107 A1 | 4/2011 | Lindekugel et al. |
| 2011/0087117 A1 | 4/2011 | Tremper et al. |
| 2011/0166451 A1 | 7/2011 | Blaivas et al. |
| 2011/0171286 A1 | 7/2011 | Cecile et al. |
| 2011/0196248 A1 | 8/2011 | Grunwald |
| 2011/0202123 A1 | 8/2011 | Bonutti |
| 2011/0278500 A1 | 11/2011 | Bergeron |
| 2011/0282188 A1 | 11/2011 | Burnside et al. |
| 2011/0295108 A1 | 12/2011 | Cox et al. |
| 2011/0313293 A1 | 12/2011 | Lindekugel et al. |
| 2012/0046562 A1 | 2/2012 | Powers et al. |
| 2012/0059270 A1 | 3/2012 | Grunwald |
| 2012/0095319 A1 | 4/2012 | Kondrosky et al. |
| 2012/0108950 A1 | 5/2012 | He et al. |
| 2012/0143029 A1 | 6/2012 | Silverstein et al. |
| 2012/0165679 A1 | 6/2012 | Orome et al. |
| 2012/0220854 A1 | 8/2012 | Messerly et al. |
| 2013/0006102 A1 | 1/2013 | Wilkes et al. |
| 2013/0060116 A1 | 3/2013 | Messerly et al. |
| 2013/0085391 A1 | 4/2013 | Matsumura et al. |
| 2013/0116571 A1 | 5/2013 | Cox et al. |
| 2013/0123597 A1 | 5/2013 | Rothenberg |
| 2013/0131704 A1 | 5/2013 | Pechoux |
| 2013/0245488 A1 | 9/2013 | Quinn et al. |
| 2013/0338503 A1 | 12/2013 | Cohen et al. |
| 2014/0180116 A1 | 6/2014 | Lindekugel et al. |
| 2015/0314104 A1 | 11/2015 | Almansouri et al. |
| 2018/0289355 A1 | 10/2018 | Maracaja |
| 2020/0138409 A1 | 5/2020 | Lindekugel et al. |

FOREIGN PATENT DOCUMENTS

| | | |
|---|---|---|
| AU | 20009592 | 9/2000 |
| AU | 20015250 | 6/2001 |
| AU | 768362 B2 | 12/2003 |
| AU | 2001229024 B2 | 9/2005 |
| AU | 2001283703 B2 | 5/2006 |
| AU | 2006904933 | 9/2006 |
| AU | 2006202149 B2 | 3/2009 |
| AU | 2006283022 B2 | 2/2012 |
| CA | 2420676 C | 7/2010 |
| CN | 1175196 A | 3/1998 |
| CN | 1672649 A | 9/2005 |
| CN | 101390754 A | 3/2009 |
| CN | 102014757 A | 4/2011 |
| CN | 102209490 A | 10/2011 |
| CN | 102802514 A | 11/2012 |
| CN | 102821679 A | 12/2012 |
| CN | 103037761 A | 4/2013 |
| CN | 103037762 A | 4/2013 |
| CN | 103118591 A | 5/2013 |
| CN | 103228219 A | 7/2013 |
| CN | 106344071 A | 1/2017 |
| CN | 108135569 A | 6/2018 |
| DE | 4319033 C1 | 6/1994 |
| DE | 9404028 U1 | 8/1994 |
| EP | 0362821 A1 | 4/1990 |
| EP | 0399536 A1 | 11/1990 |
| EP | 0359697 B1 | 11/1994 |
| EP | 0815793 A2 | 1/1998 |
| EP | 0823261 A2 | 2/1998 |
| EP | 0928976 A2 | 7/1999 |
| EP | 1311226 A1 | 5/2003 |
| EP | 1504713 A1 | 2/2005 |
| EP | 2440122 A1 | 4/2012 |
| EP | 2464407 A2 | 6/2012 |
| EP | 2482719 A1 | 8/2012 |
| EP | 2575610 A1 | 4/2013 |
| EP | 2575611 A1 | 4/2013 |
| EP | 2603145 A2 | 6/2013 |
| EP | 2605699 A2 | 6/2013 |
| EP | 2313143 B1 | 9/2014 |
| FR | 2545349 B1 | 9/1986 |
| FR | 2838327 A1 | 10/2003 |
| JP | 01097440 | 4/1989 |
| JP | H02 13439 A | 1/1990 |
| JP | 03023853 A | 1/1991 |
| JP | 03173542 A | 7/1991 |
| JP | 9-503054 | 3/1997 |
| JP | 09-094298 A | 4/1997 |
| JP | 10043310 | 2/1998 |
| JP | 10290839 A | 11/1998 |
| JP | 11128237 A | 5/1999 |
| JP | 2001161683 A | 6/2001 |
| JP | 2001340334 A | 12/2001 |
| JP | 2002520893 A | 7/2002 |
| JP | 2003501127 A | 1/2003 |
| JP | 2003061752 A | 3/2003 |
| JP | 2003299654 A | 10/2003 |

(56) References Cited

FOREIGN PATENT DOCUMENTS

| | | |
|---|---|---|
| JP | 2003334191 A | 11/2003 |
| JP | 2004505748 T | 2/2004 |
| JP | 2004515298 A | 5/2004 |
| JP | 2004-313271 A | 11/2004 |
| JP | 2006508744 A | 3/2006 |
| JP | 4090741 B2 | 5/2008 |
| JP | 5010604 B2 | 8/2012 |
| JP | 2012-529929 A | 11/2012 |
| JP | 2013-518676 A | 5/2013 |
| JP | 2013-535301 A | 9/2013 |
| WO | 1991012836 A1 | 9/1991 |
| WO | 1992003090 A1 | 3/1992 |
| WO | 1994003159 A1 | 2/1994 |
| WO | 1994004938 A1 | 3/1994 |
| WO | 1996005768 A1 | 2/1996 |
| WO | 1996007352 A1 | 3/1996 |
| WO | 1996041119 A1 | 12/1996 |
| WO | 1997029683 A1 | 8/1997 |
| WO | 1997043989 A1 | 11/1997 |
| WO | 1999016495 A1 | 4/1999 |
| WO | 1999049407 A1 | 9/1999 |
| WO | 2000019906 A1 | 4/2000 |
| WO | 2000040155 A1 | 7/2000 |
| WO | 2000074775 A1 | 12/2000 |
| WO | 2001076479 A1 | 10/2001 |
| WO | 2002015973 A1 | 2/2002 |
| WO | 2002025277 A1 | 3/2002 |
| WO | 2003061752 A1 | 7/2003 |
| WO | 2003077759 A1 | 9/2003 |
| WO | 2004/006774 A2 | 1/2004 |
| WO | 2004049970 A2 | 6/2004 |
| WO | 2005033524 A1 | 4/2005 |
| WO | 2005033574 A1 | 4/2005 |
| WO | 2005117690 A1 | 12/2005 |
| WO | 2006074509 A1 | 7/2006 |
| WO | 2006074510 A1 | 7/2006 |
| WO | 2006078677 A2 | 7/2006 |
| WO | 2006103661 A2 | 10/2006 |
| WO | 2006111056 A1 | 10/2006 |
| WO | 2007002541 A2 | 1/2007 |
| WO | 2007005976 A1 | 1/2007 |
| WO | 2007014447 A1 | 2/2007 |
| WO | 2007034196 A2 | 3/2007 |
| WO | 2007067324 A1 | 6/2007 |
| WO | 2007069168 A2 | 6/2007 |
| WO | 2007109123 A2 | 9/2007 |
| WO | 2007126536 A2 | 11/2007 |
| WO | 2007144894 A1 | 12/2007 |
| WO | 2008005480 A1 | 1/2008 |
| WO | 2008/024515 A2 | 2/2008 |
| WO | 2008024596 A2 | 2/2008 |
| WO | 2008028253 A1 | 3/2008 |
| WO | 2008083111 A1 | 7/2008 |
| WO | 2008118992 A1 | 10/2008 |
| WO | 2008126074 A2 | 10/2008 |
| WO | 2008131017 A2 | 10/2008 |
| WO | 2008136008 A2 | 11/2008 |
| WO | 2009002514 A2 | 12/2008 |
| WO | 2009009064 A1 | 1/2009 |
| WO | 2009057774 A1 | 5/2009 |
| WO | 2009070616 A2 | 6/2009 |
| WO | 2009100158 A1 | 8/2009 |
| WO | 2009123819 A2 | 10/2009 |
| WO | 2009126340 A1 | 10/2009 |
| WO | 2009129475 A1 | 10/2009 |
| WO | 2009129477 A1 | 10/2009 |
| WO | 2009134605 A2 | 11/2009 |
| WO | 2009137262 A2 | 11/2009 |
| WO | 2010002313 A1 | 1/2010 |
| WO | 2010018500 A1 | 2/2010 |
| WO | 2010022370 A1 | 2/2010 |
| WO | 2010027349 A1 | 3/2010 |
| WO | 2010027471 A2 | 3/2010 |
| WO | 2010030820 A1 | 3/2010 |
| WO | 2010132857 A1 | 11/2010 |
| WO | 2010/144922 A1 | 12/2010 |
| WO | 2010143196 A1 | 12/2010 |
| WO | 2011019760 A2 | 2/2011 |
| WO | 2011041450 A1 | 4/2011 |
| WO | 2011044421 A1 | 4/2011 |
| WO | 2011051406 A1 | 5/2011 |
| WO | 2011064206 A1 | 6/2011 |
| WO | 2011084593 A2 | 7/2011 |
| WO | 2011097312 A1 | 8/2011 |
| WO | 2011128052 A2 | 10/2011 |
| WO | 2011150358 A1 | 12/2011 |
| WO | 2012021542 A2 | 2/2012 |
| WO | 2012024577 A2 | 2/2012 |
| WO | 2012058461 A1 | 5/2012 |
| WO | 2012060562 A2 | 5/2012 |
| WO | 2012083245 A1 | 6/2012 |
| WO | 2012088535 A1 | 6/2012 |
| WO | 2013006817 A1 | 1/2013 |
| WO | 2013070775 A1 | 5/2013 |
| WO | 2013188833 A2 | 12/2013 |
| WO | 2014134171 A1 | 9/2014 |

OTHER PUBLICATIONS

Schuster, M. et al., The carina as a landmark in central venous catheter placement, British Journal of Anaesthesia 85 (2): 192-4 (2000).

Rutherford, J. S. et al., Depth of Central Venous Catheterization: An Audit of Practice in a Cardiac Surgical Unit, Anaesth Intens Care 1994; 22: 267-271.

Vesely, Thomas M. et al., Central Venous Catheter Tip Position: A Continuing Controversy, J Vasc Intery Radiol 2003; 14:527-534.

Siela, Debra, Using Chest Radiography in the Intensive Care Unit, Crit Care Nurse Aug. 1, 2002 vol. 22 No. 4, pp. 18-27.

Markovich, Mary B., Central Venous Catheter Tip Placement: Determination of Posterior Malposition—A Case Study, JAVA, vol. 11, No. 2, pp. 85-89, 2006.

Bankier, Alexander A., Azygos Arch Cannulation by Central Venous Catheters: Radiographic Detection of Malposition and Subsequent Complications, Journal of Thoracic Imaging 12:64-69 (1997).

Wong, Jeffrey J. et al., Azygos Tip Placement for Hemodialysis Catheters in Patients with Superior Vena Cava Occlusion, Cardiovasc Intervent Radiol (2006) 29:143-146.

PCT/US2011/047127 filed Aug. 9, 2011 International Search Report dated Feb. 29, 2012.

PCT/US2011/047127 filed Aug. 9, 2011 Written Opinion dated Feb. 29, 2012.

Gjendemsjo, Anders, et al., Energy and Power, The Connexions Project, Version 1.2, Feb. 20, 2004.

Joosting, Jean-Pierre, "Dual-interface RFID-compatible EEPROM enables remote access to electronic device parameters," EE Times, Mar. 8, 2010.

Pop, Gheorghe A. et al., Catheter-based impedance measurements in the right atrium for continuously monitoring hematocrit and estimating blood viscosity changes; an in vivo feasibility study in swine, Biosensors and Bioelectronics 19 (2004) 1685-1693.

Konings, MK, et al., Development of an intravascular impedance catheter for detection of fatty lesions in arteries, IEEE Trans Med Imaging Aug. 1997; 16(4):439-46.

PCT/US2011/047127 filed Aug. 9, 2011 International Preliminary Report on Patentability dated Apr. 18, 2013.

U.S. Appl. No. 12/900,750, filed Oct. 8, 2010 Non-Final Office Action dated Jun. 3, 2013.

AU 2011289513 filed Jan. 21, 2013 Examiner's Report dated Jul. 5, 2013.

U.S. Appl. No. 29/428,649, filed Aug. 1, 2012 Notice of Allowance dated Jul. 5, 2013.

U.S. Appl. No. 12/900,750, filed Oct. 8, 2010 Final Office Action dated Dec. 3, 2013.

U.S. Appl. No. 13/206,396, filed Aug. 9, 2011 Non-Final Office Action dated Feb. 27, 2014.

U.S. Appl. No. 12/900,750, filed Oct. 8, 2010 Non-Final Office Action dated Apr. 10, 2014.

(56) References Cited

OTHER PUBLICATIONS

PCT/US2012/063956 filed Nov. 7, 2012 International Seach Report and Written Opinion dated Apr. 1, 2013.
Rutala, Guideline for Disinfection and Sterilization in Healthcare Facilities, 2008.
U.S. Appl. No. 13/671,382, filed Nov. 7, 2012 Non-Final Office Action dated Mar. 10, 2014.
Silindir, M. et al., "Sterilization Methods and the Comparison of E-Beam Sterilization with Gamma Radiation Sterilization," FABAD J. Pharm. Sci., 34, 43-53, 2009.
PCT/US2014/018681 filed Feb. 26, 2014 International Search Report and Written Opinion dated May 19, 2014.
PCT/US2013/045999 filed Jun. 14, 2013 International Search Report and Written Opinion dated Nov. 21, 2013.
U.S. Appl. No. 13/206,396, filed Aug. 9, 2011 Final Office Action dated Jul. 31, 2014.
U.S. Appl. No. 12/900,750, filed Oct. 8, 2010 Final Office Action dated Sep. 4, 2014.
U.S. Appl. No. 13/671,382, filed Nov. 7, 2012 Final Office Action dated Sep. 23, 2014.
CN 201180048882.3 filed Apr. 9, 2013 First Office Action dated Jun. 30, 2014.
U.S. Appl. No. 13/206,396, filed Aug. 9, 2011 Non-Final Office Action dated Dec. 16, 2014.
U.S. Appl. No. 12/900,750, filed Oct. 8, 2010 Non-Final Office Action dated Jan. 30, 2015.
U.S. Appl. No. 13/671,382, filed Nov. 7, 2012 Final Office Action dated Mar. 12, 2015.
CN 201180048882.3 filed Apr. 9, 2013 Second Office Action dated Mar. 18, 2015.
U.S. Appl. No. 13/671,382, filed Nov. 7, 2012 Advisory Action dated May 27, 2015.
U.S. Appl. No. 13/206,396, filed Aug. 9, 2011, Final Office Action dated Jun. 10, 2015.
JP 2013-524183 filed Feb. 8, 2015 First Office Action dated Jun. 24, 2015.
CN 201180048882.3 filed Apr. 9, 2013 Third Office Action dated Aug. 19, 2014.
Freeman et al. "Delta-Sigma Oversampled Ultrasound Beamformer with Dynamic Delays" IEEE Transactions on Ultrasonics, Ferroelectrics, and Frequency control, vol. 46, No. 2,—Mar. 1999.
Mucci, R. A. "A Comparison of Efficient Beamforming Algorithms" IEEE Transactions on Acoustics, Speech, and Signal Processing, vol. ASSP-32, No. 3,—Jun. 1984.
Mo et al. "Integrated analog beam former based on bucket brigade device for micromachined ultrasonic sensor array" Sensors and Actuators A 101 (2002) 203-211—Apr. 22, 2012.
Savord et al. "Fully Sampled Matrix Transducer for Real Time 3D Ultrasonic Imaging" IEEE Ultrasonics Symposium-945—2003.
Butler et al. "Practical Considerations for Analog Operation of Bucket-Brigade Circuits" IEEE Journal of Solid-State Circuits, vol. SC-8, No. 2, Apr. 1973.
Mo et al. "Pipelined Delay-Sum Architecture Based on Bucket-Brigade Devices for On-Chip Ultrasound Beamforming" IEEE Journal of Solid-State Circuits, vol. 38, No. 10, Oct. 2003.
Thomenius "Evolution of Ultrasound Beamformers" IEEE Ultrasonics Symposium 1996.
Mo et al. "Front-End Processor Using BBD Distributed Delay-Sum Architecture for Micromachined Ultrasonic Sensor Array" Journal of Microelectromechanical Systems, vol. 12, No. 4, Aug. 2003.
Tanaka el al. "Development of BBD Adding-Delay Architecture for Utrasonic Micro Array Sensor" IEEJ Trans. SM, vol. 125, No. 4 2005.
U.S. Appl. No. 12/900,750, filed Oct. 8, 2010 Final Office Action dated Oct. 19, 2015.
EP 13804474.8 filed Jan. 7, 2015 Partial European Search Report dated May 23, 2016.

Claasz, Antonia et al, A Study of the Relationship of the Superior Vena Cava to the Bony Landmarks of the Sternum in the Supine Adult: Implications for Magnetic Guidance Systems, Journal, vol. 12 No. 3, JAVA, Jul. 24, 2007.
Gebhard, et al., "The accuracy of Electrocardiogram-Controlled Central Line Placement." The International Anesthesia Research Society, vol. 104, No. 1 Jan. 2007.
McGee et al., "Accurate Placement of Central Venous Catheters: A Prospective, Randomize, Multicenter Trail." Critical Care Medicine, vol. 21 No. 8, Aug. 1993.
Corsten, et al., "Central Placement Catheter Placement Using the ECG-Guided Cavafix-Certodyn SD Catheter." Journal of Clinical Anesthesiology, vol. 6, Nov./Dec. 1994.
Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.
Cavatorta, et al., "Central Venous Catheter Placement in Hemodialysis: Evaluation of Electrocardiography Using a Guidewire." The Journal of Vascular Access, vol. 2, pp. 45-50, 2001.
Simon, et al., "Central Venous Catheter Placement in Children: Evaluation of Electrocardiography Using J-Wire." Paediatric Anaesthesia vol. 9, pp. 501-504, 1999.
David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.
Watters, et al. "Use of Electrocardiogram to Position Right Atrial Catheters During Surgery." Annals of Surgery, vol. 225, No. 2, pp. 165-171, 1997.
McDonnall, "Intra-Atrial Electrocardiography (ECG) for Catheter Placement." Literature review prepared for Bard Access Systems, Oct. 2007.
Pawlik, et al., "Central Venous Catheter Placement: Comparison of the Intravascular Guidewire and the Fluid Column Electrocardiograms." European Journal of Anaesthesiology, vol. 41, pp. 594-599, 2004.
Chu, et al., "Accurate Central Venous Port-A Catheter Placement: Intravenous Electrocardiography and Surface Landmark Techniques Compared by Using Transesophageal Echocardiography." The International Anesthesia Research Society, vol. 98, pp. 910-914, 2004.
B. Braun Website, "The Optimal Position of the Central Venous Catheter." http://www.cvcpartner.com/index.cfm18F1BDEA1310466194960A39F4E90968 (2009).
Micronix CathRite™ Cardiac Access Device Brochure. Jun. 2004.
Micronix Pty Ltd "CathRite" Guiding Styled Core Manufacturing, Jun. 15, 2006.
Guillory, "Basic Principles of Technologies for Catheter Localization." C.R. Bard internal paper, Oct. 20, 2004.
VIASYS Health Care Inc. Cortrak © Fact Sheet, 2005.
VIASYS MedSystems, Cortrak™ Systems Brochure, 2005.
Pittiruti, et al. "The EKG Method for Positioning the Tip of PICCs: Results from Two Preliminary Studies." JAVA, vol. 13, No. 4, pp. 179-185, 2008.
Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.
Clifford, et al. "Assessment of Hepatic Motion Secondary to Respiration for Computer Assisted Interventions." Computer Aided Surgery, vol. 7, pp. 291-299, 2002.
Gonzales, et al. "Peripherally Inserted Central Catheter Placement in Swine Using Magnet Detection." Journal of Intravenous Nursing, vol. 22, No. 3, May/Jun. 1999.
Sacolick, et al. "Electromagnetically Tracked Placement of a Peripherally Inserted Central Catheter." SPIE Medical Imaging, 2004 Proceedings.
Worley, Seth J. "Use of a Real-Time Three-Dimensional Magenetic Navigation System for Radiofrequency Ablation of Accessory Pathways." PACE, vol. 21 pp. 1636-1643, Aug. 1998.
Aurora® System Technical Specifications, Oct. 2003.
Stereotaxis Magetic Navigation System with Navigant™ User Interface, 2005 Brochure.

(56) References Cited

OTHER PUBLICATIONS

Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.
Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300, May 1990.
Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.
Neurometer® CPT, Products Page. Neurotron, Inc. website: www.neurotron.com/products.html, last accessed Oct. 23, 2006.
Neurometer® CPT, Frequently Asked Questions. Neurotron, Inc. website: www.neurotron.com/CPTFAQ/html, last accessed Oct. 23, 2006.
Neurometer® Electrodiagnostic Neuroselective Sensory Nerve Evaluation: Charts, Tables, Documents & Downloads. Neurotron, Inc. website: www.neurotron.com/downloads.html, last accessed Oct. 23, 2006.
Neurometer® CPT, Clinical Applications. Neurotron, Inc. website: www.neurotron.com/CLINAPS.html, last accessed Oct. 23, 2006.
Microbird™ Miniaturized DC Magnetic Sensors for Intra-body Navigation and Localization, Specifications, 2005.
"Ascension to Launch New 3D Guidance™ Tracker at TCT 2006." Press Releases from Ascension website: www.ascension-tech.com/news/press_101106.php, last accessed Dec. 1, 2006.
Deltec Cath-Finder® Tracking System Operation Manual, 1994.
Traxal Technologies, Tracking Technology website overview: www.traxal.com/rd/rd_classroom_trackingtechnology.htm, last accessed Dec. 1, 2006.
Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.
Schummer, et al. "Central Venous Catheters—The inability of 'intra-atrial ECG' to prove adequate positioning." British Journal of Anaesthesia, vol. 93, No. 2, pp. 193-198, 2004.
Aslamy, et al. "MRI of Central Venous Anatomy: Implications for Central Venous Catheter Insertion." American College of Chest Physicians, Jun. 8, 2009.
Schafer et al. "Incorrect placement of a vena cava catheter and its prevention by intra-atrial ECG." Anaesthesist. Jan. 1988;37(1):49-51.
Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.
Arrow International, Inc., The Arrow-Johans RAECG Adapter-Making Proper Central Venous Catheter Placement More Reliable (Modle No. EG-04900), Technical Report 1987, USA.
B. Braun, Certofix Central Venous Catheter for Placement Using the Seldinger Technique with Simultaneous ECG Lead Option, Feb. 2010.
C.R. Bard, Inc., Bard Electrophysiology Product Catalogue, Bard Catheters, pp. 74-75 (2002), USA.
Wilson, R. G. et al, Right Atrial Electrocardiogram Placement of Central Venous Catheters, The Lancet, pp. 462-463, Feb. 27, 1988.
Michenfelder, John et al, Air Embolism During Neurosurgery. A New Method of Treatment, Anesthesia and Analgesia. Current Researches, pp. 390-395, vol. 45, No. 4, Jul.-Aug. 1966.
Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.
UAB Health Systems, Arrhythmias, retrieved from http://www.health,uab.edu/14564/ on Nov. 15, 2007, 12 pages.

Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.
Bailey, SH et al, Is Immediate Chest Radiograph Necessary after Central Venous Catheter Placement in a Surgical Intensive Care Unit?, Am J Surg, pp. 517-522, vol. 180 No. 6, Dec. 2000.
Petersen, J et al, Silicone Venous Access Devices Positioned with their Tip High in the Superior Vena Cava are More Likely to Malfunction, Am J Surg, pp. 38-41, vol. 178 No. 1, Jul. 1999.
Cadman, A et al, To Clot or Not to Clot? That is the question in Central Venous Catheters, Clinical Radiology, pp. 349-355, vol. 59 No. 4, Apr. 2004.
Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.
Reynolds, N et al, Assessment of Distal Tip Position of Long Term Central Venous Feeding Catheters using Transesophageal Echocardiology, JPEN J Parenter Enteral Nutr, pp. 39-41, vol. 25 No. 1, Jan.-Feb. 2001.
Kowalski, CM et al, Migration of Central Venous Catheters: Implications for Initial Catheter Tip Positioning, J Vasc Interv Radiol, pp. 443-447, vol. 8 No. 3, May-Jun. 1997.
Odd, De et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.
Stark, DD et al, Radiographic Assessment of Venous Catheter Position in Children: Value of the Lateral View, Pediatric Radiology, pp. 76-80, vol. 14 No. 2, 1984.
Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.
Nazarian, GK et al, Changes in Tunneled Catheter Tip Position when a patient is Upright, J Vasc Interv Radiol, pp. 437-441, vol. 8 No. 3, May-Jun. 1997.
Frassinelli, P et al, Utility of Chest Radiographs after Guidewire Exchanges of Central Venous Catheters, Crit Care Med, pp. 611-615, vol. 26 No. 3, Mar. 1998.
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Palesty, JA et al, Routine Chest Radiographs Following Central Venous Recatherization over a Wire are not Justified, Am J Surg, pp. 618-621, vol. 176 No. 6, Dec. 1998.
Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.
Reece, A et al, Posititioning Long Lines: Contrast Versus Plain Radiography, Arch Dis Child Fetal Neonatal Ed, pp. 129-130, vol. 84 No. 2, Mar. 2001.
Forauer, AR et al, Change in Peripherally Inserted Central Catheter Tip Location with Abduction and Adduction of the Upper Extremity, J Vasc Interv Radiol, pp. 1315-1318, vol. 11 No. 10, Nov.-Dec. 2000.
Collier, PE et al, Cardiac Tamponade from Central Venous Catheters, Am J Surg, pp. 212-214, vol. 176 No. 2, Aug. 1998.
Barber, JM et al, A Nurse led Peripherally Inserted Central Catheter Line Insertion Service is Effective with Radiological Support, Clin Radiol, pp. 352-354, vol. 57 No. 5, May 2002.
Nadroo, AM et al, Changes in Upper Extremity Position Cause Migration of Peripherally Inserted Central Catheters in Neonates, Pediatrics, pp. 131-136, vol. 110, Jul. 2002.
Nakatani, K et al, Accurate Placement of Central Venous Catheters—ECG-guided method vs Patient Height Method, Masui, pp. 34-38, vol. 51 No. 1, Jan. 2002.
Arai, J et al, Detection of Peripherally Inserted Central Catheter Occlusion by in-line Pressure Monitoring, Paediatr Anaesth, pp. 621-624, vol. 12 No. 7, Sep. 2002.
Leowenthal, MR et al, The Peripherally Inserted Central Catheter (PICC): A Prospective Study of its Natural History after Fossa Insertion, Anaesth Intensive Care, pp. 21-24; vol. 30 No. 1, Feb. 2002.

(56) References Cited

OTHER PUBLICATIONS

Kim, Ko et al, Positioning Internal Jugular Venous Catheters using the Right Third Intercostal Space in Children, Acta Anaesthesiol Scand, pp. 1284-1286, vol. 47 No. 10, Nov. 2003.

Yoon, SZ et al, Usefulness of the Carina as a Radiographic Landmark for Central Venous Catheter Placement in Paediatric Patients, Br J Anaesth, Jul. 2005.

Cullinane, DC et al, The Futility of Chest Roentgenograms Following Routine Central Venous Line Changes, Am J Surg, pp. 283-285, vol. 176 No. 3, Sep. 1998.

Schummer, W, Central Venous Catheter—the Inability of "Intra-Atrial ECG" to prove Adequate Positioning, Br J Anaesth, pp. 193-198, vol. 93 No. 2, Aug. 2004.

Lynch, RE et al, A Procedure for Placing Pediatric Femoral Venous Catheter Tips near the Right Atrium, Pediatr Emerg Care, pp. 130-132, vol. 18 No. 2, Apr. 2002.

Carlon, R et al, Secondary Migration of a Central Venous Catheter—A Case Report, Minerva Anestesiol, pp. 927-931, vol. 69 No. 12, Dec. 2003.

Felleiter P et al, Use of Electrocardiographic Placement Control of Central Venous Catheters in Austria, Acta Med Austriaca, pp. 109-113, vol. 26 No. 3, 1999 (Abstract only).

Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).

Engelhardt, W et al, ECG-Controlled Placement of Central Venous Catheters in Patients with Atrial Fibrillation, Anaesthesist, pp. 476-479, vol. 38 No. 9, Sep. 1989 (Abstract only).

Kjelstrup T et al, Positioning of Central Venous Catheters using ECG, Tidssk Nor Laegeforen, pp. 599-601, vol. 111 No. 5, Feb. 1999 (Abstract only).

Cheng, KI et al, A Novel Approach of Intravenous Electrocardiographic Technique in Correct Position the Long-Term Central Venous Catheter, Kaohsiung J Med Sci, pp. 241-247, vol. 16 No. 5, May 2000 (Abstract only).

Gebauer, B et al, Ultrasound and Fluoroscopy-guided Implantation of Peripherally Inserted Central Venous Catheters (PICCs), ROFO, pp. 386-391, vol. 176 No. 3, Mar. 2004 (Abstract only).

Polos, P et al, Tips for Monitoring the Position of a Central Venous Catheter—How Placement can go awry—even when the anatomy is normal, J Crit Illn, pp. 660-674, vol. 8 No. 6, Jun. 1993 (Abstract only).

Yilmazlar A et al, Complications of 1303 Central Venous Cannulations, J R Soc Med, pp. 319-321, vol. 90 No. 6, Jun. 1997 (Abstract only).

Guth, AA, Routine Chest X-rays after Insertion of Implantable Long-Term Venous Catheters: Necessary or Not?, Am Surg, pp. 26-29, vol. 67 No. 1, Jan. 2001 (Abstract only).

Murthy, Vrudhula et al, Analysis of Power Spectral Densities of Electrocardiograms, Mathematical Biosciences, pp. 41-51, vol. 12 No. 1-2, Oct. 1971.

Yoshida, Teruhisa et al, Detection of Concealed Left Sided Accessory Atrioventricular Pathway by P Wave Signal Averaged Electrocardiogram, J Am Coll Cardiol, pp. 55-62, Jul. 1999.

Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.

Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.

Smith, Brigham, et al., Intravenous electrocardiographic guidance for placement of peripherally inserted central catheters, Journal of Electrocardiology 43 (2010) 274-278.

Valdivieso, J.R. Perez, et al., Evaluation of a formula for optimal positioning of a central venous catheter inserted through the right internal jugular vein, Rev. Esp. Anestesiol. Reanim. 2003; 50: 77-79.

Curet, Myriam J. et al., University and Practice-based Physicians' Input on the Content of a Surgical Curriculum, The American Journal of Surgery® vol. 178 Jul. 1999, 78-84.

Cheung, P., et al., The Effect of a Disposable Probe Cover on Pulse Oximetry, Anaesth Intensive Care 2002; 30: 211-214.

Kofler, Julia, et al., Epinephrine application via an endotracheal airway and via the Combitube in esophageal position, Critical Care Medicine: May 2000, vol. 28: Issue 5, pp. 1445-1449.

Zachariou, Zacharias et al., Intra-atrial ECG recording: a new and safe method for implantation of Broviac catheters in children, Pediatr Surg Int (1994) 9: 457-458.

Lum, Phillip, A New Formula-Based Measurement Guide for Optimal Positioning of Central Venous Catheters, JAVA, vol. 9, No. 2, pp. 80-85, 2004.

Cardella, John F. et al., Interventinal Radiologic Placement of Peripherally Inserted Central Catheters, Journal of Vascular and Interventional Radiology 1993; 4:653-660.

Chang, Thomas C. et al., Are Routine Ch Ladiographs Necessary After Image-Guided Placement of Internal Jugular Central Venous Access Devices?, AJR Feb. 1998;170:335-337.

U.S. Appl. No. 13/918,707, filed Jun. 14, 2013 Non-Final Office Action dated May 9, 2016.

EP 13804474.8 filed Jan. 7, 2015 Extended European Search Report dated Aug. 31, 2016.

EP 14756632.7 filed Aug. 24, 2015 Partial European Search Report dated Sep. 30, 2016.

U.S. Appl. No. 13/918,707, filed Jun. 14, 2013 Final Office Action dated Nov. 18, 2016.

EP 14756632.7 filed Aug. 24, 2015 Extended European Search Report dated Sep. 30, 2016.

U.S. Appl. No. 12/900,750, filed Oct. 8, 2010 Non-Final Office Action dated Jan. 26, 2017.

CN 201380031663.3 filed Dec. 15, 2014 Office Action dated Jun. 1, 2016.

CN 201380031663.3 filed Dec. 15, 2014 Office Action dated Jan. 19, 2017.

CN 201480010486.5 filed Aug. 25, 2015 Office Action dated Feb. 28, 2017.

U.S. Appl. No. 14/190,591, filed Feb. 26, 2014 Non-Final Office Action dated May 17, 2017.

U.S. Appl. No. 13/206,396, filed Aug. 9, 2011, Non-Final Office Action dated May 26, 2017.

U.S. Appl. No. 13/918,707, filed Jun. 14, 2013 Non-Final Office Action dated Jul. 3, 2017.

U.S. Appl. No. 12/900,750, filed Oct. 8, 2010 Final Office Action dated Aug. 4, 2017.

CN 201380031663.3 filed Dec. 15, 2014 Office Action dated Jul. 12, 2017.

U.S. Appl. No. 14/190,591, filed Feb. 26, 2014 Final Office Action dated Oct. 30, 2017.

CN 201480010486.5 filed Aug. 25, 2015 Office Action dated Nov. 16, 2017.

CN 201380031663.3 filed Dec. 15, 2014 Office Action dated Dec. 21, 2017.

U.S. Appl. No. 13/206,396, filed Aug. 9, 2011, Final Office Action dated Jan. 25, 2018.

U.S. Appl. No. 13/918,707, filed Jun. 14, 2013 Final Office Action dated Apr. 16, 2018.

U.S. Appl. No. 14/190,591, filed Feb. 26, 2014 Non-Final Office Action dated Apr. 19, 2018.

CN 201480010486.5 filed Aug. 25, 2015 Office Action dated Jun. 13, 2018.

U.S. Appl. No. 13/206,396, filed Aug. 9, 2011 Advisory Action dated Jul. 27, 2018.

U.S. Appl. No. 14/190,591, filed Feb. 26, 2014 Examiner's Answer dated Sep. 11, 2018.

U.S. Appl. No. 13/206,396, filed Aug. 9, 2011 Advisory Action dated Oct. 10, 2018.

U.S. Appl. No. 12/900,750, filed Oct. 8, 2010 Examiner's Answer dated Oct. 23, 2018.

U.S. Appl. No. 13/918,707, filed Jun. 14, 2013 Examiner's Answer dated Jan. 25, 2019.

(56) References Cited

OTHER PUBLICATIONS

U.S. Appl. No. 13/206,396, filed Aug. 9, 2011 Non-Final Office Action dated Mar. 19, 2019.
U.S. Appl. No. 12/900,750, filed Oct. 8, 2010 Non-Final Office Action dated Jun. 27, 2019.
U.S. Appl. No. 14/190,591, filed Feb. 26, 2014 Board Decision dated Oct. 17, 2019.
U.S. Appl. No. 13/206,396, filed Aug. 9, 2011 Final Office Action dated Oct. 18, 2019.
U.S. Appl. No. 13/206,396, filed Aug. 9, 2011 Notice of Allowance dated Dec. 30, 2019.
U.S. Appl. No. 12/900,750, filed Oct. 8, 2010 Final Office Action dated Jan. 9, 2020.
U.S. Appl. No. 12/900,750, filed Oct. 8, 2010 Advisory Action dated Apr. 9, 2020.
Pennington, C.R., Right Atrial Thrombus: a Complication of Total Parenteral Nutrition, British Medical Journal, pp. 446-447, vol. 295, Aug. 15, 1987.
Greenall, M.J. et al, Cardiac Tamponade and Central Venous Catheters, British Medical Journal, pp. 595-597, Jun. 14, 1975.
Colley, Peter S et al, ECG-Guided Placement of Sorenson CVP Catheters via Arm Veins, Anesthesia and Analgesia, pp. 953-956, vol. 63, 1984.
Stereotaxis, Expanding the Possibilites of Interventional Medicine: Remote Navigation and Automation, pp. 1-8, Apr. 2011.
Bard Access Systems, Sherlock Tip Location System, 5 pages, 2006.
Bard Access Systems, Site Rite Vascular Acess Ultrasound System, 4 pages, 2005.
Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.
Stas, M et al, Peroperative Intravasal Electrographic Control of Catheter Tip Position in Access Ports Placed by Venous Cut-Down Technique, EJSO, pp. 316-320, vol. 27, 2001.
Hill, Bradley, Identifying the Caval-Atrial Junction Using Smart-Catheter Technology presentation, 22nd Annual Scientific Meeting of the AVA in Savannah, Georgia, Sep. 13, 2008.
Acuson—The Value of Vision, AcuNav Diagnostic Ultrasound Catheter, 2000.
C.R. Bard, CathTrack™ Catheter Location System at www.bardaccess.com <http://www.bardaccess.com>, last accessed Apr. 28, 2011.
Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.
Gladwin, MT et al, Cannulation of the Internal Jugular Vein: is postpocedural chest radiography always necessary?, Crit Care Med, 33 pages, Oct. 2000.
Volcano ComboMap Features and Benefits/Technical Specifications, 2 pages, 2011.
ComboWire® Pressure/Flow Guide Wire Ref 9500 Series, Instructions for Use, Apr. 2011.
Starr, David S et al, EKG Guided Placement of Subclavian CVP Catheters Using J-Wire, pp. 673-676, Ann. Surg, Dec. 1986.
Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.
Frazin L et al, A Doppler Guided Retrograde Catheterization System, Cathet. Cardiovasc Diagn, pp. 41-50, May 1992.
Tepa® Health Innovation PC based ECG System Introduction and Technical Specifications, EKG Master USB, 2 pages, Nov. 2003.
The FloWire Doppler Guide Wire located <http://www.volcanocorp.com/products/flowire-doppler-guide-wire.php>, 2011.

Advertising flyer for GAVECELT—The Italian Group for Long Term Venous Access Devices, for program on International Meeting on PICC's, Midline Catheters and Long Term Venous Access Devices in Catholic University, Rome, Italy on Dec. 3, 4, 5, 2008.
Liu, Ji-Bin et al, Catheter-Based Intralumincal Sonography, J Ultrasound Med, pp. 145-160, vol. 23, 2004.
Paliotti, Roberta P. et al, Intravascular Doppler Technique for Monitoring Renal Venous Blood Flow in Man, J Nephrol, pp. 57-62, 2003.
BioAdvance Lumen Vu, Greenhouse Fund Feb. 2004 Recipient, www.bioadvance.com <http://www.bioadvance.com>, 2005.
MedGraphics, CardioPerfect® Resting/Stress ECG System, 3 pages, 2001.
Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.
Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.
Caruso, LJ et al, A Better Landmark for Positioning a Central Venous Catheter, J Clinical Monitoring and Computing, pp. 331-334, vol. 17 No. 6, Aug. 2002.
Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, Chest, 2003.
Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.
Ruschulte, Heiner et al, Prevention of Central Venous Catheter related infections with chlorhex idine gluconate impregnated wound dressings: A randomized controlled trial, presented as an abstract at the Annual meeting of the European Society of Anaesthesiologists (ESA) in Madrid, Spain in Jun. 2006, 12 pages, Annals of Hematology, Jul. 14, 2008.
French, PJ et al, Sensors for Catheter Applications, Sensors Update, vol. 13 Issue 1 pp. 107-153, Dec. 2003.
Allan, P.L. et al, Role of Ultrsound in the Assessment of Chronic Venous Insufficiency, Ultrasound Quarterly, vol. 17, No. 1, pp. 3-10, 2001.
Fearon, William F et al, Evaluating Intermediate Coronary Lesions in the Cardiac Catheterization Laboratory, vol. 4, No. 1, 7 pages, Reviews in Cardiovascular Medicine, 2003.
VasoNova Inc, Vascular navigation system for accurate placement of PICCs, Start-Up Emerging Medical Ventures, pp. 44-45, vol. 14 No. 7, Jul.-Aug. 2009.
Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.
VIASYS Healthcare MedSystems, Navigator® Benefits, 2008.
VIASYS Healthcare MedSystems, Navigator® Research in Cost Justification, 2008.
Buehrle, Douglas, PICC Placement in Humans using Electromagnetic Detection, <http://www.corpakmedsystems.com/supplement_material/supplementpages/navigator/navarticle.html>, 2008.
Welch Allyn Cardioperfect® PC-Based Resting ECG, 2003.
Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
Randolph AG et al, Ultrasound guidance for placement of central venous catheters: a meta-analysis of the literature, Critcal Care Medicine, pp. 2053-2058, vol. 24, Dec. 1996.
Savary, D et al, Intra-atrial Monitoring to Add Insertion of a Central Venous Line in Pre-Hospital Emergency Care Journal Europeen des Urgences, pp. 75-78, vol. 17 No. 2, 2004.

(56) References Cited

OTHER PUBLICATIONS

Hill, Bradley et al, Abstract of article discussing VasaNova VPS as guide for placement of PICCs. 2009.
Calvert, N et al. The Effectiveness and Cost-effectiveness of Ultrasound Locating Devices for Central Venous Access: A Systematic Review and Economic Evaluation, Health Technology Assessment, vol. 7, No. 12, 2003.
Pittiruti, et al, Intracavitary EKG Monitoring: A reliable method for controlling tip position during and after PICC Insertion presentation in Catholic University, Rome, Italy in 2008.
Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.
PCT/US2010/051917 filed Oct. 8, 2010 Search Report dated Nov. 29, 2010.
PCT/US2010/051917 filed Oct. 8, 2010 Written Opinion dated Nov. 29, 2010.
U.S. Appl. No. 12/900,750, filed Oct. 8, 2010 Notice of Allowance dated Apr. 26, 2021.
U.S. Appl. No. 16/709,664, filed Dec. 10, 2019 Final Office Action dated May 25, 2021.
U.S. Appl. No. 12/900,750, filed Oct. 8, 2010 Advisory Action dated Nov. 3, 2020.
U.S. Appl. No. 12/900,750, filed Oct. 8, 2010 Final Office Action dated Aug. 21, 2020.
U.S. Appl. No. 13/918,707, filed Jun. 14, 2013 Notice of Allowance dated Jun. 18, 2020.
U.S. Appl. No. 16/709,664, filed Dec. 10, 2019 Non-Final Office Action dated Dec. 14, 2020.
U.S. Appl. No. 16/709,664, filed Dec. 10, 2019 Non-Final Office Action dated Jun. 24, 2020.

* cited by examiner

SUPPORT AND COVER STRUCTURES FOR AN ULTRASOUND PROBE HEAD

CROSS-REFERENCE TO RELATED APPLICATIONS

This application is a continuation of U.S. patent application Ser. No. 13/206,396, filed Aug. 9, 2011, now U.S. Pat. No. 10,639,008, which is a continuation-in-part of U.S. application Ser. No. 12/900,750, filed Oct. 8, 2010, now U.S. Pat. No. 11,103,213, which claims the benefit of U.S. Provisional Application No. 61/372,044, filed Aug. 9, 2010, and of U.S. Provisional Application No. 61/249,850, filed Oct. 8, 2009, each of which incorporated herein by reference in its entirety.

BRIEF SUMMARY

Briefly summarized, embodiments of the present invention are directed to a probe cap for use with an ultrasound probe including a head portion and an acoustic surface. In one embodiment, the probe cap includes a body that defines a cavity sized for releasably receiving the head portion of the probe therein. The probe cap body further defines a hole that is proximate the acoustic surface of the head portion. A compliant spacer component is disposed in the hole. The spacer component can include a hydrogel and provides an acoustic path between the acoustic surface and a tissue surface of a patient. The spacer component further includes a skin contact surface that defines a concavity and is deformable against the skin. The skin contact surface can further define one or more spacer elements adjacent the concavity for distributing the load of the probe pressing against the skin and preventing compression of subcutaneous structures of the patient.

In another embodiment, an ultrasound imaging system for imaging a subcutaneous structure of a patient is disclosed and includes a display, an ultrasound probe including an acoustic surface from which ultrasound signals are emitted, and first and second spacer elements. The spacer elements are positioned proximate opposite ends of the acoustic surface and are configured to provide a gap between the acoustic surface and a tissue surface of the patient. So configured, the spacer elements prevent compression of the subcutaneous structure of the patient.

In addition, embodiments to be further described below disclose various probe cap and accompanying needle guide designs for use in assisting a clinician with ultrasound probe use and needle insertion into a patient.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to various components for spacing an acoustic surface of an ultrasound probe from a tissue surface of a patient during ultrasound procedures to image subcutaneous tissues of the patient. Such ultrasound procedures are employed, for instance, in connection with the placement of a catheter within a vessel of the patient. As will be described, the components for spacing the acoustic surface in one embodiment prevent undesired compression of subcutaneous vessels, especially superficial vessels, which in turn improves the imaging of such vessels by the probe. In addition, embodiments to be described further below disclose various probe cap and accompanying needle guide designs for use in assisting a clinician with ultrasound probe use and needle insertion into a patient.

Figure 1A:
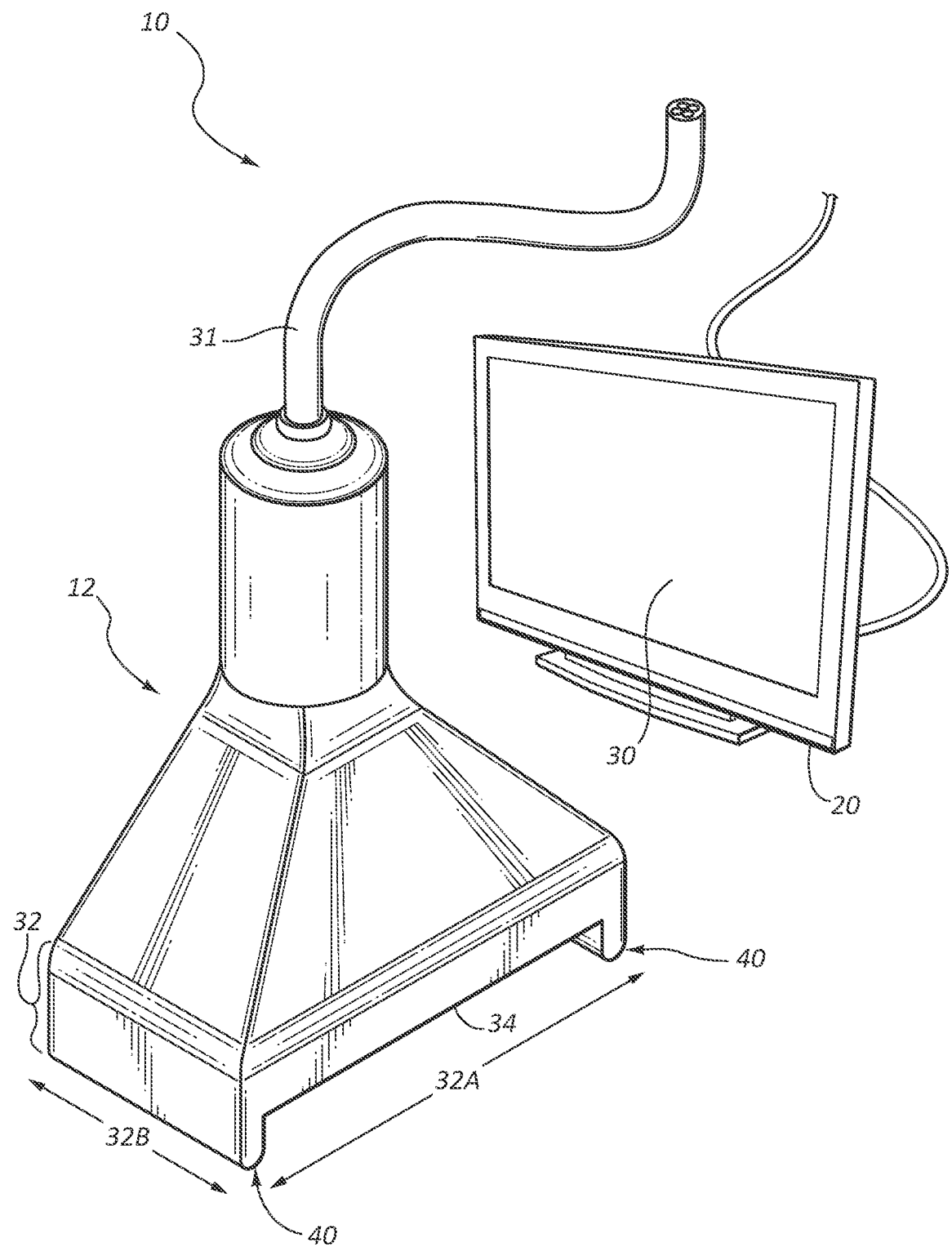
FIGS. 1A and 1B are perspective and side views, respectively, of an ultrasound probe including spacer elements configured in accordance with one embodiment.
Figure 1B:
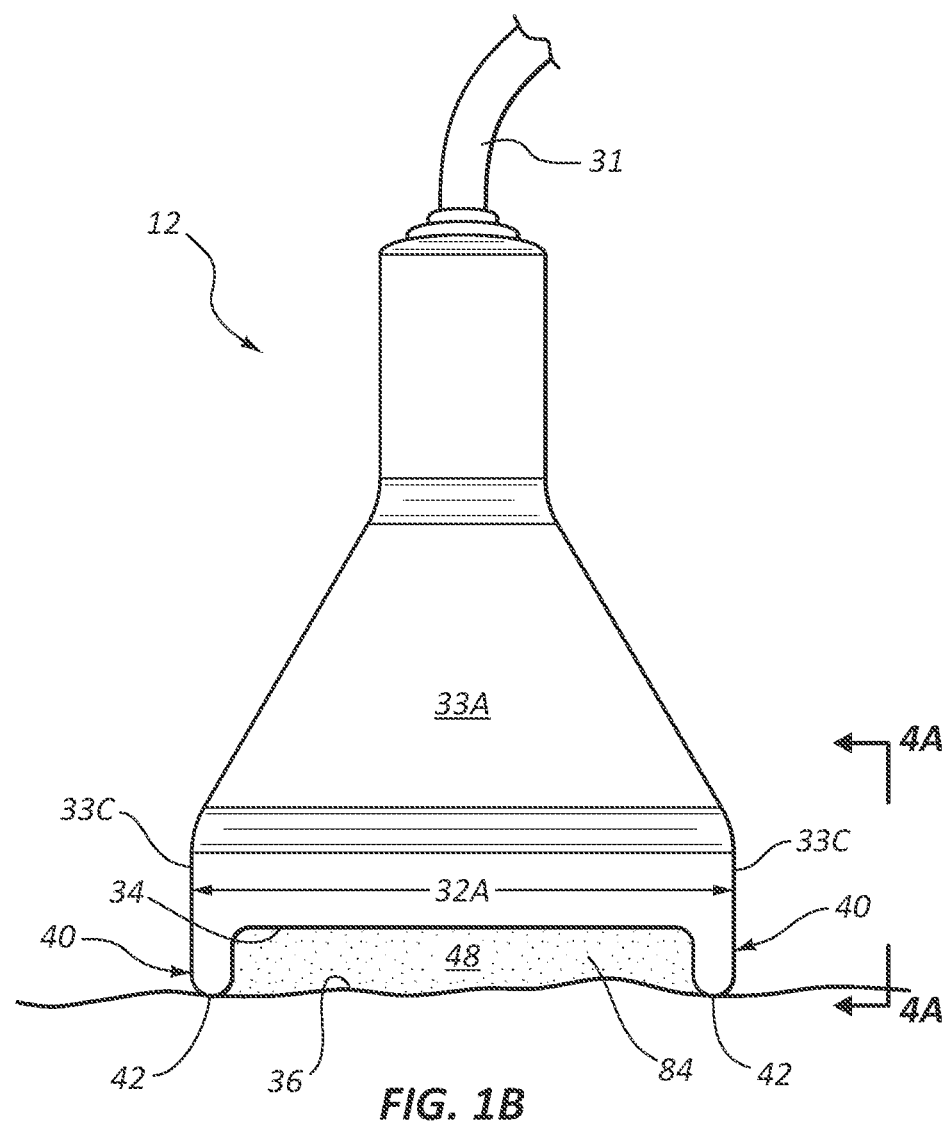

Reference is first made to FIGS. 1A and 1B, which depict an ultrasound imaging system 10 according to one embodiment, including an ultrasound probe 12 and a console 20 including a display 30 for depicting an image produced by the probe. In the present embodiment, the probe 12 is operably connected to the console 20 via a cable 31, though in one embodiment the probe can be wirelessly connected thereto.

The probe 12 includes a head 32 defined by a longitudinal length 32A and a width 32B. The body of the probe generally defines a front face 33A, a rear face 33B, and side faces 33C. It should be appreciated that the preceding description of the probe is not meant to limit application of the principles described herein in any way. The probe head 32 includes an acoustic surface 34 extending along at least a portion of a longitudinal length 32A of the probe head from which ultrasonic impulses are emitted in order to penetrate and image subcutaneous portions of the patient. Note that the size, shape and configuration of both the probe and acoustic surface can vary from what is described herein while still residing within the principles of the present disclosure. Note also that FIG. 1A shows just one example of an ultrasound imaging system; other systems including other components can also benefit from the principles described herein.

As depicted in FIGS. 1A and 1B, in accordance with one embodiment the probe head 32 includes two spacer elements, generally depicted at 40, disposed adjacent the probe acoustic surface 34 at each end of the longitudinal length 32A. Each spacer element 40 acts as an extended surface to provide a gap 48 between the acoustic surface 34 and the skin 36 or other tissue surface of the patient, as further described below, when the probe 12 is placed on the patient's skin for use in subcutaneous imaging.

In greater detail, each spacer element 40 in the present embodiment defines a blade-like extended surface that includes a contact surface 42 for contacting the tissue/skin 36 of the patient. The contact surface 42 can be shaped in one of several configurations, as will be discussed further below.

Figure 2:
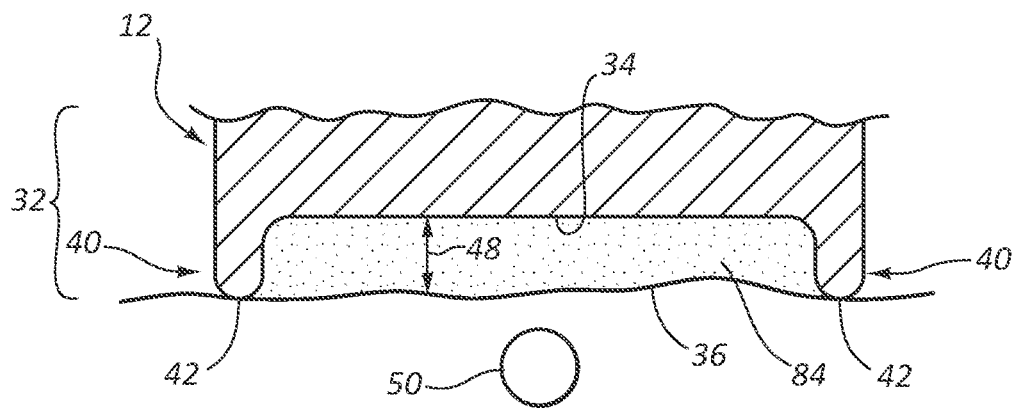
FIG. 2 is a simplified cross-sectional view of the ultrasound probe of FIGS. 1A and 1B used to image a vessel of a patient.

Reference is now made to FIG. 2. When no spacers are present on an ultrasound probe, the acoustic surface thereof directly contacts the patient's skin during imaging, which can cause a downward pressure sufficient to undesirably compress a subcutaneous vessel disposed beneath the probe. Further, the proximity of the probe acoustic surface to the patient's skin can cause the focal point of the probe to reside below the vessel to be imaged, resulting in less than optimal image resolution of superficial vessels or other objects residing relatively close to the skin surface.

In contrast to the above, FIG. 2 shows the probe 12 including the spacer elements 40 disposed at each longitudinal end of the probe head 32 and adjacent the acoustic surface 34. So configured, the acoustic surface 34 is spaced apart from the patient's skin 36 during probe use, and only the contact surfaces 42 of the spacer elements 40 are in contact therewith. The gap 48 is thus defined between the acoustic surface 34 and the patient's skin 36, which can be filled with an ultrasonic gel 84 or other acoustically transparent substance to improve imaging, in one embodiment.

Because the acoustic surface 34 of the ultrasound probe head 32 is not in direct contact with the patient's skin 36 during probe use, pressure on the skin imposed by the acoustic surface is avoided, which in turn prevents a vessel 50 underneath the probe 12 from being compressed by the probe during use. Instead, any downward force provided by the probe 12 is directed through the spacer elements 40. As such, the vessel 50 below the acoustic surface 34 remains patent and can be accurately imaged. Further, the increased distance between the acoustic surface 34 and the patient's skin 36 provided by the gap 48 moves the focal spot of the probe 12 to a location relatively close below the skin surface, which enables superficial vessels and other objects residing near the skin surface to be brought more closely to the focal point of the probe and be sharply imaged.

Note that the gap 48 shown in FIGS. 1A-2 is bounded during probe use by the acoustic surface 34, the skin 36, and the spacer elements 40. As such, the gap 48 remains open below the front and rear faces 33A, 33B of the probe 12. Note that additional spacers could be employed to further define the gap 48, if desired.

Figure 3:
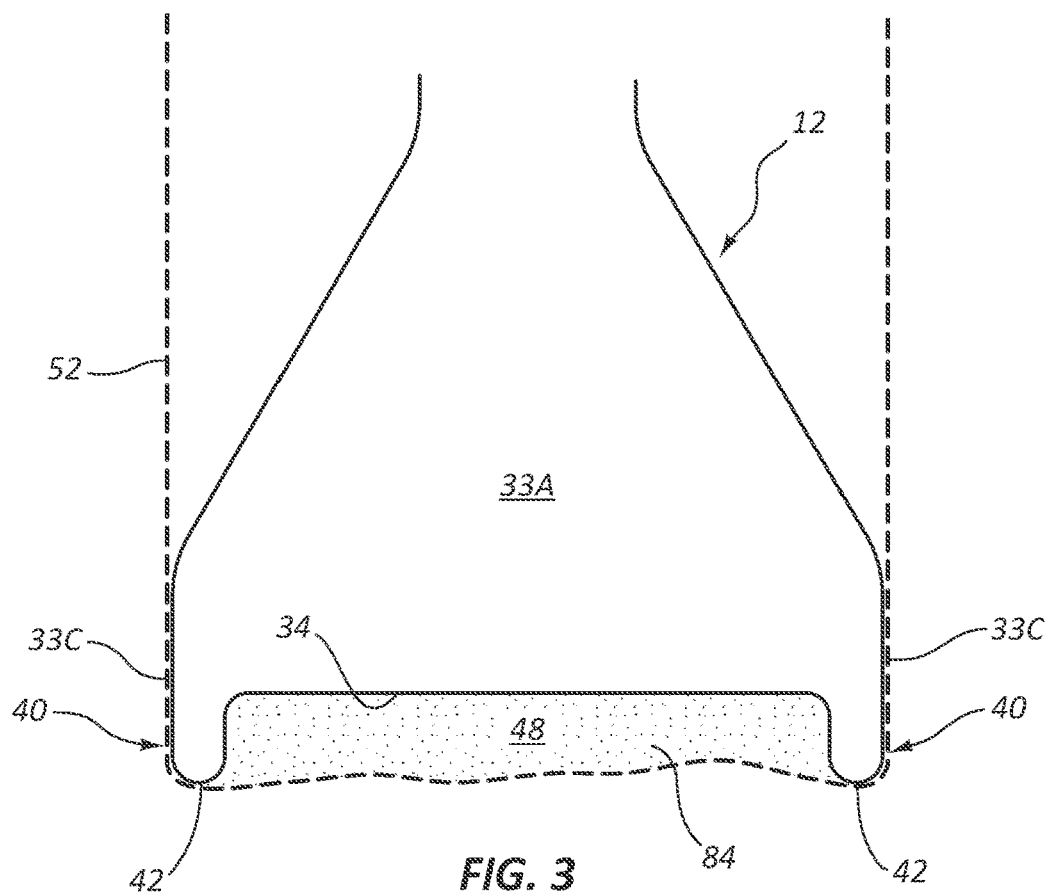
FIG. 3 is a side view of the ultrasound probe of FIGS. 1A and 1B enclosed within a sheath in accordance with one embodiment.

Reference is now made to FIG. 3 in describing one embodiment, wherein a sheath 52 is placed over the probe 12 to provide a sterile field about the probe. The sheath 52 can be disposed about the probe 12 such that a relatively close fit is defined between the sheath and the side faces 33C and front/rear faces 33A, 33B of the probe so that the ultrasound gel 84 can be included in and confined within the gap 48 by the sheath and the spacer elements 40. Note that sheaths or barriers of many different styles or configurations may be used.

Figure 4A:
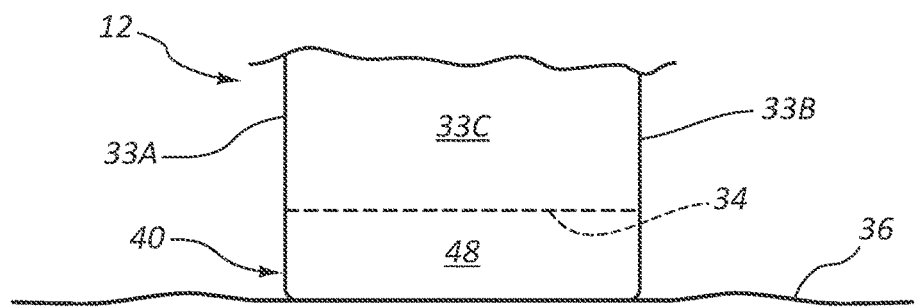
FIGS. 4A and 4B are side views of a portion of an ultrasound probe including spacer elements and further showing examples of possible acoustic surface configurations in accordance with one embodiment.
Figure 4B:
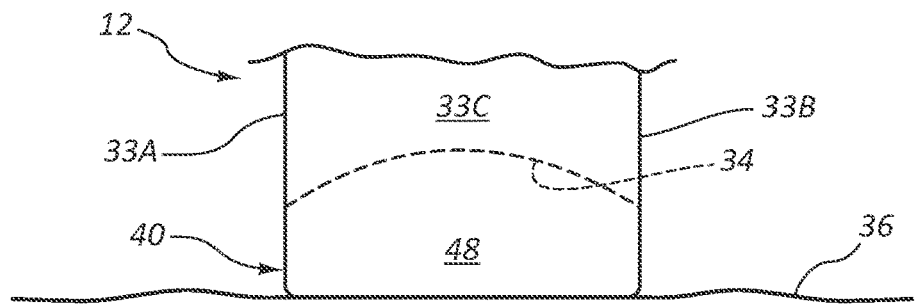

FIGS. 4A and 4B show example surface configurations for the acoustic surface 34. In FIG. 4A, the acoustic surface 34 is flat as to be substantially parallel with the patient's skin 36 during probe use. In FIG. 4B, the acoustic surface 34 defines a concave shape with respect to the skin 36. This configuration can assist in trapping a volume of ultrasound gel within the gap 48. Of course, other acoustic surface configurations can be employed.

Figure 5:
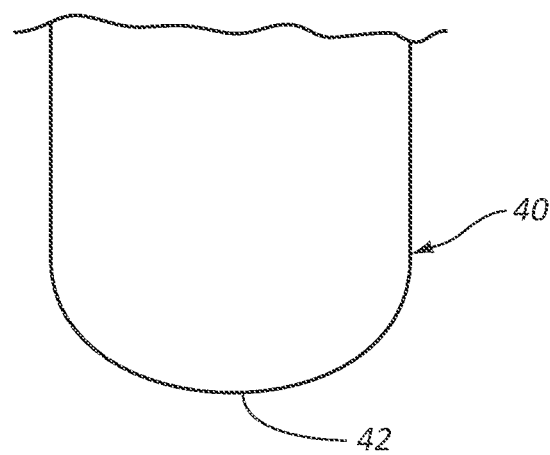
FIG. 5 is a side view of a portion of an ultrasound probe including a spacer element in accordance with one embodiment.

FIG. 5 gives one example of a possible configuration for the contact surface 42 of the spacer element 40, wherein the contact surface defines a convex shape for engagement with the patient's skin or other tissue surface. Note this is in contrast to the relatively flat contact surface 42 shown in FIGS. 4A and 4B, for instance. Other spacer contact surface shapes can be employed, including straight, rounded, angled, etc.

Figure 6:
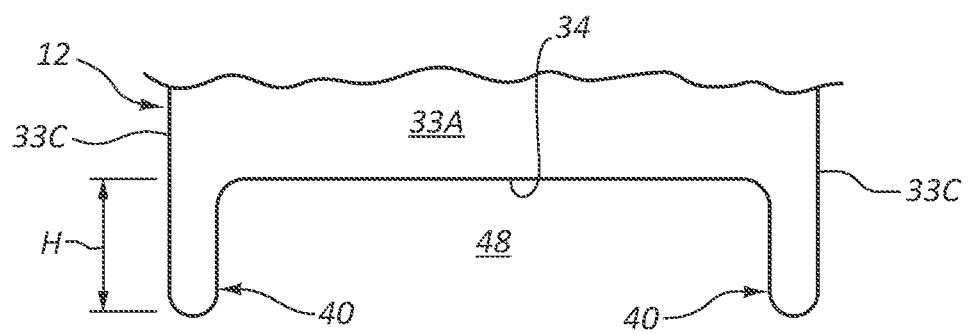
FIG. 6 shows ultrasound spacer elements configured in accordance with one embodiment.

FIG. 6 shows that a height "H" of each spacer element 40 can be defined according to a particular need or application in order to define a particular separation between the acoustic surface 34 and the patient's skin 36 during use of the probe 12. Note that in one embodiment, the spacer elements are integrally formed with the probe housing. In another embodiment, the spacer elements are removably attached to the probe. The spacer elements can include materials similar to or different from those materials included in the probe housing.

Figure 7:
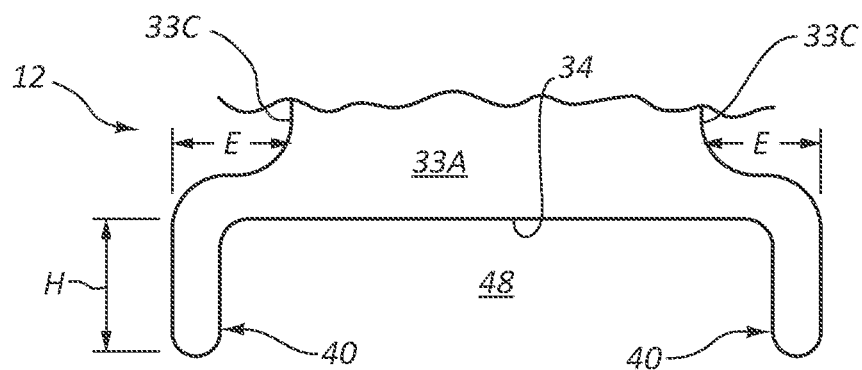
FIG. 7 shows ultrasound spacer elements configured in accordance with one embodiment.
Figure 8:
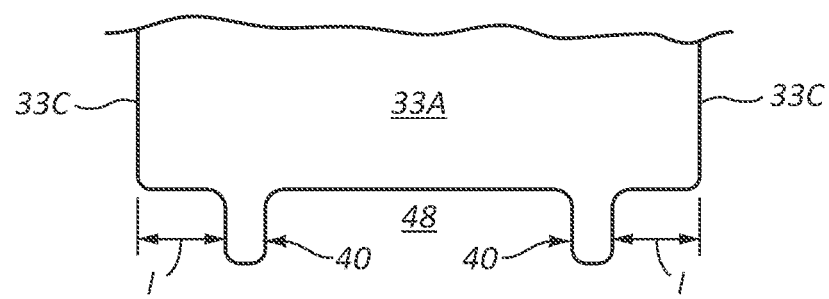
FIG. 8 shows ultrasound spacer elements configured in accordance with one embodiment.

Reference is now made to FIGS. 7 and 8, wherein FIG. 7 shows that in one embodiment the spacer elements 40 can be configured to extend longitudinally a distance "E" past the side surfaces 33C of the probe 12. In FIG. 8, each of the spacer elements 40 is inset a distance "I" from the probe side surfaces 33C.

Figures 9A, 9B:
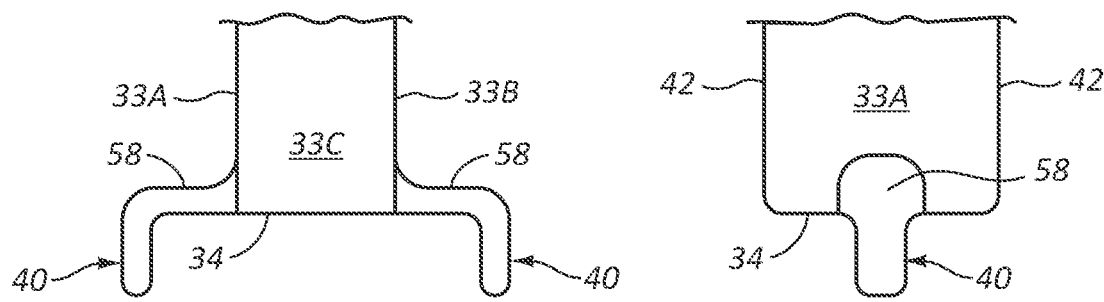
FIGS. 9A and 9B show spacer elements configured in accordance with one embodiment.

FIGS. 9A and 9B depict yet another possible spacer element configuration according to one embodiment, wherein each spacer element 40 is included at an end of an extension arm 48 that extends from a corresponding one of the front and rear faces 33A, 33B of the probe 12. Such a configuration may be useful, for instance, in advancing the probe 12 along the patient skin 36 in a direction parallel to the longitudinal length of the acoustic surface 34. These and other spacer configurations are therefore contemplated as residing with the spirit of the present disclosure.

Figure 10:
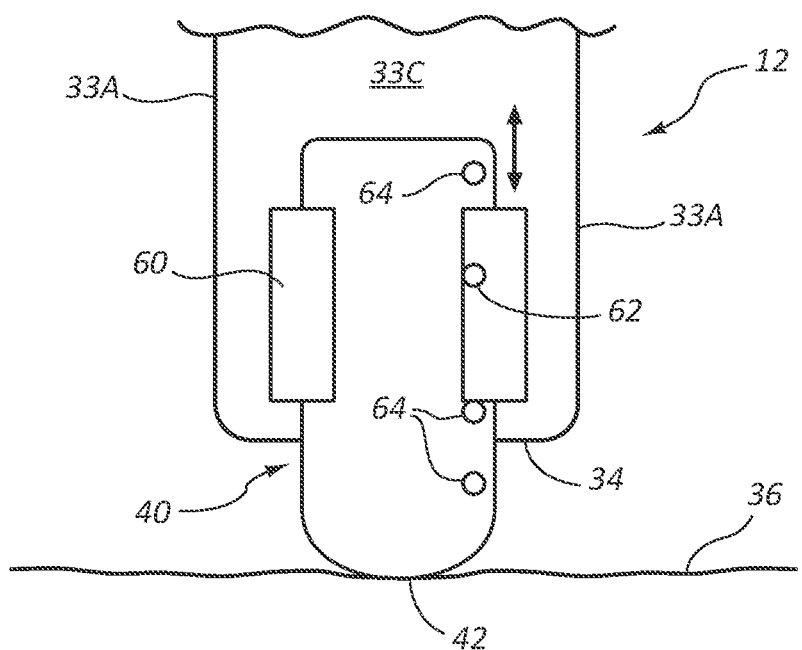
FIG. 10 is a side view of an ultrasound probe including spacer elements configured in accordance with one embodiment.

FIG. 10 shows a height-adjustable spacer element 40 so as to allow variation in the set-off distance of the acoustic surface 34 from the skin 36. In the illustrated embodiment, a bracket 60 that slidably receives the spacer element 40 is included on the side face 33C of the probe 12 and includes a depression or hole 62. Corresponding protuberances 64 are included on the spacer element 40 and are configured to be selectively received into the hole 62 so as to removably lock the spacer element in place at a specified height. The protuberances 64 are distributed along the length of the spacer element 40 such that one of multiple spacer heights may be selected. A similarly adjustable spacer element is included on the opposite side face of the probe 12. Of course, other adjustable spacer element configurations can be included on the probe in addition to that explicitly described here.

Figure 11:
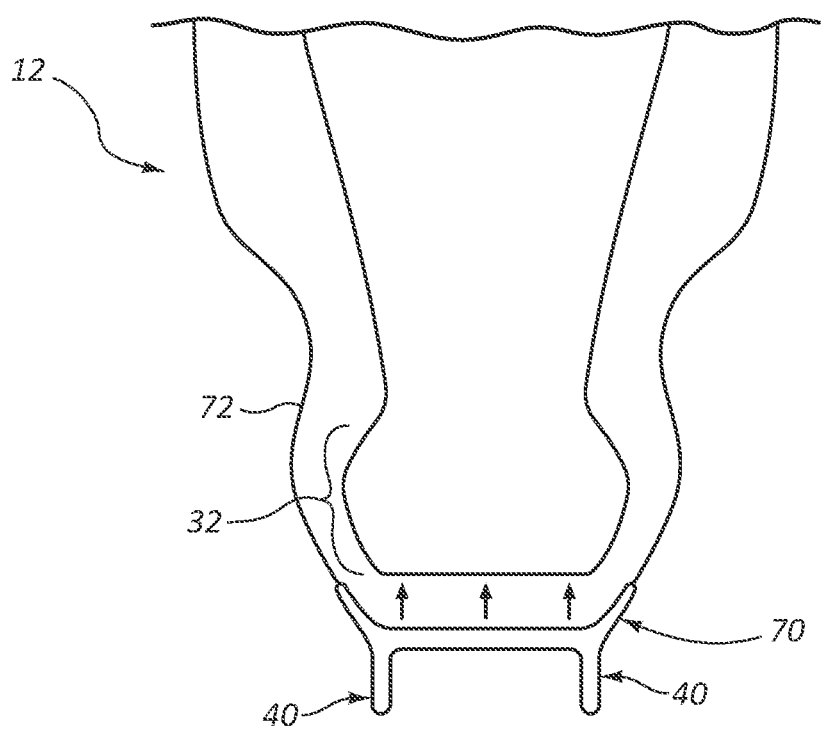
FIG. 11 is a side view of an ultrasound probe including a cap including spacer elements and a sheath in accordance with one embodiment.

FIG. 11 shows details of yet another embodiment, wherein the spacer elements 40 are included on a cap 70 that is removably attachable to the probe head 32. In the present embodiment, the cap is snapped on to the probe head 32 via an interference fit, but in other embodiments other attachment schemes can be employed, including inter-engaging surfaces on the probe and cap, for example. A sheath 72 is attached to the cap 70 so as to provide a sterile barrier for the ultrasound probe 10. In one embodiment the cap 70 and sheath 72 are disposable.

It should be appreciated that the number, size, height, shape, etc., of the spacer elements can vary from what is explicitly described herein. For instance, one, three, or more spacers can be included. Or the relative heights of the spacers can differ one from another so as to produce an angled probe-to-skin configuration. The probe can include one of many different shapes, designs, etc. These and other modifications are thus considered part of the present disclosure.

Figure 12:
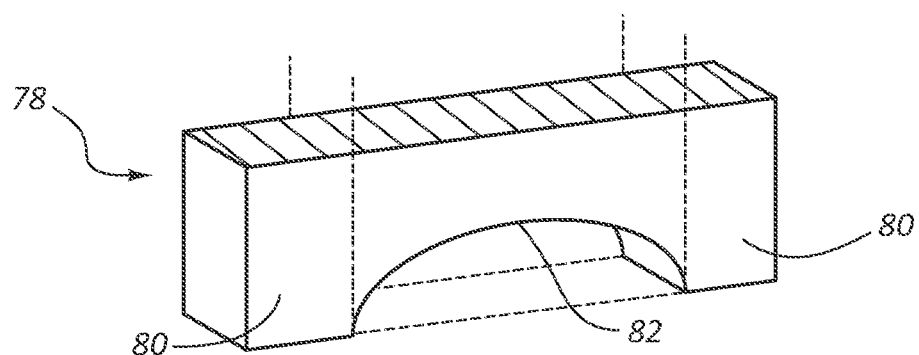
FIG. 12 is a perspective view of a spacer component in accordance with one embodiment.
Figure 13A:
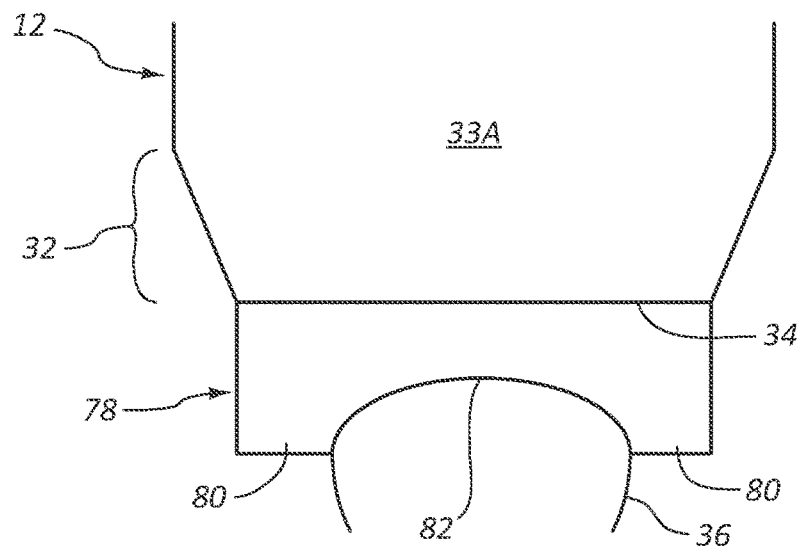
FIGS. 13A-13C show use of the spacer component of FIG. 12 in accordance with one embodiment.

FIG. 12 depicts details of a spacer component 78 configured for attachment to the probe head 32, as shown in FIG. 13A, according to one embodiment. The spacer component 78 includes a body of compliant material, such as a hydrogel, in one embodiment, which generally maintains its intended shape when deforming forces are absent. The compliant material in one embodiment can include AQUA-FLEX® ultrasound gel from Parker Laboratories, Inc., Fairfield, New Jersey. The spacer component 78 further defines spacer elements 80 on each longitudinal end thereof, with a concavity 82 defined between the spacer elements. It is appreciated that other suitable materials can be employed for the compliant material of the spacer component, including acoustically transparent, sufficiently solid materials such as soft silicone, rubber, etc. In one embodiment, the compliant material is thermoformable, sterilizable, and shelf stable for at least one year.

Figure 13B:
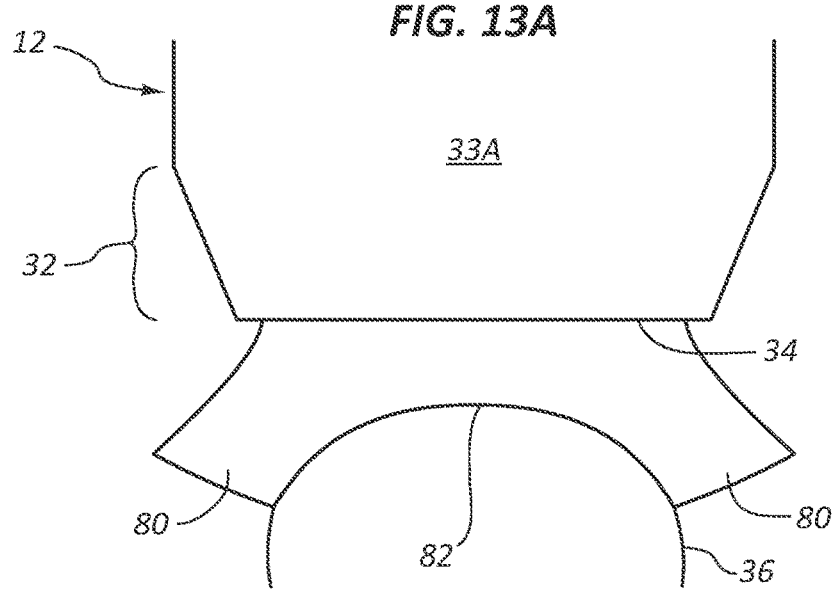
Figure 13C:
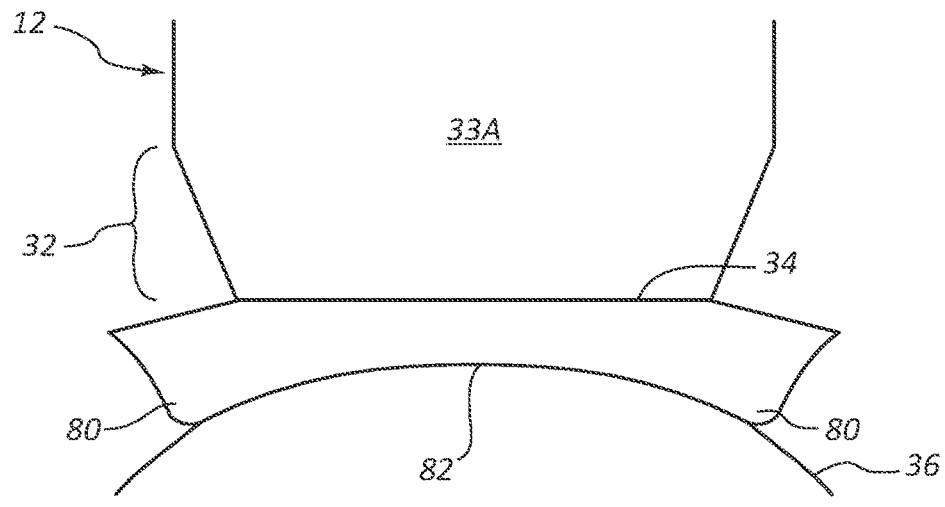

As shown in FIGS. 13A-13C, the spacer component 78 due to its compliant nature can deform so as to conform to the shape of the surface of the patient's skin 36 during use of the probe 12. For example, the probe 12 including the spacer component 78 can be placed on a patient's arm. So positioned, the spacers 80 of the spacer component 78 can deform as needed as to match the cross-sectional curvature of the arm surface and maintain contact with the skin 36 thereof. FIGS. 13B and 13C show such deformation of the spacer component 78 for relatively larger arms. Thus, the spacer component 78 provides an acoustic path between the acoustic surface and the skin surface without need of a flowable ultrasound gel. It is appreciated that the spacer component can be used in connection with imaging other portions of the patient's body and that the spacer component can define other shapes for contacting differently shaped body portions. Further, in one embodiment, an ultrasound gel can be included between the spacer component and the skin, such as in the concavity thereof.

Figure 14:
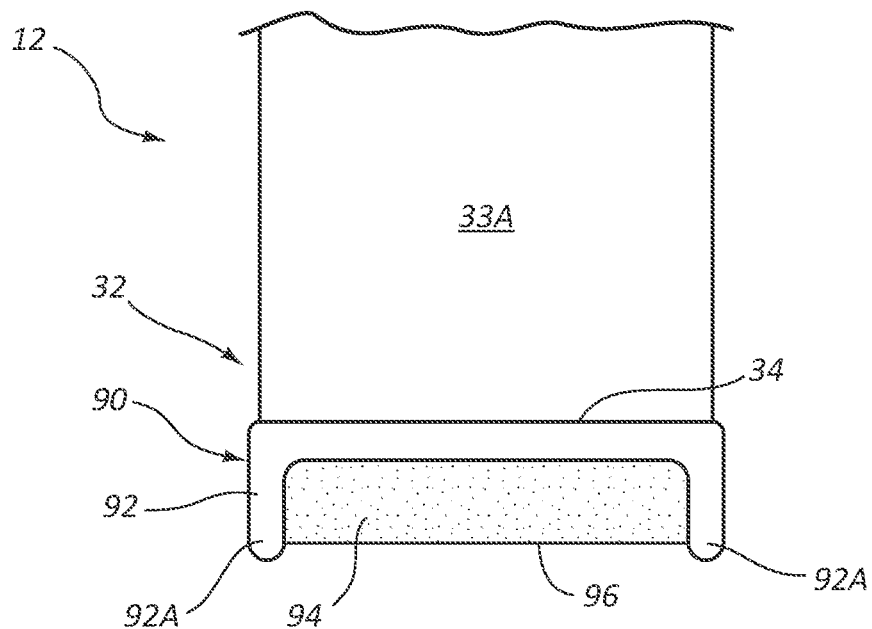
FIG. 14 is a side view of a spacer component in accordance with one embodiment.
Figures 15A, 15B:
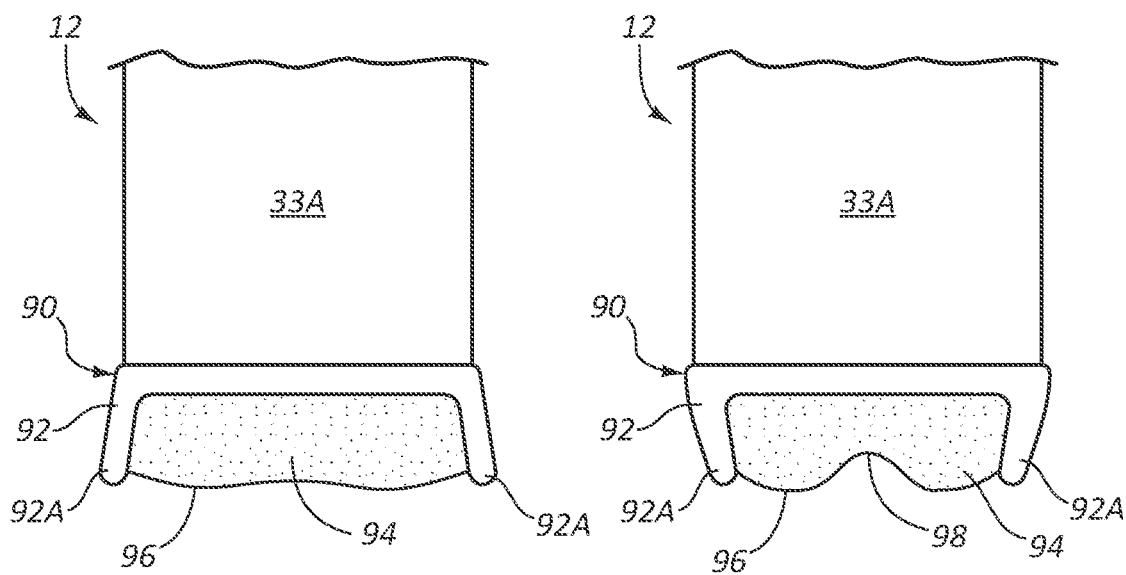
FIGS. 15A and 15B show use of the spacer component of FIG. 14 in accordance with one embodiment.

FIG. 14 depicts a spacer component 90 according to another embodiment, including a flexible casing 92 that can operably attach to the probe head 32, as shown. The casing 92 includes arms 92A that contain a compliant insert 94, such as hydrogel in one embodiment. As shown in FIGS. 15A and 15B, the spacer component 90 is positioned on the probe head 32 so as to provide both spacing and an acoustic path between the acoustic surface 34 and the surface of the skin 36 or other tissue surface such that flowable ultrasound gel is not needed. So configured, the insert 94 thereof defines a contact surface 96 for contacting the surface of the skin 36 during ultrasound probe use. In one embodiment, the arms 92A of the casing 92 can be pressed inward to modify the shape of the contact surface 96. For instance, FIG. 15A shows that the contact surface 96 of the insert 94 defines a relatively shallow concavity 98 when the arms 92A of the casing 92 are allowed to flex outward. When the arms 92A are pressed inward as in FIG. 15B, however, the insert 94 is compressed by the arms and the concavity 98 of the contact surface 96 becomes relatively more pronounced. Such a configuration of the contact surface 96 may be desirable to stabilize a position of the subcutaneous vessel while preventing its collapse. The arms 92A can be biased to restore themselves to a given position when not being pressed by a user.

Figure 16:
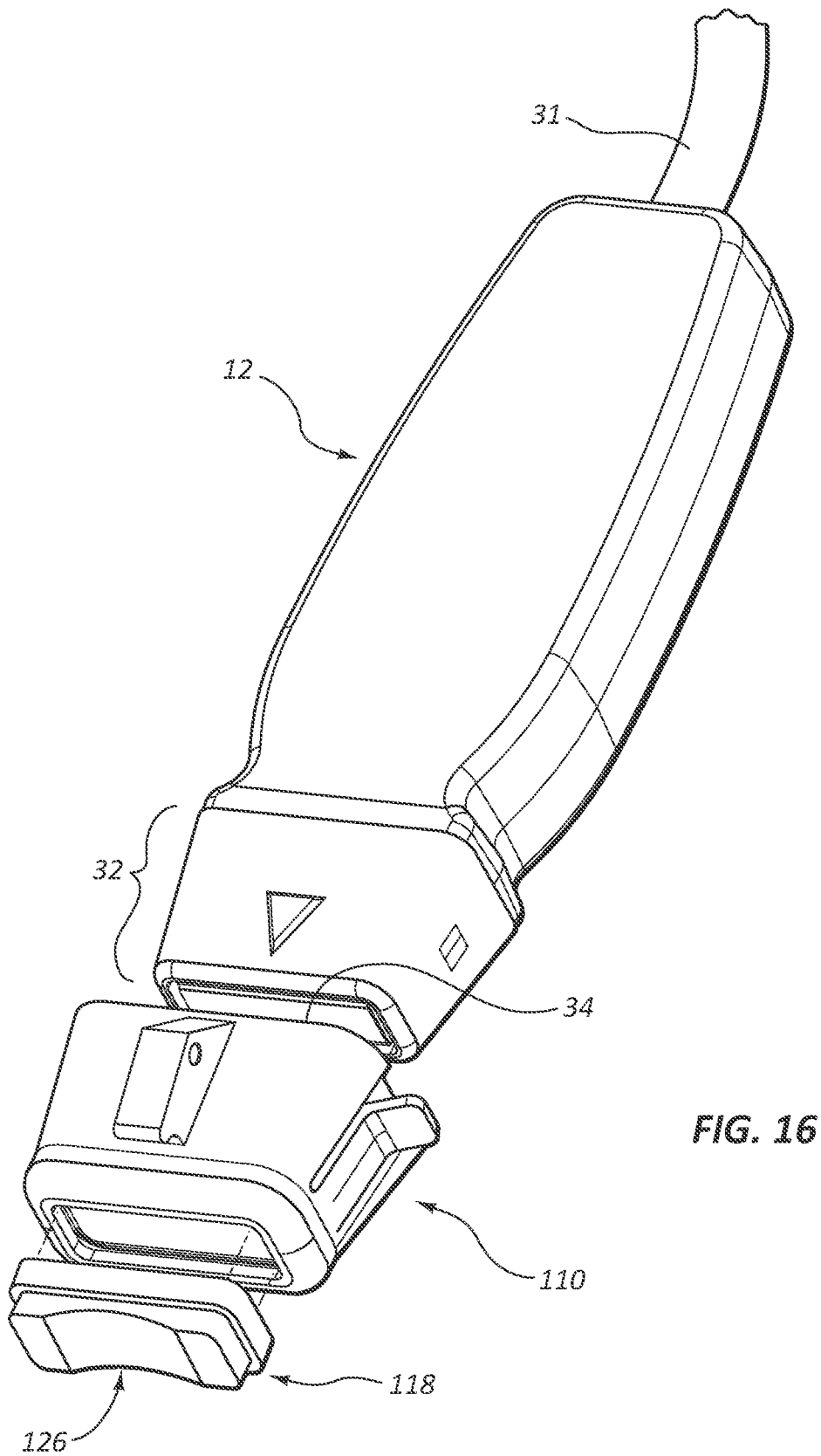
FIG. 16 is an exploded perspective view of an ultrasound probe and a probe cap in accordance with one embodiment.

FIG. 16 shows details of a probe cap 110 for use with the probe 12 according to one embodiment. The cap 110 is configured to receive therein the head 32 of the probe 12 and to provide a spacer component 118 for providing desired spacing between the acoustic surface 34 of the probe head 32 and the skin 36.

As shown in FIGS. 17A-17D, the cap 110 defines a cavity 112 that is sized to receive therein the head 32 of the probe 12. An engagement feature 114 is included with the cap 110 to releasably and mechanically attach the cap to the probe 12, though it is appreciated that various designs can be employed to accomplish the same functionality. The cap 110 further includes a needle guide base 116 on which a detachable needle guide can be placed so as to assist a clinician in placing a needle through the skin 36 after a vessel has been located through use of the ultrasound system 10 (FIG. 1A).

Figure 17A:
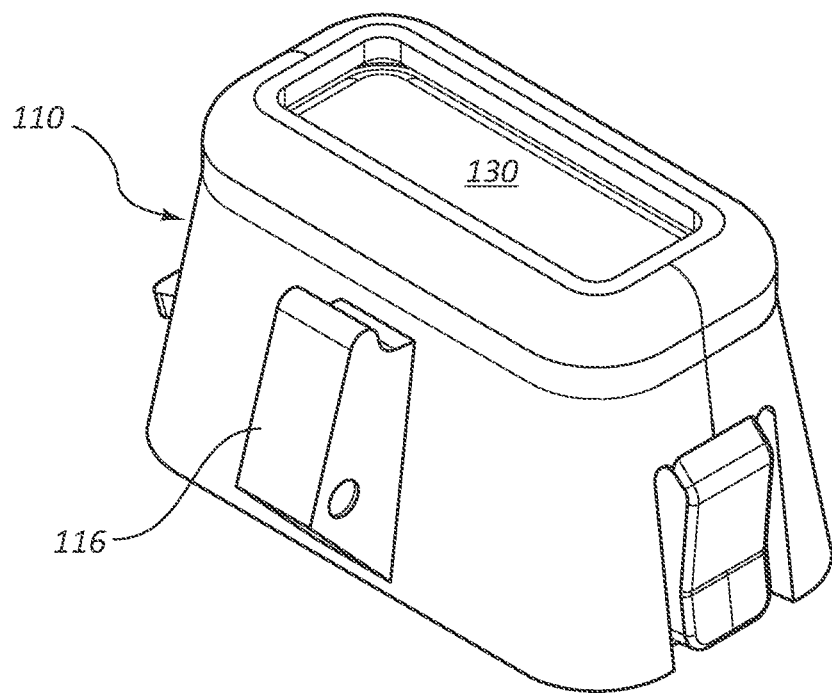
FIGS. 17A-17D are various views of the probe cap of FIG. 16.
Figure 17B:
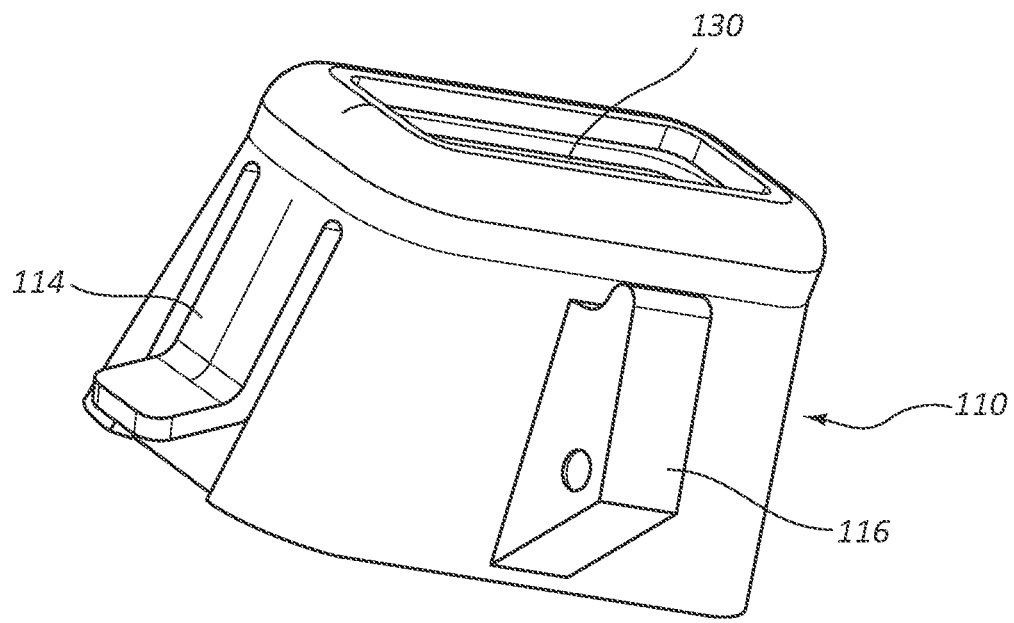
Figure 17C:
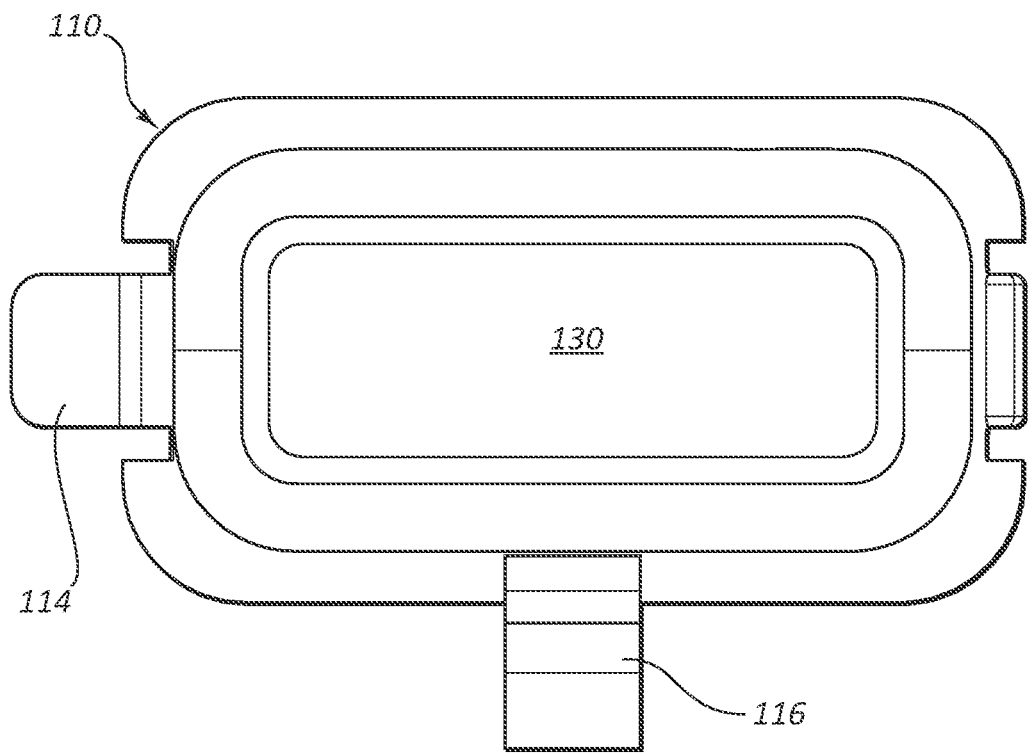
Figure 17D:
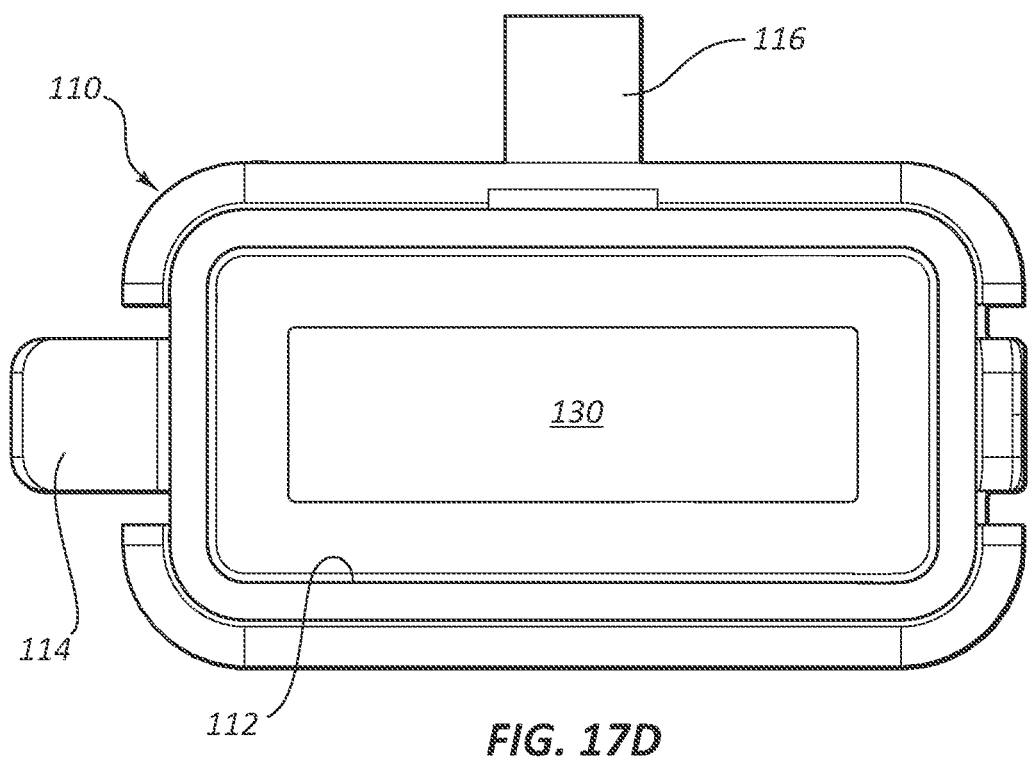
Figure 18A:
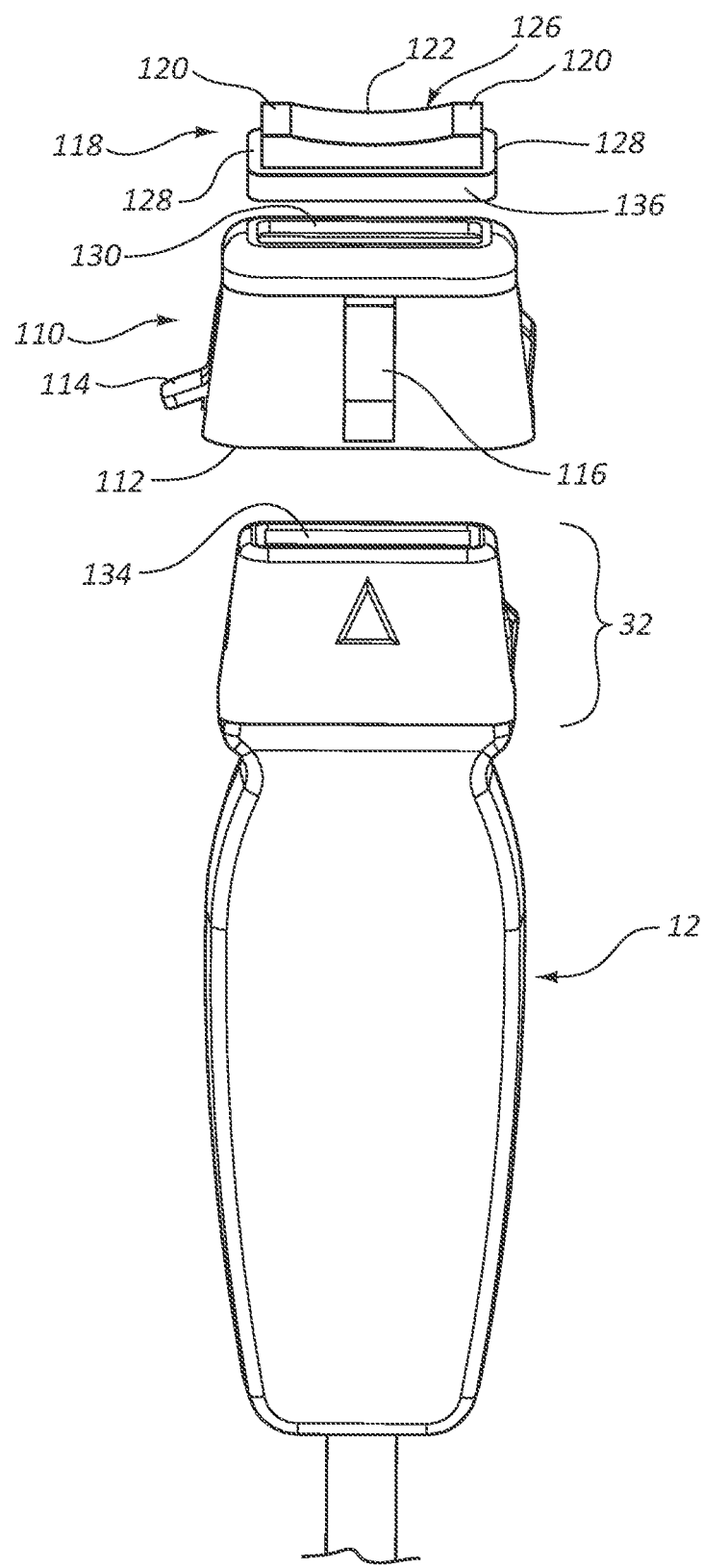
FIGS. 18A and 18B are an exploded perspective view and cross-sectional side view of an ultrasound probe/probe cap and a spacer component, respectively.
Figure 18B:
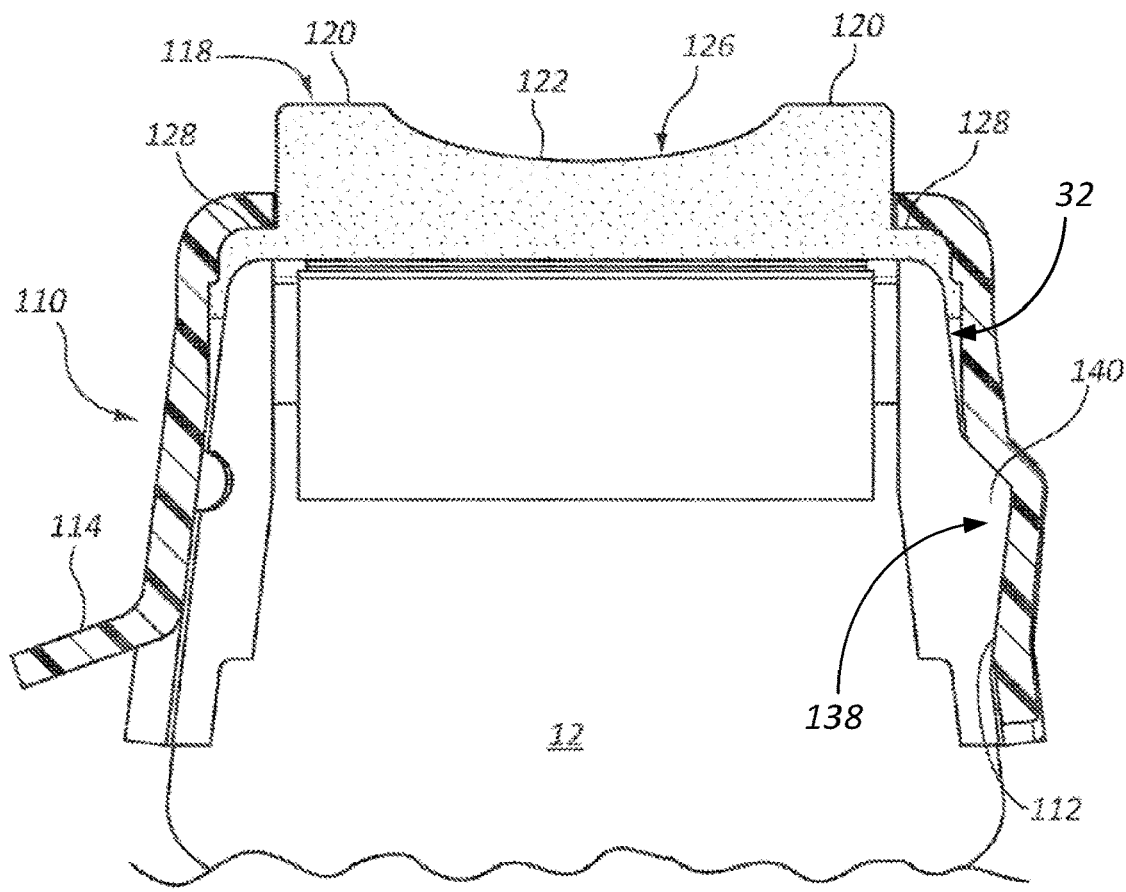

With continuing reference to FIGS. 17A-17D, reference is made to FIGS. 18A and 18B, which depict various details of the spacer component 118, which is disposed in a hole 130 defined in the cap 110, best seen in FIGS. 17A and 17C. As shown, the spacer component 118 includes a skin contact surface 126 that defines two spacer elements 120 and a concavity 122 disposed therebetween. The spacer component includes 118 a compliant material, such as hydrogel in one embodiment, though it is appreciated that other suitable materials can also be employed. The spacer component 118 thus requires no use of flowable ultrasound gel to be applied to the skin 36 in order to provide an acoustic path between the acoustic surface 134 and the patient's skin. The spacer component 118 further defines a lip 128 about a perimeter thereof to assist in its retention within the hole 130 of the cap 110, as seen in FIG. 18B. As shown, in the present embodiment the lip 128 is shaped so as to be sandwiched between the cap 110 and probe head 32, thus preventing its unintended removal from the cap. A recess 138 is also shown on the cap 110 to receive therein an orientation nub 140 on the probe head 32, which nub 140 provides a landmark for orienting an ultrasound image on the display 30 (FIG. 1A) with the orientation of the probe 12 as held by the clinician.

Figure 19:
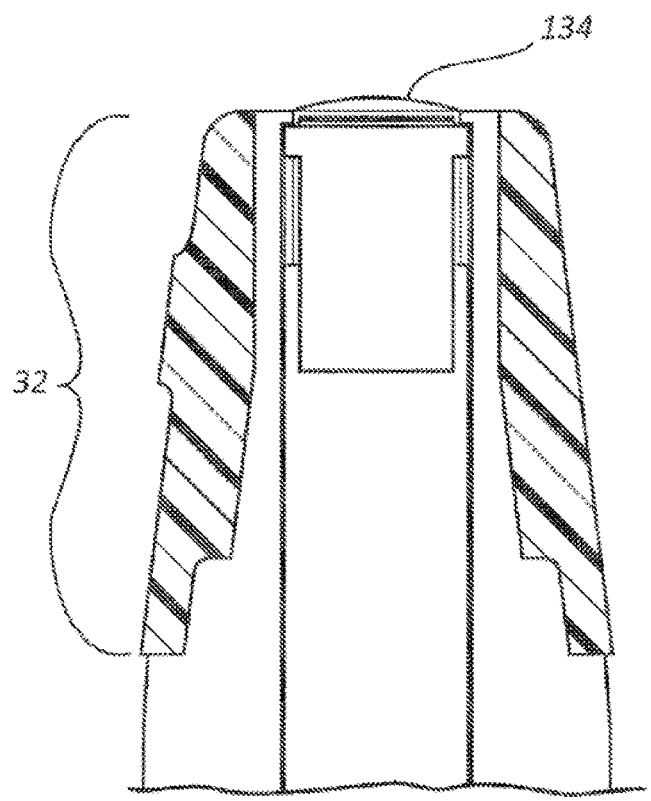
FIG. 19 is a cross-sectional view of a head portion of the ultrasound probe of FIG. 16.
Figure 20:
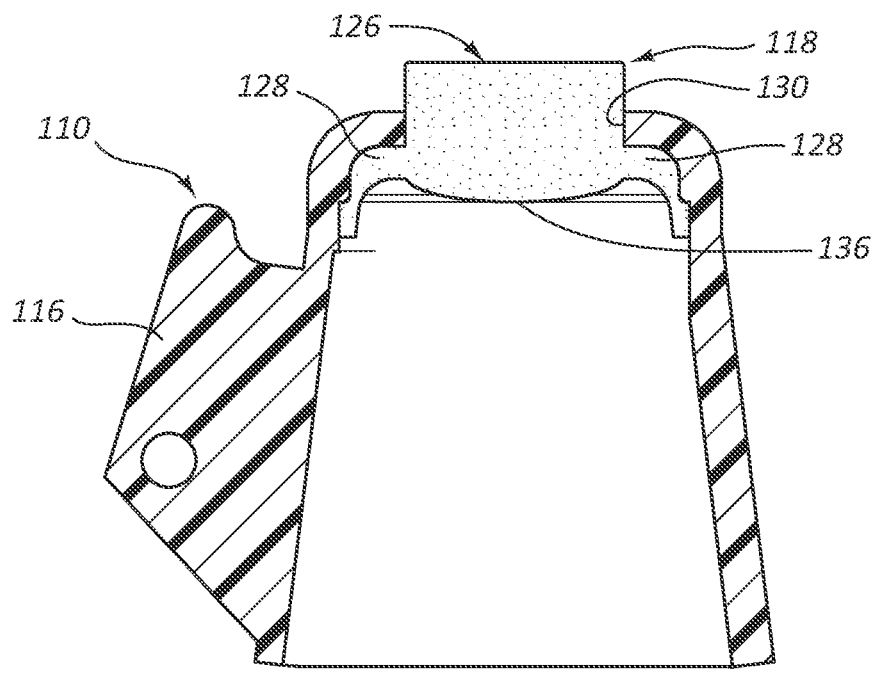
FIG. 20 is a cross-sectional view of the probe cap of FIG. 16.
Figure 21:
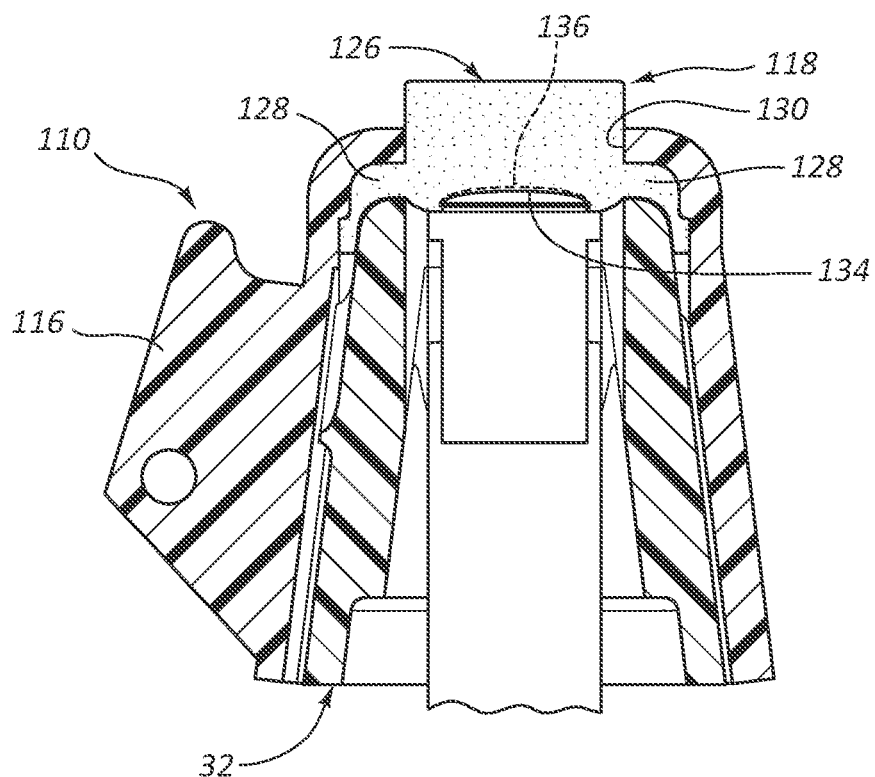
FIG. 21 is a cross-sectional view of a head portion of the ultrasound probe of FIG. 16 received within the probe cap of FIG. 16.

FIG. 19 shows that in the present embodiment the acoustic surface 134 of the probe head 32 defines a convex shape. Correspondingly, FIG. 20 shows that a probe contact surface 136 of the compliant spacer component 118 also defines a convex surface. FIG. 21 shows that when the probe head 32 is received into the cavity 112 of the cap 110, the convexly shaped probe contact surface 136 of the spacer component 118 deformably engages the convexly shaped acoustic surface 134 of the probe head 32 so as to ensure adequate contact therebetween and to provide a suitable acoustic path through the spacer component. Of course, other complementary shapes can be employed on the acoustic surface and probe contact surface of the spacer component.

Figure 22:
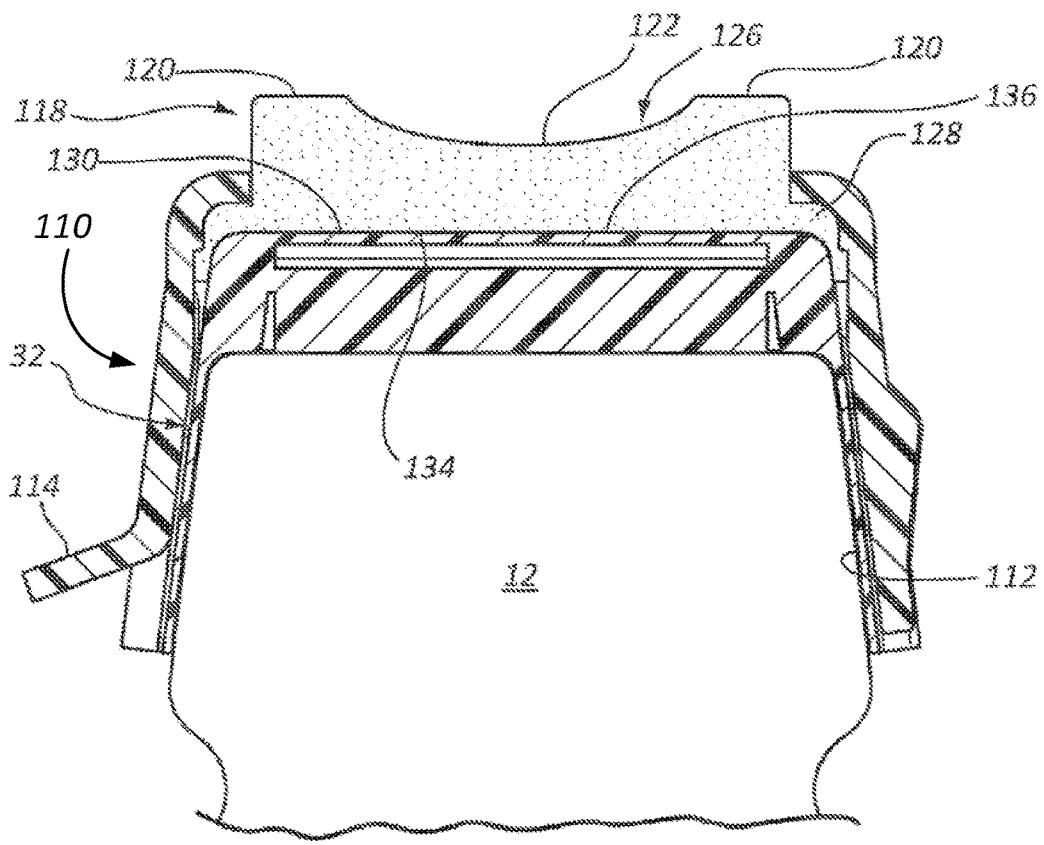
FIG. 22 is another cross-sectional view showing a head portion of the ultrasound probe of FIG. 16 received within the probe cap of FIG. 16.
Figure 23:
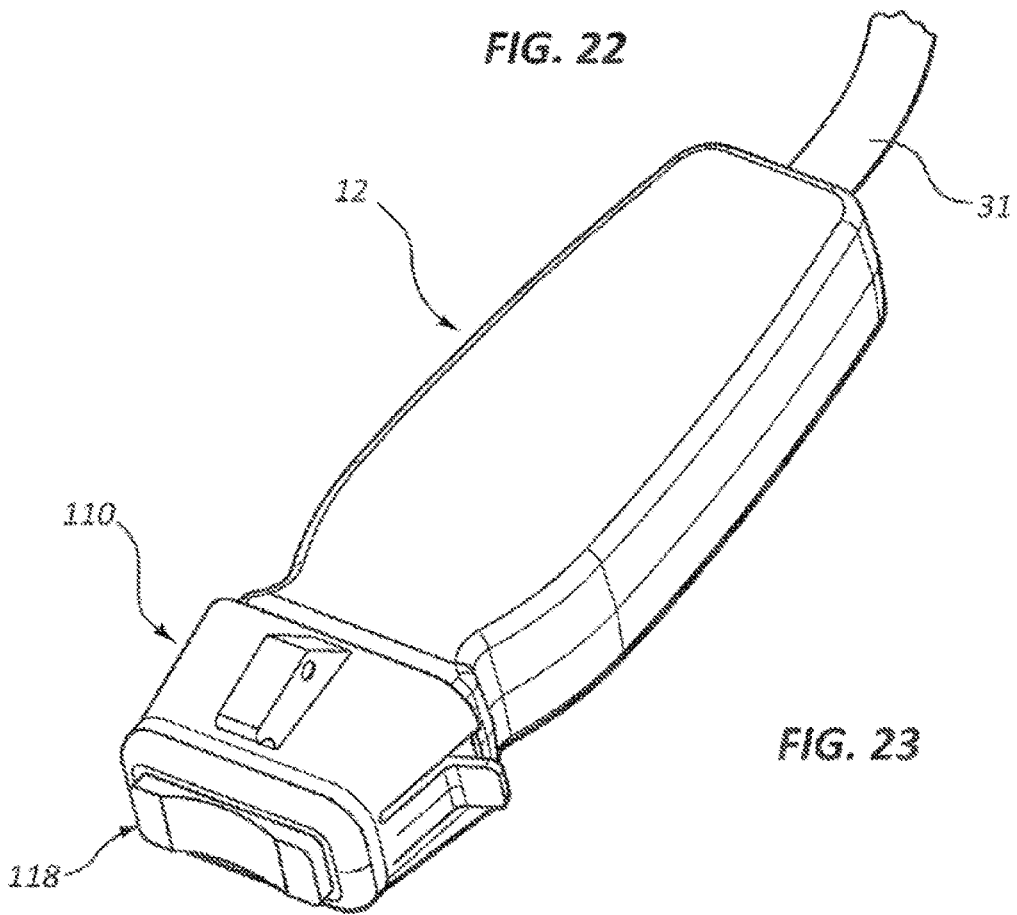
FIG. 23 is a perspective view of a mated configuration of the ultrasound probe and probe cap of FIG. 16.

FIG. 22 shows another view of the engagement between the probe head 32 and the cap 110, according to the present embodiment. FIG. 23 shows the cap 110, including the spacer component 118, removably attached to the probe 12. Note that in one embodiment the cap provides a sterile barrier for the probe head, and is disposable.

Figure 24A:
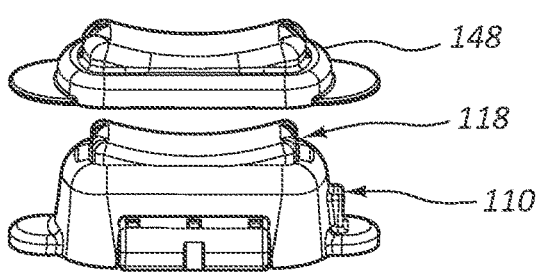
FIGS. 24A and 24B are front and side views, respectively, of an ultrasound probe and accompanying probe cap including a compliant spacer component according to one embodiment.
Figure 24A:
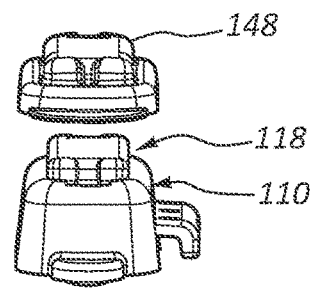
Figure 24A:
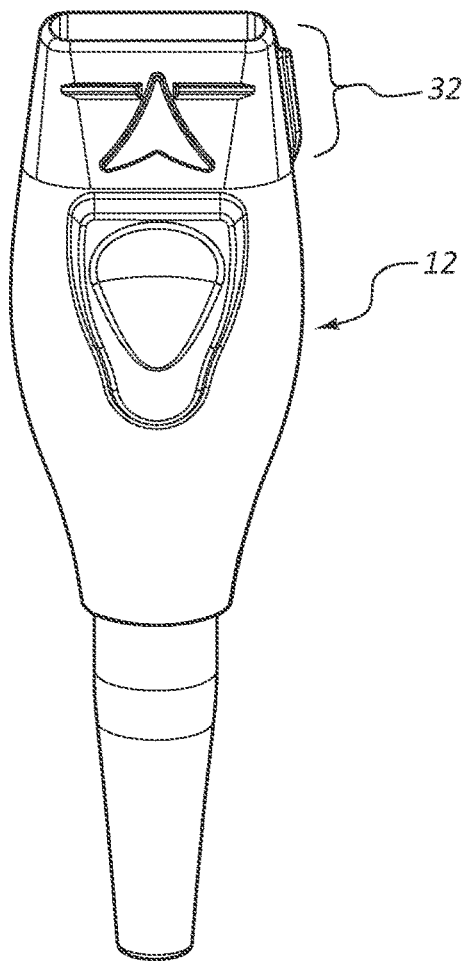
Figure 24B:
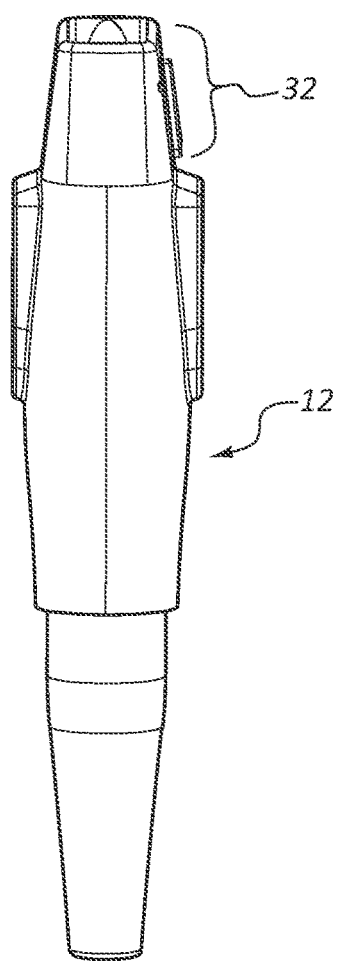
Figure 24C:
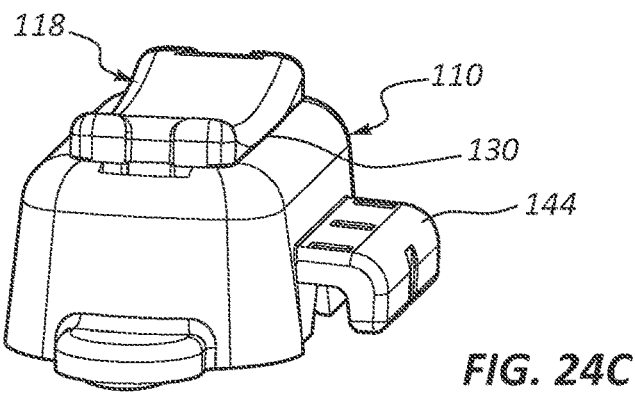
FIG. 24C is a perspective view of the probe cap of FIGS. 24A and 24B.

FIGS. 24A-24C depict the probe cap 110 and the concavely-shaped, compliant spacer component 118 according to one embodiment, together with the ultrasound probe 12. As shown, a suitably shaped cover 148 is also included for covering the spacer component 118 to prevent contamination thereof and to prevent the spacer component from drying out before use. When use of the probe cap is desired the cover 148, which is fit to the probe cap 110 via a friction or other suitable fit, can be simply removed and discarded by the clinician.

As best seen in FIG. 24C, the cap 110 includes in the present embodiment a bracket 144 to which a needle guide can be removably attached so as to enable guidance of a needle toward a desired vessel imaged by the ultrasound probe 12. Further details regarding one non-limiting example of a needle guide that can be attached to the bracket 144 can be found, for instance, in U.S. Pat. No. 9,974,516, issued May 22, 2018, and titled "Selectable Angle Needle Guide," which is incorporated herein by reference in its entirety. Note that the needle guide and bracket can vary from what is shown and described herein.

The discussion below discusses yet other structures for enhancing use of an ultrasonic probe in connection with placement of catheters and other medical devices in the body of a patient. Indeed, the embodiments disclosed herein facilitate ease of use when ultrasonically imaging portions of the patient body in preparation for device placement therein. Examples of such placement scenarios include the insertion by a clinician of a needle, PICC catheter, PIV catheter, mid-line catheter, etc. into the patient body via a transcutaneous insertion site.

FIGS. 25A-25D show details of a probe cap 160 according to one embodiment, which defines a cavity 162 for receiving therein the head 32 of the probe 12 and an engagement feature 164 for enabling removable engagement of the cap to the probe head. A fixture 166 is included on the side of the cap 160 and is configured for removably receiving thereon a needle guide 192. In another embodiment, this and other needle guides disclosed herein can be permanently attached to the cap. Note that, though not shown here, a spacer component similar to those shown and described in connection with FIGS. 24A-24C is disposed in the aperture 130 of the cap 160 to provide an acoustic pathway from the probe head 32 to the patient's skin.

Figure 25A:
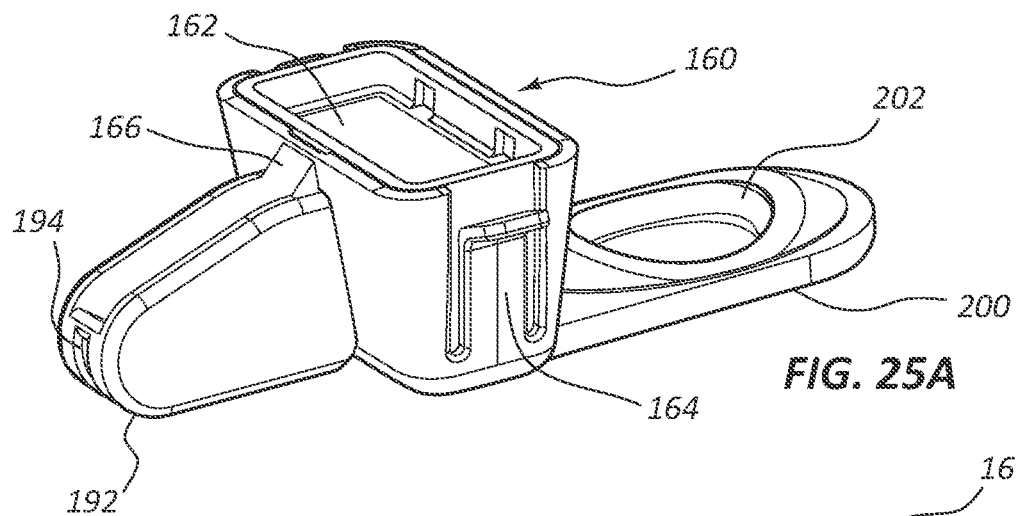
FIGS. 25A-25D are various views of a probe cap according to one embodiment.
Figure 25B:
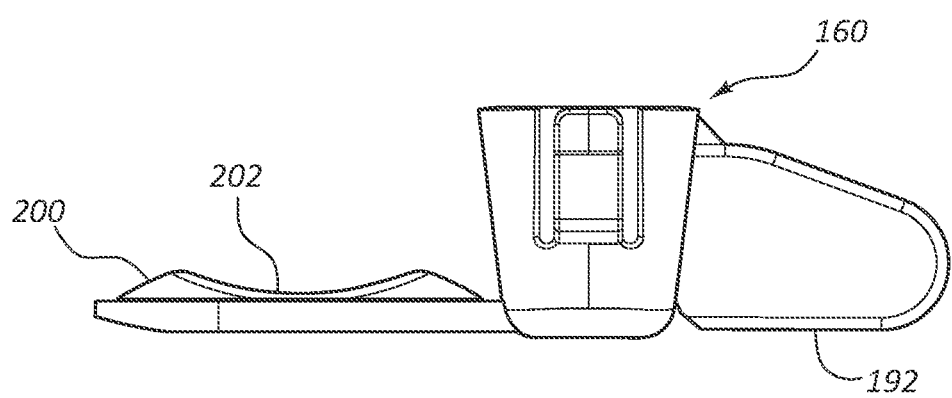
Figure 25C:
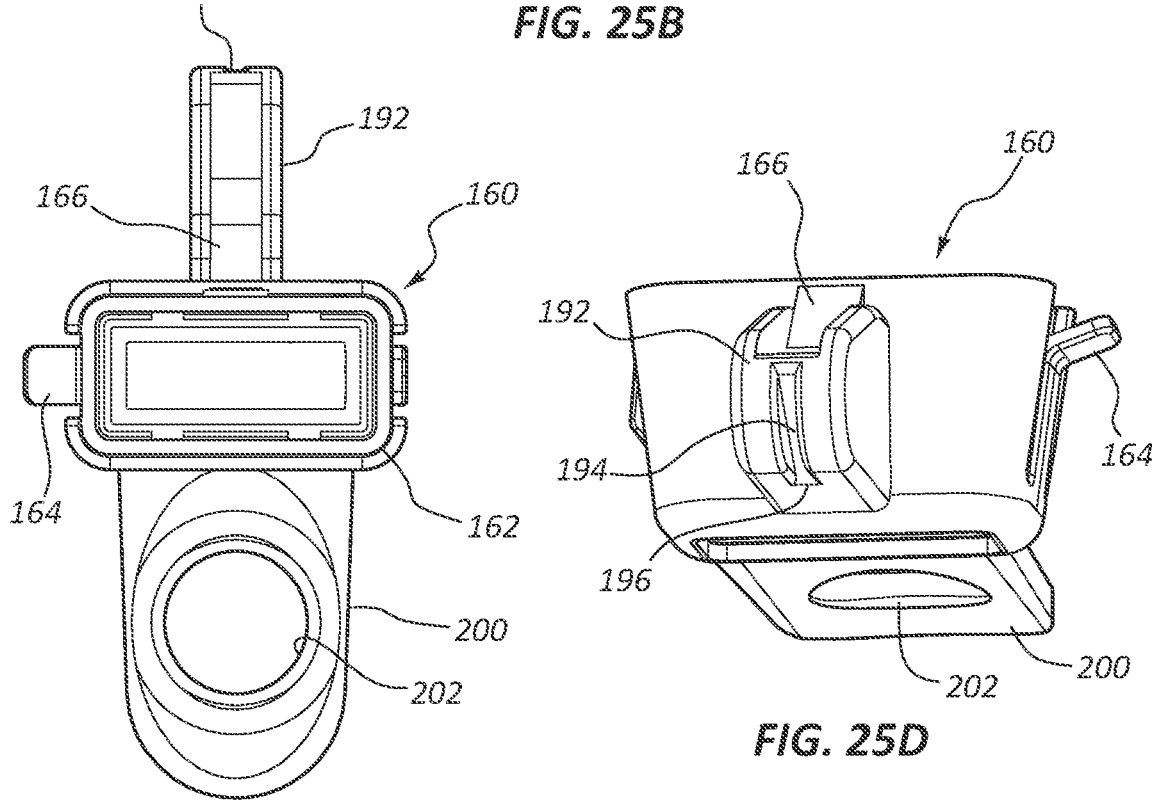
Figure 25D:
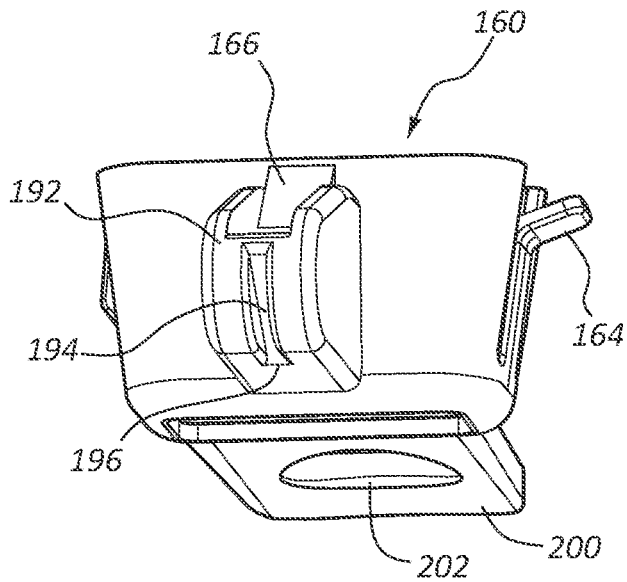

As best seen in FIG. 25D, the needle guide 192 defines a channel 194 into which a portion of a cannula of a needle to be inserted into the patient can be temporarily received. Note that the size of the channel can accommodate needle cannulas of various sizes/diameters, as here, or can be configured to accept needles of a predetermined size. An abutment surface 196 is included at a distal end of the channel 194 about which the needle can pivot so as to continuously define differing angles of attack with respect to the patient's skin during needle insertion procedures. As such, the needle guide 192 is capable of guiding the needle at any one of a variety of angles of attack toward the patient's skin while maintaining alignment of the needle with the subcutaneous vessel being imaged by the probe 12.

Note that the probe cap 160 and other caps discussed herein can be configured to mate with the head portion of the ultrasound probe in a variety of ways, including friction fit, clip-pocket engagement, adhesively, hook-and-loop, etc. The cap portion of the probe cap can also vary in design from what is shown and described herein.

Figure 26A:
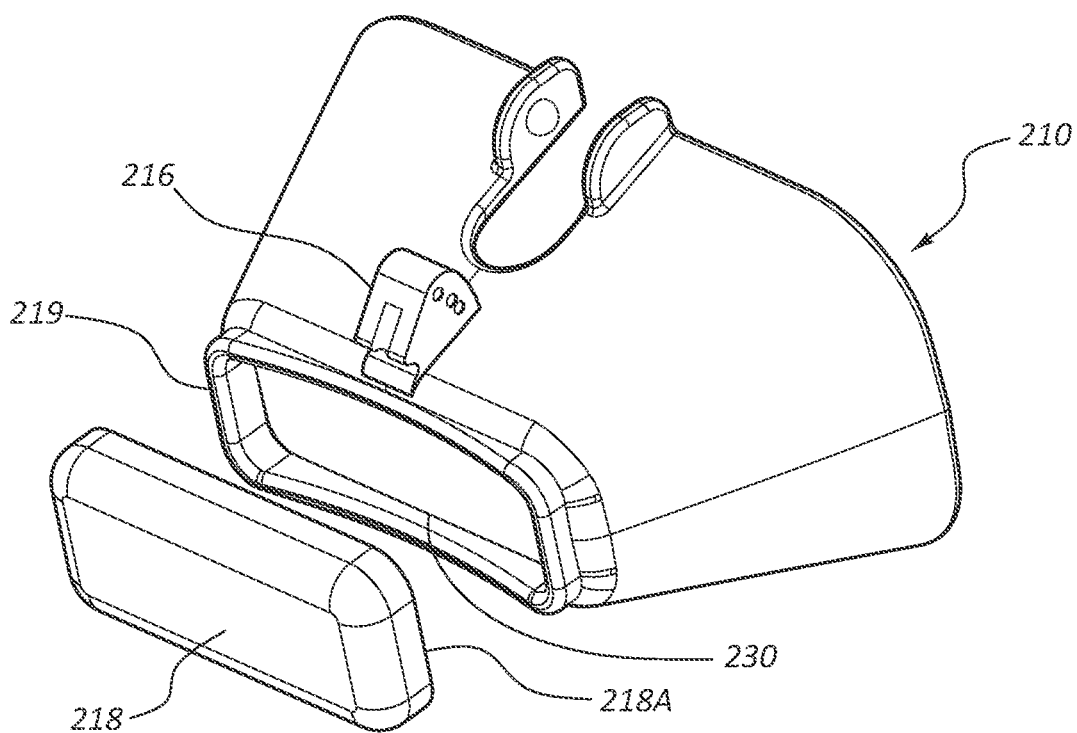
FIGS. 26A and 26B are various exploded views of a probe cap configured according to one embodiment.
Figure 26B:
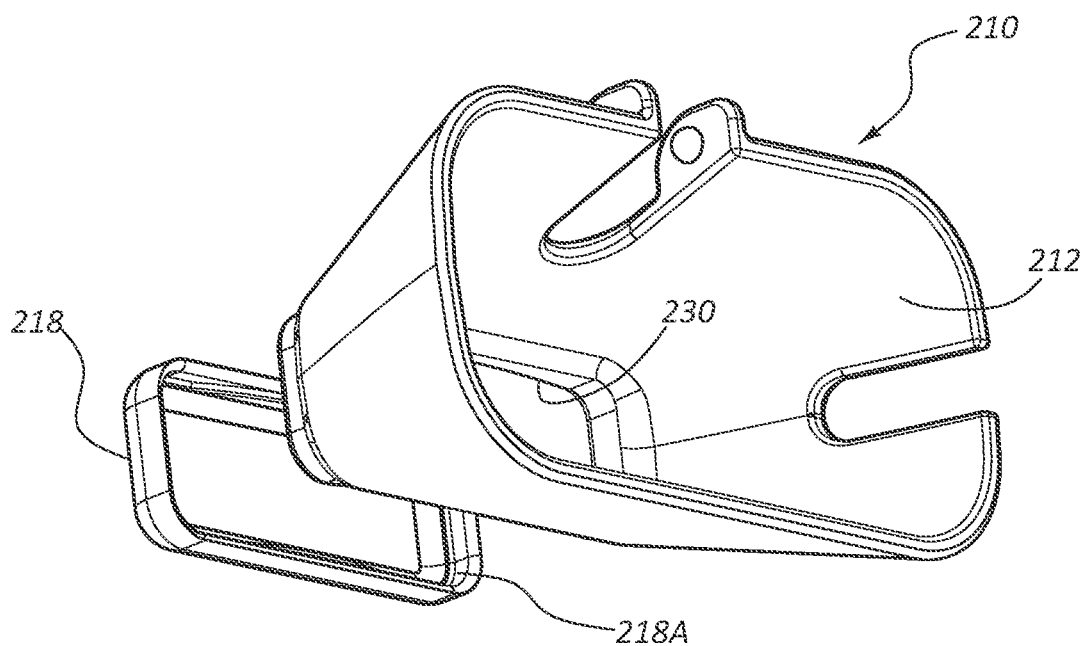

The cap 160 further includes a stabilization arm 200 extending from a distal portion of the cap body. The stabilization arm 200 is configured to rest against the skin of the patient when the cap-equipped probe is held vertically and placed against the patient's skin during ultrasound imaging procedures, thus stabilizing the probe in the vertical position. Moreover, the stabilization arm 200 can assist in securing the cap-equipped probe to the patient's skin via the use of a cord or elastic band, for instance, that is extended about the patient's arm and over the stabilization arm, thus maintaining the ultrasound probe in the upright position without manual contact by the clinician during use and providing more freedom to the clinician during the imaging procedure. A hole 202 is also defined in the stabilization arm 200 in one embodiment to enable the clinician to press the patient's skin therethrough in order to locate/occlude a subcutaneous vessel. The area proximate the perimeter of the hole 202 is contoured in the present embodiment to assist with finger placement by the clinician. FIGS. 26A and 26B show various details of a probe cap 210 according to another embodiment, including a cavity 212 defined by the cap body that is configured to supportably receive the head 32 of the ultrasound probe 12 therein via snap-fit or other suitable modality. A fixture 216 for receiving thereon a needle guide is also included on the cap body.

A compliant membrane 218 defining a lip 218A about its perimeter is included for attachment to the cap body. Specifically, the cap body defines a ridge 219 about an aperture 230 at the distal end of the body. The lip 218A of the membrane 218 is configured to resiliently attach to the ridge 219 so as to join the membrane to the cap body and cover the ultrasound transducer of the probe head 32 when the cap 210 is attached to the probe 12. The membrane 218 thus provides an acoustic pathway between the transducer and the patient's skin. Note that ultrasound gel on the patient's skin may, but need not, be used with the cap 210 during ultrasound imaging. Note also that the membrane 218 in one embodiment includes silicone, though other suitable, compliant materials can also be employed.

Figure 27:
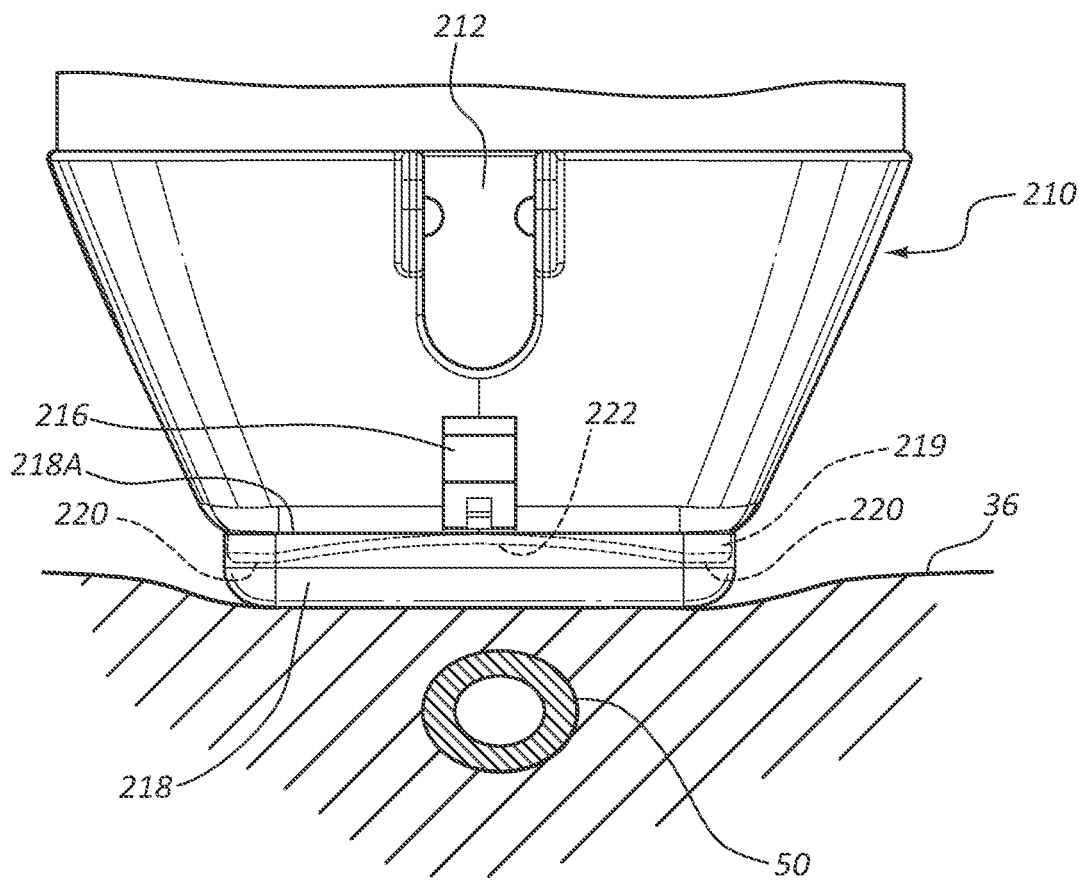
FIG. 27 is a side view of the probe cap of FIGS. 26A and 26B shown in contact with a patient's skin above a subcutaneous vessel.

In greater detail, the ridge 219 includes a concavely shaped concavity 222, as best seen in FIGS. 26A and 27, such that it defines two standoffs, or spacers 220, on either end. The compliant nature of the membrane 218 enables it to deform to the concavity 222 of the ridge 219 when the membrane is placed against the patient's skin during ultrasound procedures. Thus, the membrane 218 can conform to the skin 36 of the patient during ultrasound imaging so as to enable imaging of subcutaneous structures, such as a superficial vessel 50 seen in FIG. 27, without providing undesired compressive forces thereon.

Figure 28A:
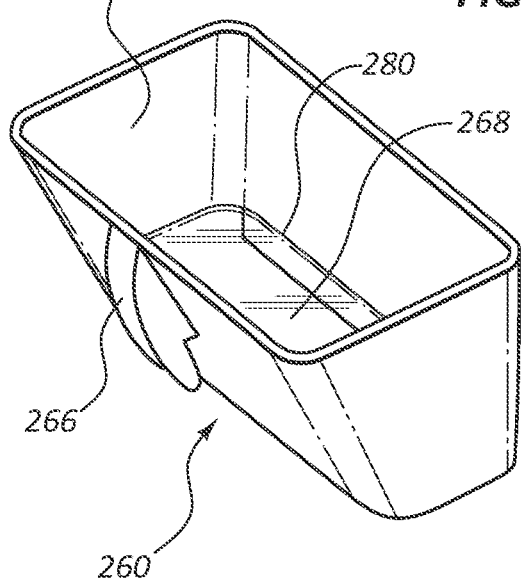
FIGS. 28A and 28B are perspective and cross-sectional views, respectively, of a probe cap according to one embodiment.
Figure 28B:
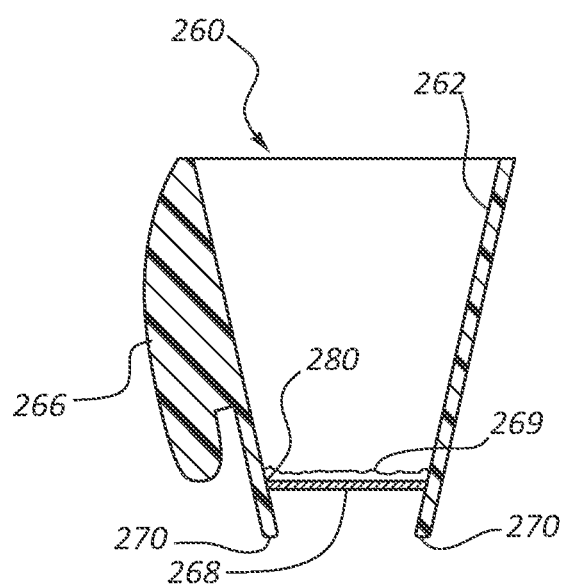

FIGS. 28A and 28B depict a probe cap 260 according to one embodiment, wherein the body of the cap defines a cavity 262 and a fixture 266 for receiving thereon a needle guide. An ultrasonically transparent membrane 268 is included proximate an aperture 280 at a distal end of the cap body to cover the transducer of the head of an ultrasound probe inserted therein. An ultrasonically transmissive medium, such as ultrasound gel 269, can be placed on an interior surface of the membrane 268 to ensure acoustic coupling between the transducer and the skin of the patient. As with other cap embodiments described herein the probe cap 260 can be configured as a sterile cap to provide sterility or isolation for the ultrasound probe. Spacers 270 can also be included on either side of the membrane 268 to prevent compression by the cap 260 of superficial vessels when the cap 260 is placed against the skin. Note that ultrasound gel can also be placed between the membrane 268 and the patient's skin to improve signal transfer, if desired.

FIGS. 29A-29D depict details of a probe cap assembly 310 according to another embodiment, wherein the assembly includes a cap body defining a cavity 312 for receiving therein the head 32 of the ultrasound probe 12, as before. Also as before, an engagement feature 314 is included to secure the cap body to the probe 12.

The cap body is movable between two parallel rails 350 of a bracket 340. Each rail 350 includes a plurality of slots 352 that align with corresponding slots on the opposing rail 350. Tabs 319 included on either longitudinal end of the cap body are configured to be selectively received into corresponding opposed slots 352 of the rails 350, as shown in FIGS. 29A-29D. In the illustrated embodiment, the cap body is selectively repositionable along the bracket rails 350 via manual movement by lifting the cap body so as to remove the tabs 319 from the corresponding slots 352, repositioning the cap body as desired with respect to the bracket rail slots, then inserting the tabs into the selected slots. In other embodiments, it is appreciated that other modalities for moving the cap body relative to the bracket are possible, including sliding movement, gear-driven movement, etc.

Figure 29A:
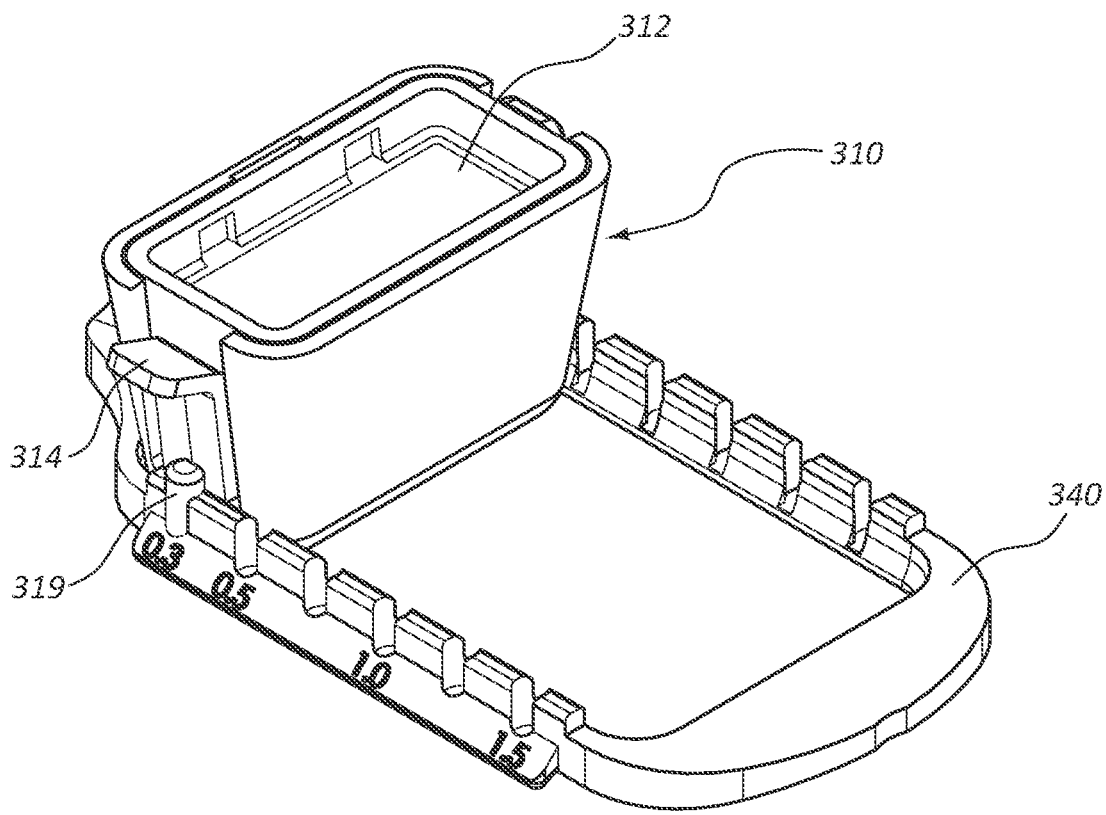
FIGS. 29A-29D are various views of a probe cap assembly according to one embodiment.
Figure 29B:
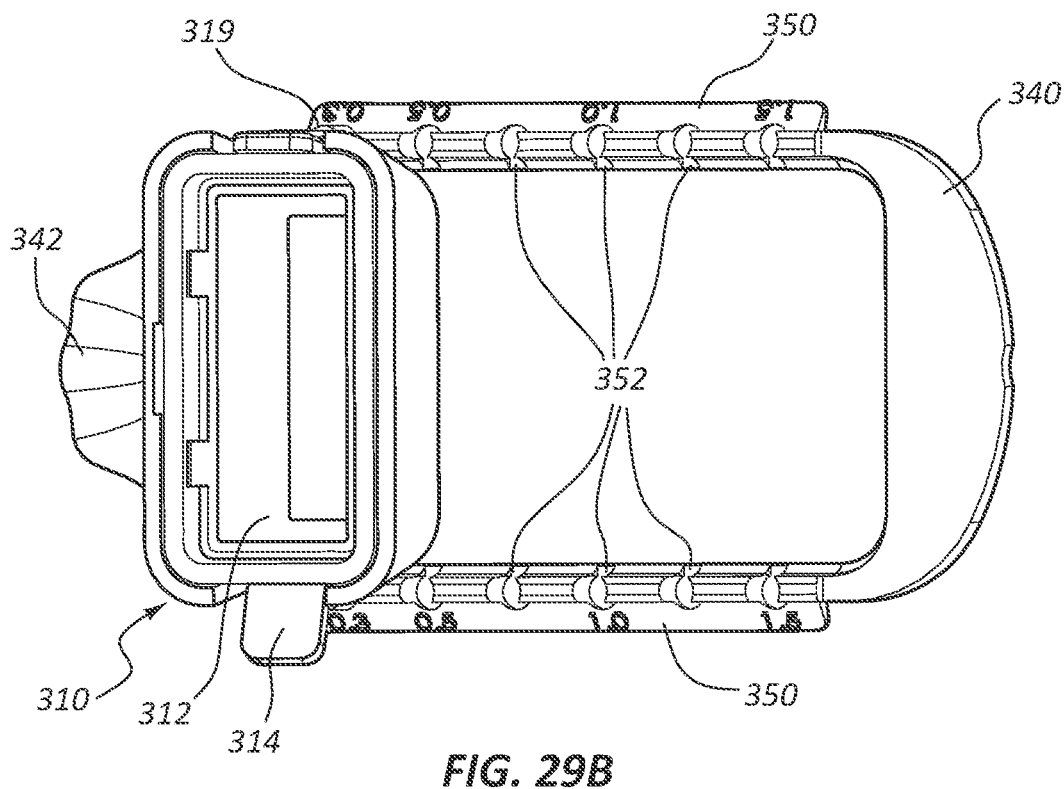
Figure 29C:
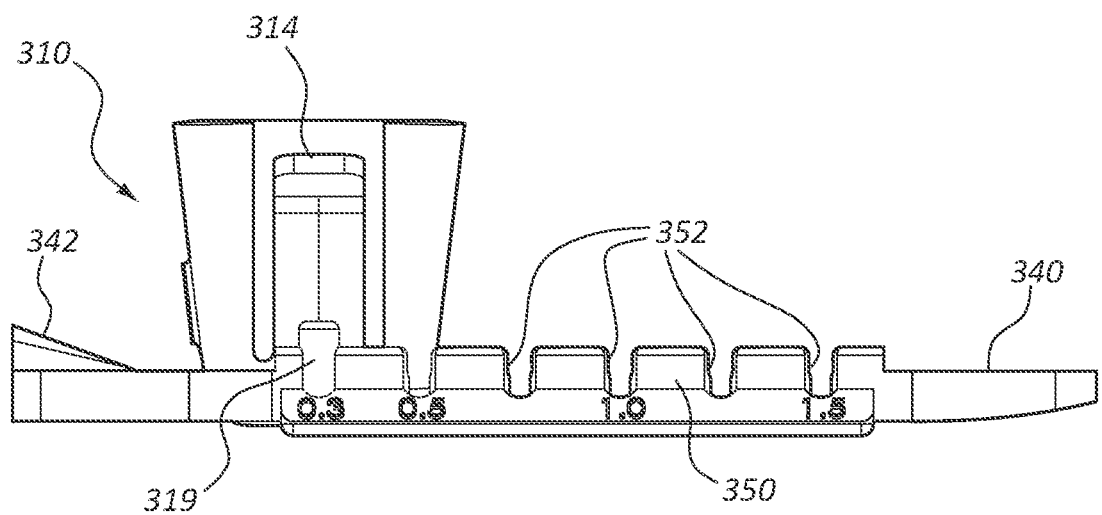
Figure 29D:
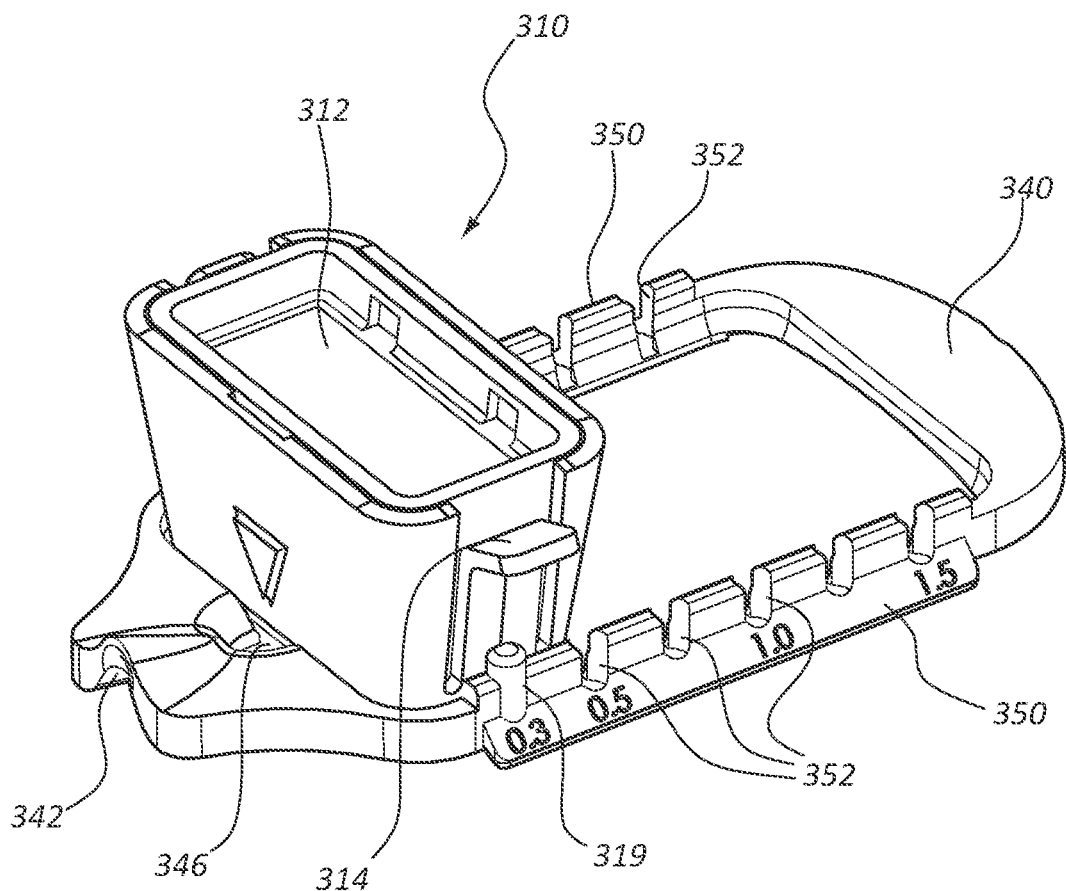

As best seen in FIGS. 29B-29D, a needle guide 342 is included in the bracket to guide a needle into the patient's body when the probe cap assembly 310 is placed on the patient's skin. An observation hole 346 is also included on the bracket 340 so as to enable a clinician inserting the needle to observe blood flashback upon the needle accessing the subcutaneous vessel.

Note that the needle guide 342 in the present embodiment is disposed at a fixed angle with respect to the bracket 340 and that the cap body is movable along the bracket with respect to the needle guide. This arrangement thus enables subcutaneous tissue to be imaged, by the ultrasound probe disposed in the cap body, at differing discrete distances from the needle guide 342. Further, this arrangement enables a needle inserted through the needle guide 342 to access an ultrasonically imaged vessel or other target at any one of a plurality of depths below the skin without the need for adjusting the angle of attack of the needle.

In greater detail, the probe 12 while disposed in the cap body of the probe cap assembly 310 can ultrasonically image a subcutaneous vessel within the patient and determine the depth below the skin surface at which the vessel resides. One or more of the slots 352 are marked with a number, indicating the depth below the skin at which a needle inserted into the patient through the needle guide 342 will intercept the subcutaneous vessel. Thus, the bracket 340 can be adjusted until the tabs 319 thereof are disposed in the slots 352 on either rail 350 corresponding to the depth of the imaged vessel. When the needle is inserted into the patient's skin through the needle guide 342, it can be advanced until it intercepts and accesses the imaged vessel at the determined depth, as desired. As such, it is appreciated that the probe cap assembly 310 can assist with needle access of an ultrasonically imaged vessel through a fixed-angle needle guide regardless of the depth of the vessel, thus obviating the need for an adjustable angle needle guide in the present embodiment. Note that the depth measurements of the bracket can vary from what is shown, but in one embodiment, the depths accessible via the probe cap assembly 310 vary from about 0.3 cm to about 1.5 cm.

Figure 30A:
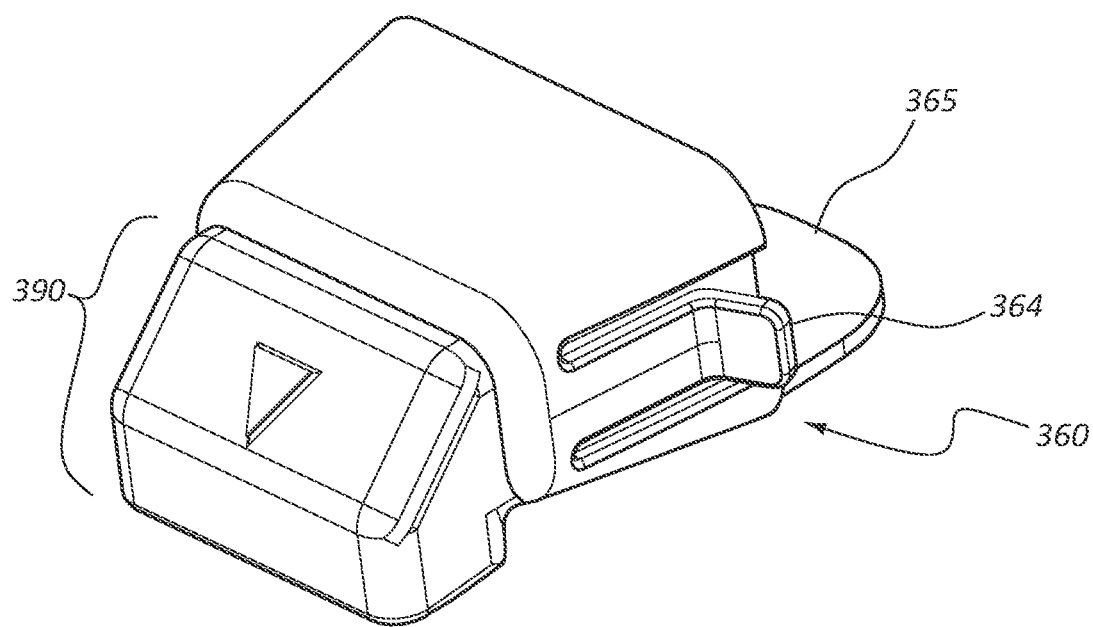
FIGS. 30A and 30B are various perspective views of a probe cap according to one embodiment.
Figure 30B:
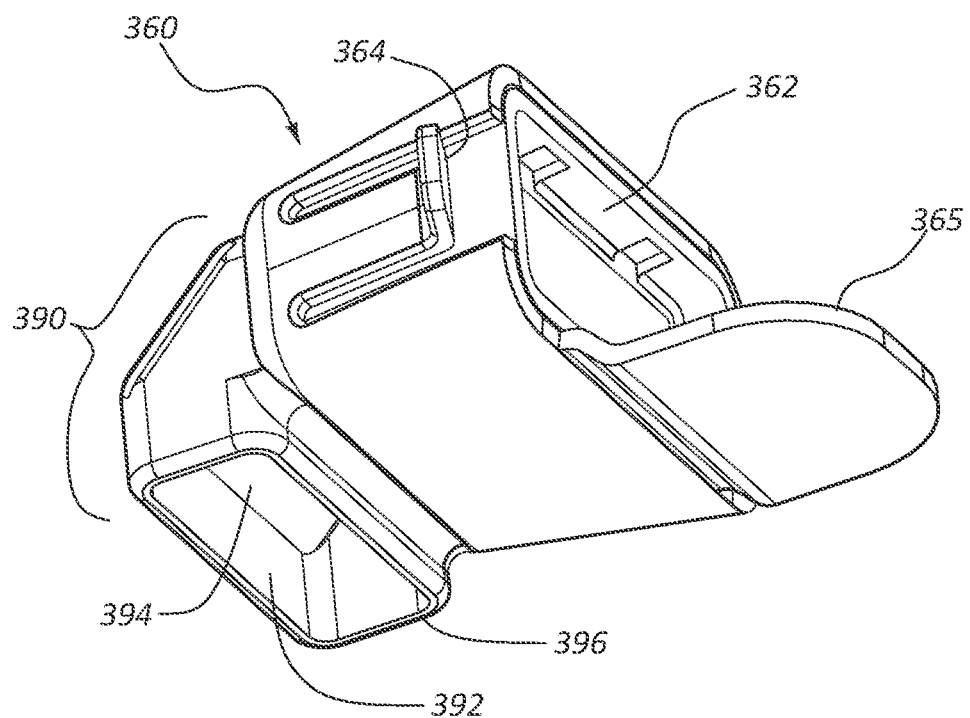

FIGS. 30A and 30B depict a probe cap 360 according to another embodiment, wherein the cap body defines a cavity 362 for receiving therein the head 32 of the ultrasound probe 12 and an engagement feature 364 to secure the cap body to the probe 12. A stabilization arm 365 extends from the cap body so as to enable the cap 360 (and the probe 12 received therein) to be secured to the patient via a band wrapped around the stabilization arm and the arm of the patient, for instance.

As shown, the probe cap 360 further includes a deflector portion 390 for deflecting an ultrasound signal both emanating from and travelling to the transducer of the ultrasound probe 12. The deflector portion 390 is formed as part of the probe cap 360 and defines a channel 392 and an aperture 396 through which ultrasound signals can pass. The deflector portion 390 further includes a deflecting surface 394 disposed in the channel 392. In the present embodiment the deflecting surface 394 is disposed at an angle of about 45 degrees with respect to the transducer surface of the probe head 32 so as to deflect ultrasound signals emanating therefrom through an angle of about 90 degrees, though the deflecting surface can be positioned in other embodiments at other angles so as to produce different resulting angles of signal deflection with respect to the probe transducer.

Figure 31:
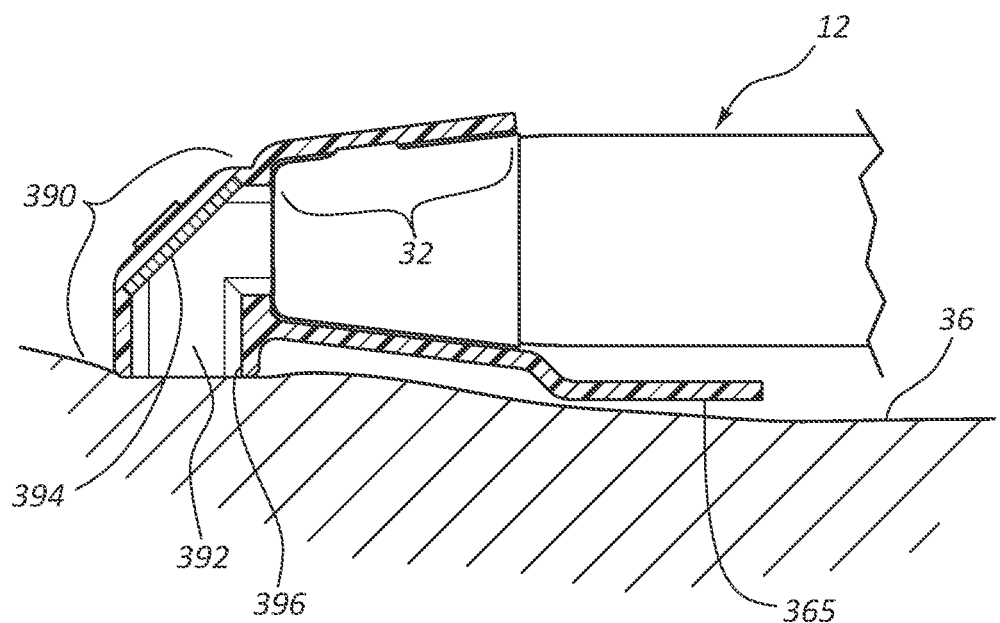
FIG. 31 is a cross-sectional side view of the probe cap of FIGS. 30A and 30B shown attached to an ultrasound probe.

FIG. 31 shows the probe cap 360 positioned against the skin 356 of a patient such that signals emanating from the transducer of the probe head 32 travel through the channel 392, are deflected by the deflecting surface 394, and are directed downward into the body of the patient. Ultrasound signals reflected by an imaged target within the body and received into the channel 392 are also similarly deflected by the deflecting surface 394 toward the probe head 32 for receipt by the transducer. The deflecting surface 394 can include any suitable material having a suitable density so as to reflect the ultrasonic signals travelling through the channel 392. In one embodiment, the deflecting surface includes a plastic material. Also, in one embodiment, the channel 392 is at least partially filled with an ultrasonically transmissive medium, such as an ultrasound gel. In another embodiment, a hydrogel-based spacer component can be disposed in the channel 392, as in previous embodiments. In yet another embodiment, the deflector portion can be integrated into the probe head itself, without the presence of a probe cap. Use of the deflecting probe cap 360 enables the probe 12 to be positioned parallel to the skin 36 of the patient, thus eliminating the need for the clinician to hold the probe upright during use.

Figure 32:
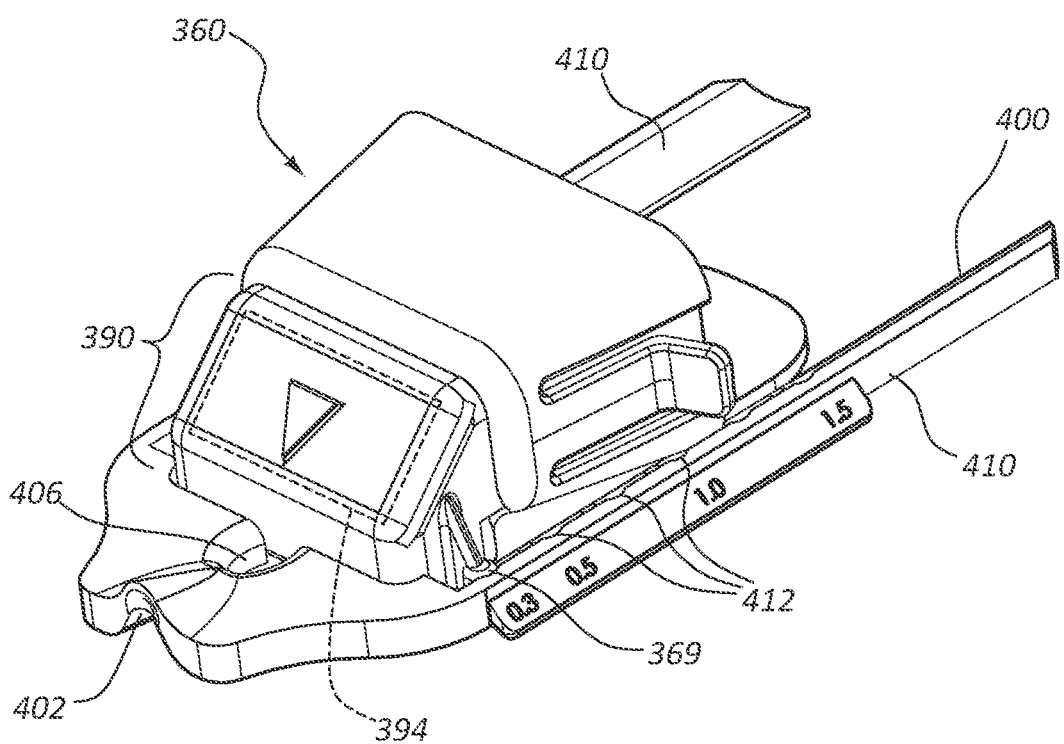
FIG. 32 is a perspective view of a probe cap according to one embodiment.

FIG. 32 shows that the deflecting probe cap 360 in one embodiment can be included as part of an assembly similar to that shown in FIGS. 29A-29D, wherein the cap body is selectively movable between two rails 410 of a bracket 400. The rails 410 each include corresponding slots 412 for receipt of tabs 369 included on the cap body so as to position the probe cap at one of a plurality of possible distances from a needle guide 402 included on the bracket 400. As before, an observation hole 406 is included proximate the needle guide 402. As described further above in connection with FIGS. 29A-29D, the assembly shown in FIG. 32 enables vessels at a variety of subcutaneous depths to be ultrasonically imaged and accessed by a needle disposed in the fixed-angle needle guide 402 by moving the bracket 400 with respect to the probe cap 360 such that the needle intercepts the imaged vessel at the intended depth.

Figure 33A:
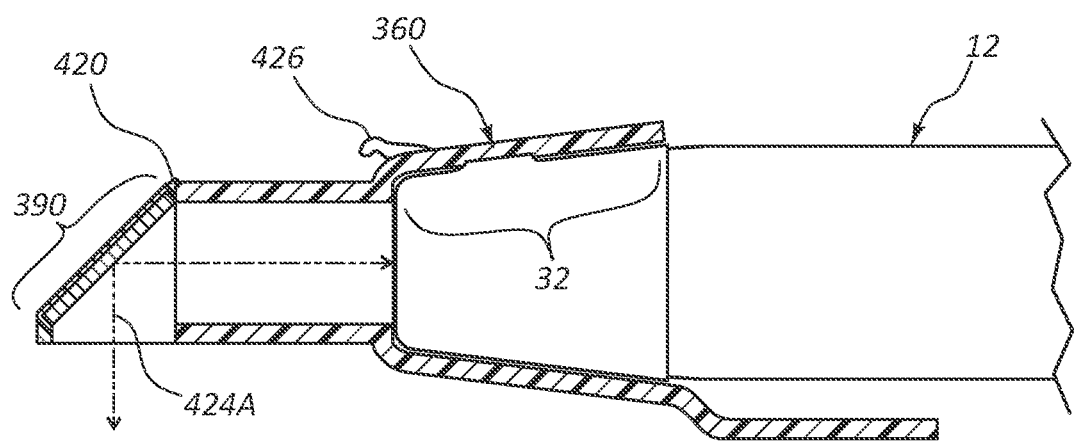
FIGS. 33A and 33B are partial cross-sectional side views of an ultrasound probe and probe cap in accordance with one embodiment.
Figure 33B:
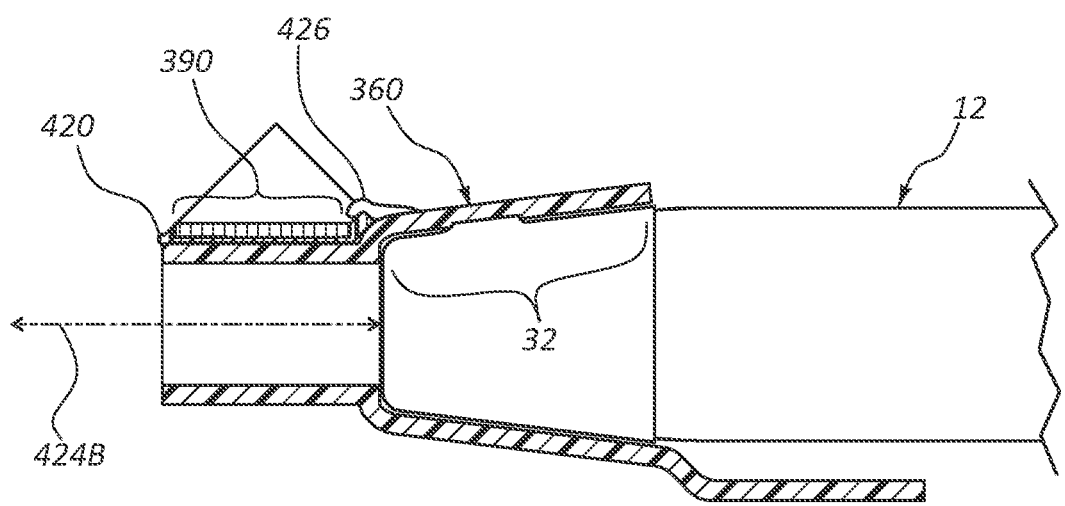

FIGS. 33A and 33B depict the deflecting probe cap 360 according to one embodiment, wherein the deflector portion 390 is hingedly connected to the remainder portion of the cap body via a hinge component 420, including a mechanical or living hinge for instance. So configured, the deflector portion can be selectively positioned so as to deflect ultrasound signals along a deflected signal path 424A (FIG. 33A), or rotated out of the ultrasound signal path (FIG. 33B) so as to enable the ultrasound signals to travel along an undeflected signal path 424B. A latch 426 or other suitable modality can be included to selectively secure the deflector portion 390 in place. Note that in one embodiment a deflecting probe cap can be adjustable such that deflection of the ultrasound signal can be achieved through a variety of angles.

Figure 34:
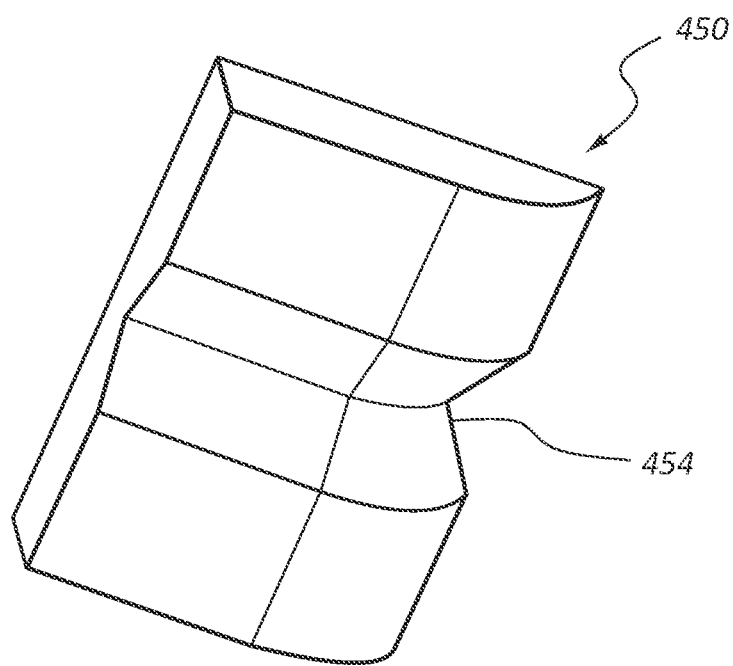
FIG. 34 is a perspective view of a needle guide according to one embodiment.
Figure 35A:
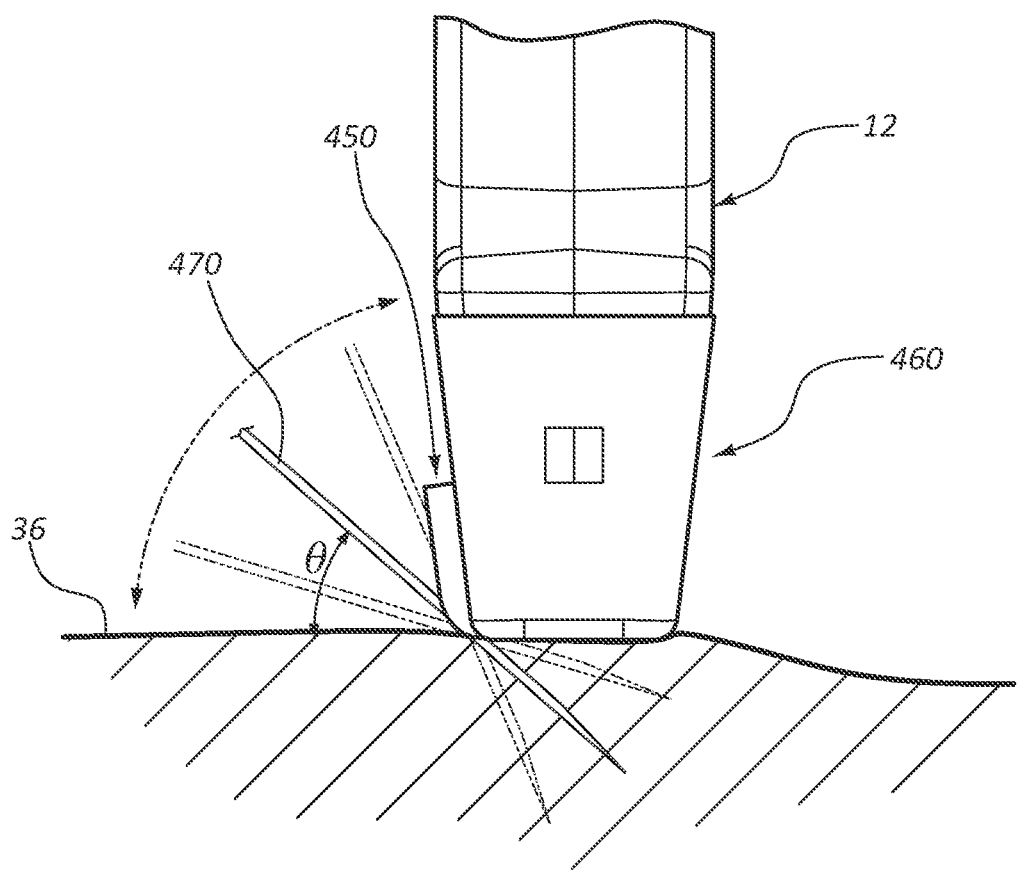
FIGS. 35A and 35B are side and perspective views, respectively, of the needle guide of FIG. 34 attached to a probe cap according to one embodiment.
Figure 35B:
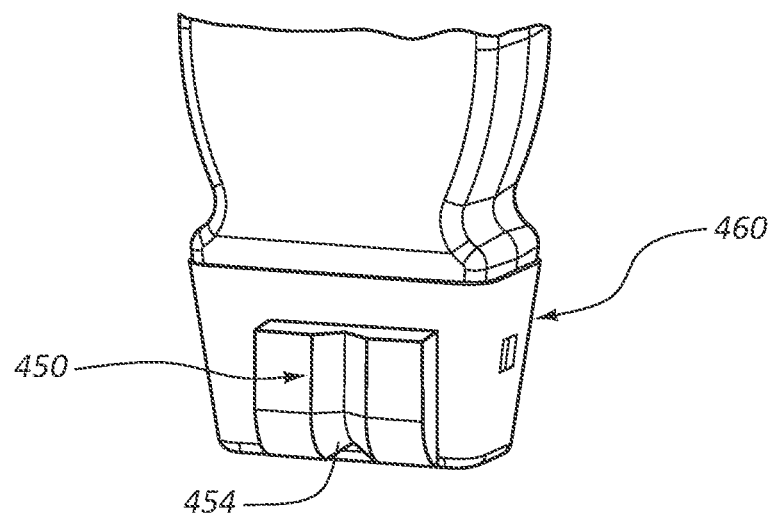

FIG. 34 shows a needle guide 450 according to one embodiment that can be employed with one or more of the probe caps described herein, such as the probe cap 460 shown in FIG. 35B, or can be attached directly to the ultrasound probe. As shown, the needle guide 450 includes a curved, V-shaped open channel 454 that centers a needle therein yet enables the clinician to continuously adjust the angle of attack θ for the needle at the insertion site during needle insertion, as shown in FIG. 35A. Note that the shape of the channel can vary from what is shown and described.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An ultrasound probe assembly, comprising:
   an ultrasound probe including a probe head and an orientation indicator, the probe head including an acoustic surface;
   an ultrasound cap, comprising:
      an opening defined by an opening perimeter; and
      a base configured to support a removable needle guide, wherein:
         the base is a bracket configured to permit the removable needle guide to slide laterally with respect to the ultrasound probe, and
         the base is aligned with the orientation indicator;
   a solid hydrogel component, comprising:
      a probe-contacting side contacting the acoustic surface;
      a skin-contacting side extending through the opening; and
      an outer perimeter larger than the opening perimeter; and
   a cover configured to cover the hydrogel component and at least a portion of the ultrasound cap.

2. The ultrasound probe assembly according to claim 1, wherein the ultrasound cap and the hydrogel component are removable from the ultrasound probe after use.

3. The ultrasound probe assembly according to claim 1, wherein the skin-contacting side of the hydrogel component has a concavity between two end portions.

4. The ultrasound probe assembly according to claim 3, wherein the skin-contacting side of the hydrogel component is symmetrical about a longitudinal axis of the ultrasound probe.

5. The ultrasound probe assembly according to claim 1, wherein the ultrasound probe assembly is pre-assembled with the ultrasound cap, the hydrogel component, and the cover attached to the ultrasound probe.

6. The ultrasound probe assembly according to claim 1, wherein the ultrasound cap includes a mechanical engagement feature to releasably engage the probe head.

7. The ultrasound probe assembly according to claim 1, wherein the outer perimeter of the hydrogel component being larger than the opening perimeter of the ultrasound cap retains the hydrogel component in the ultrasound cap.

8. The ultrasound probe assembly according to claim 1, wherein the hydrogel component includes a lip about the outer perimeter thereof, the lip sandwiched between the ultrasound cap and the probe head of the ultrasound probe.

9. The ultrasound probe assembly according to claim 6, wherein a side of the probe head includes a nub and the ultrasound cap includes a complementary recess for the nub, the nub providing a landmark for orienting an ultrasound image on a display.

10. The ultrasound probe assembly according to claim 9, wherein the complementary recess for the nub is in an opposite side of the ultrasound cap than that including the engagement feature.

11. The ultrasound probe assembly according to claim 1, wherein the ultrasound cap includes a cavity in the base configured to accept the orientation indicator of the ultrasound probe therein.

12. An ultrasound probe assembly, comprising:
an ultrasound probe including a probe head and an orientation indicator, the probe head including an acoustic surface;
an ultrasound cap, comprising:
an opening defined by an opening perimeter; and
a base configured to support a removable needle guide, wherein:
the base is a bracket configured to permit the removable needle guide to slide laterally with respect to the ultrasound probe, and
the base is aligned with the orientation indicator;
a solid, shaped hydrogel component, comprising:
a probe-contacting side contacting the acoustic surface;
a skin-contacting side extending through the opening; and
an outer perimeter larger than the opening perimeter; and
a cover configured to cover the hydrogel component and at least a portion of the ultrasound cap.

13. An ultrasound probe assembly, comprising:
an ultrasound probe including a probe head and an orientation indicator, the probe head including an acoustic surface;
an ultrasound cap, comprising:
an opening defined by an opening perimeter;
a base configured to support a removable needle guide, wherein:
the base is a bracket configured to permit the removable needle guide to slide laterally with respect to the ultrasound probe, and
the base is aligned with the orientation indicator; and
a mechanical engagement feature to releasably engage the probe head;
a solid hydrogel component, comprising:
a probe-contacting side contacting the acoustic surface;
a skin-contacting side extending through the opening; and
an outer perimeter larger than the opening perimeter; and
a cover configured to cover the hydrogel component and at least a portion of the ultrasound cap.

* * * * *